(12) United States Patent
Demarais et al.

(10) Patent No.: US 7,620,451 B2
(45) Date of Patent: Nov. 17, 2009

(54) METHODS AND APPARATUS FOR PULSED ELECTRIC FIELD NEUROMODULATION VIA AN INTRA-TO-EXTRAVASCULAR APPROACH

(75) Inventors: Denise Demarais, Los Gatos, CA (US); Benjamin J. Clark, Redwood City, CA (US); Nicolas Zadno, Fremont, CA (US); Erik Thai, San Jose, CA (US); Hanson Gifford, III, Woodside, CA (US)

(73) Assignee: Ardian, Inc., Palo Alto, CA (US)

( * ) Notice: Subject to any disclaimer, the term of this patent is extended or adjusted under 35 U.S.C. 154(b) by 406 days.

(21) Appl. No.: 11/363,867

(22) Filed: Feb. 27, 2006

(65) Prior Publication Data

US 2007/0203549 A1 Aug. 30, 2007

Related U.S. Application Data

(60) Provisional application No. 60/813,589, filed on Dec. 29, 2005.

(51) Int. Cl.
*A61N 1/32* (2006.01)

(52) U.S. Cl. .................. 607/3; 607/1; 607/2; 607/9; 607/72

(58) Field of Classification Search .............. 607/1–3, 607/9, 72
See application file for complete search history.

(56) References Cited

U.S. PATENT DOCUMENTS

| 2,130,758 A | 9/1938 | Rose |
| 2,276,995 A | 3/1942 | Milinowski |
| 2,276,996 A | 3/1942 | Milinowski |
| 3,043,310 A | 7/1962 | Milinowski |
| 3,127,895 A | 4/1964 | Kendall et al. |

(Continued)

FOREIGN PATENT DOCUMENTS

DE 3151180 A1 8/1982

(Continued)

OTHER PUBLICATIONS

U.S. Appl. No. 60/236,420, Harrison et al.

(Continued)

*Primary Examiner*—Carl H Layno
*Assistant Examiner*—Deborah Malamud
(74) *Attorney, Agent, or Firm*—Perkins Coie LLP

(57) ABSTRACT

Methods and apparatus are provided for pulsed electric field neuromodulation via an intra-to-extravascular approach, e.g., to effectuate irreversible electroporation or electrofusion, necrosis and/or inducement of apoptosis, alteration of gene expression, changes in cytokine upregulation and other conditions in target neural fibers. In some embodiments, the ITEV PEF system comprises an intravascular catheter having one or more electrodes configured for intra-to-extravascular placement across a wall of patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation may be reduced relative to an intravascular PEF system having one or more electrodes positioned solely intravascularly. The methods and apparatus of the present invention may, for example, be used to modulate one or more target neural fibers that contribute to renal function.

34 Claims, 19 Drawing Sheets

U.S. PATENT DOCUMENTS

| | | |
|---|---|---|
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,608,985 A | 9/1986 | Crish et al. |
| 4,649,936 A | 3/1987 | Ungar et al. |
| 4,671,286 A | 6/1987 | Renault |
| 4,674,482 A | 6/1987 | Waltonen et al. |
| 4,692,147 A | 9/1987 | Duggan |
| 4,715,852 A | 12/1987 | Reinicke et al. |
| 4,774,967 A | 10/1988 | Zanakis et al. |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,057,318 A | 10/1991 | Magruder et al. |
| 5,058,584 A | 10/1991 | Bourgeois |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,304,120 A | 4/1994 | Crandell et al. |
| 5,304,206 A | 4/1994 | Baker |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,472,406 A | 12/1995 | de la Torre et al. |
| 5,478,303 A | 12/1995 | Foley-Nolan et al. |
| 5,494,822 A | 2/1996 | Sadri |
| 5,498,238 A | 3/1996 | Shapland et al. |
| 5,499,971 A | 3/1996 | Shapland et al. |
| 5,507,724 A | 4/1996 | Hofmann et al. |
| 5,507,791 A | 4/1996 | Sit'ko |
| 5,531,778 A | 7/1996 | Maschino et al. |
| 5,540,730 A | 7/1996 | Terry, Jr. et al. |
| 5,540,734 A | 7/1996 | Zabara |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,584,863 A | 12/1996 | Rauch et al. |
| 5,589,192 A | 12/1996 | Okabe et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,792,187 A | 8/1998 | Adams |
| 5,800,464 A | 9/1998 | Kieval |

| | | | | | | |
|---|---|---|---|---|---|---|
| 5,807,306 | A | 9/1998 | Shapland et al. | 6,438,423 B1 | 8/2002 | Rezai et al. |
| 5,814,079 | A | 9/1998 | Kieval | 6,442,424 B1 | 8/2002 | Ben-Haim et al. |
| 5,824,087 | A | 10/1998 | Aspden et al. | 6,449,507 B1 | 9/2002 | Hill et al. |
| 5,836,935 | A | 11/1998 | Ashton et al. | 6,450,942 B1 | 9/2002 | Lapanashvili et al. |
| RE35,987 | E | 12/1998 | Harris et al. | 6,461,314 B1 | 10/2002 | Pant et al. |
| 5,843,069 | A | 12/1998 | Butler et al. | 6,464,687 B1 | 10/2002 | Ishikawa et al. |
| 5,861,021 | A | 1/1999 | Thome et al. | 6,473,644 B1 | 10/2002 | Terry, Jr. et al. |
| 5,865,787 | A | 2/1999 | Shapland et al. | 6,482,619 B1 | 11/2002 | Rubinsky et al. |
| 5,871,449 | A | 2/1999 | Brown | 6,508,774 B1 | 1/2003 | Acker et al. |
| 5,891,181 | A | 4/1999 | Zhu | 6,514,226 B1 | 2/2003 | Levin et al. |
| 5,906,636 | A | 5/1999 | Casscells, III et al. | 6,516,211 B1 | 2/2003 | Acker et al. |
| 5,906,817 | A | 5/1999 | Moullier et al. | 6,522,926 B1 | 2/2003 | Kieval et al. |
| 5,913,876 | A | 6/1999 | Taylor et al. | 6,522,932 B1 | 2/2003 | Kuzma et al. |
| 5,916,154 | A | 6/1999 | Hobbs et al. | 6,524,607 B1 | 2/2003 | Goldenheim et al. |
| 5,916,239 | A | 6/1999 | Geddes et al. | 6,534,081 B2 | 3/2003 | Goldenheim et al. |
| 5,919,187 | A | 7/1999 | Guglielmi et al. | 6,536,949 B1 | 3/2003 | Heuser |
| 5,924,997 | A | 7/1999 | Campbell | 6,564,096 B2 | 5/2003 | Mest |
| 5,928,272 | A | 7/1999 | Adkins et al. | 6,571,127 B1 | 5/2003 | Ben-Haim et al. |
| 5,935,075 | A | 8/1999 | Casscells et al. | 6,592,567 B1 | 7/2003 | Levin et al. |
| 5,944,710 | A | 8/1999 | Dev et al. | 6,599,256 B1 | 7/2003 | Acker et al. |
| 5,983,131 | A | 11/1999 | Weaver et al. | 6,600,954 B2 | 7/2003 | Cohen et al. |
| 5,983,141 | A | 11/1999 | Sluijter et al. | 6,600,956 B2 | 7/2003 | Maschino et al. |
| 6,006,134 | A | 12/1999 | Hill et al. | 6,601,459 B1 | 8/2003 | Jenni |
| 6,010,613 | A | 1/2000 | Walters et al. | 6,605,084 B2 | 8/2003 | Acker et al. |
| 6,026,326 | A | 2/2000 | Bardy | 6,615,071 B1 | 9/2003 | Casscells, III et al. |
| 6,051,017 | A | 4/2000 | Loeb et al. | 6,616,624 B1 | 9/2003 | Kieval |
| 6,058,328 | A | 5/2000 | Levine et al. | 6,620,151 B2 | 9/2003 | Blischak et al. |
| 6,058,331 | A | 5/2000 | King | 6,622,041 B2 | 9/2003 | Terry, Jr. et al. |
| 6,073,048 | A | 6/2000 | Kieval et al. | 6,635,054 B2 | 10/2003 | Fjield et al. |
| 6,077,227 | A | 6/2000 | Miesel et al. | 6,666,845 B2 | 12/2003 | Hooper et al. |
| 6,086,527 | A | 7/2000 | Talpade | 6,669,655 B1 | 12/2003 | Acker et al. |
| 6,122,548 | A | 9/2000 | Starkebaum et al. | 6,671,556 B2 | 12/2003 | Osorio et al. |
| 6,123,718 | A | 9/2000 | Tu et al. | 6,672,312 B2 | 1/2004 | Acker |
| 6,146,380 | A | 11/2000 | Racz et al. | 6,676,657 B2 | 1/2004 | Wood |
| 6,161,048 | A | 12/2000 | Sluijter et al. | 6,681,136 B2 | 1/2004 | Schuler et al. |
| 6,178,349 | B1 | 1/2001 | Kieval | 6,684,105 B2 | 1/2004 | Cohen et al. |
| 6,192,889 | B1 | 2/2001 | Morrish | 6,690,971 B2 | 2/2004 | Schauerte et al. |
| 6,205,361 | B1 | 3/2001 | Kuzma et al. | 6,692,738 B2 | 2/2004 | MacLaughlin et al. |
| 6,208,894 | B1 | 3/2001 | Schulman et al. | 6,697,670 B2 | 2/2004 | Chomenky et al. |
| 6,214,032 | B1 | 4/2001 | Loeb et al. | 6,718,208 B2 | 4/2004 | Hill et al. |
| 6,219,577 | B1 | 4/2001 | Brown, III et al. | 6,735,471 B2 | 5/2004 | Hill et al. |
| 6,238,702 | B1 | 5/2001 | Berde et al. | 6,738,663 B2 | 5/2004 | Schroeppel et al. |
| 6,245,026 | B1 | 6/2001 | Campbell et al. | 6,749,598 B1 | 6/2004 | Keren et al. |
| 6,246,912 | B1 | 6/2001 | Sluijter et al. | 6,786,904 B2 | 9/2004 | Doscher et al. |
| 6,251,130 | B1 | 6/2001 | Dobak, III et al. | 6,795,728 B2 | 9/2004 | Chornenky et al. |
| 6,258,087 | B1 | 7/2001 | Edwards et al. | 6,845,267 B2 | 1/2005 | Harrison et al. |
| 6,259,952 | B1 | 7/2001 | Sluijter et al. | 6,850,801 B2 | 2/2005 | Kieval et al. |
| 6,269,269 | B1 | 7/2001 | Ottenhoff et al. | 6,865,416 B2 | 3/2005 | Dev et al. |
| 6,272,377 | B1 | 8/2001 | Sweeney et al. | 6,885,888 B2 | 4/2005 | Rezai |
| 6,272,383 | B1 | 8/2001 | Grey et al. | 6,916,656 B2 | 7/2005 | Walters et al. |
| 6,280,377 | B1 | 8/2001 | Talpade | 6,927,049 B2 | 8/2005 | Rubinsky et al. |
| 6,287,304 | B1 | 9/2001 | Eggers et al. | 6,939,345 B2 | 9/2005 | KenKnight et al. |
| 6,287,608 | B1 | 9/2001 | Levin et al. | 6,958,060 B2 | 10/2005 | Mathiesen et al. |
| 6,292,695 | B1 | 9/2001 | Webster, Jr. et al. | 6,972,013 B1 | 12/2005 | Zhang et al. |
| 6,304,777 | B1 | 10/2001 | Ben-Haim et al. | 6,978,174 B2 | 12/2005 | Gelfand et al. |
| 6,304,787 | B1 | 10/2001 | Kuzma et al. | 6,985,774 B2 | 1/2006 | Kieval et al. |
| 6,306,423 | B1 | 10/2001 | Donovan et al. | 6,994,700 B2 | 2/2006 | Elkins et al. |
| 6,326,020 | B1 | 12/2001 | Kohane et al. | 6,994,706 B2 | 2/2006 | Chornenky et al. |
| 6,326,177 | B1 | 12/2001 | Schoenbach et al. | 7,054,685 B2 | 5/2006 | Dimmer et al. |
| 6,328,699 | B1 * | 12/2001 | Eigler et al. ................. 600/486 | 7,063,679 B2 | 6/2006 | Maguire et al. |
| 6,334,069 | B1 | 12/2001 | George et al. | 7,081,114 B2 | 7/2006 | Rashidi |
| 6,347,247 | B1 | 2/2002 | Dev et al. | 7,081,115 B2 | 7/2006 | Taimisto |
| 6,353,763 | B1 | 3/2002 | George et al. | 7,083,614 B2 | 8/2006 | Fjield et al. |
| 6,356,786 | B1 | 3/2002 | Rezai et al. | 7,122,019 B1 | 10/2006 | Kesten et al. |
| 6,356,787 | B1 | 3/2002 | Rezai et al. | 7,191,015 B2 | 3/2007 | Lamson et al. |
| 6,366,808 | B1 | 4/2002 | Schroeppel et al. | 2001/0044596 A1 | 11/2001 | Jaafar |
| 6,366,815 | B1 | 4/2002 | Haugland et al. | 2002/0026222 A1 | 2/2002 | Schauerte et al. |
| 6,393,324 | B2 | 5/2002 | Gruzdowich et al. | 2002/0026228 A1 | 2/2002 | Schauerte |
| 6,400,982 | B2 | 6/2002 | Sweeney et al. | 2002/0032468 A1 | 3/2002 | Hill et al. |
| 6,405,079 | B1 | 6/2002 | Ansarinia | 2002/0038137 A1 | 3/2002 | Stein |
| 6,405,732 | B1 | 6/2002 | Edwards et al. | 2002/0040204 A1 | 4/2002 | Dev et al. |
| 6,415,183 | B1 | 7/2002 | Scheiner et al. | 2002/0045853 A1 | 4/2002 | Dev et al. |
| 6,415,187 | B1 | 7/2002 | Kuzma et al. | 2002/0072782 A1 | 6/2002 | Osorio et al. |

| Publication No. | Date | Inventor |
|---|---|---|
| 2002/0107553 A1 | 8/2002 | Hill et al. |
| 2002/0116030 A1 | 8/2002 | Rezai |
| 2002/0120304 A1 | 8/2002 | Mest |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0040774 A1 | 2/2003 | Terry et al. |
| 2003/0045909 A1 | 3/2003 | Gross et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0100924 A1 | 5/2003 | Foreman et al. |
| 2003/0120270 A1 | 6/2003 | Acker |
| 2003/0150464 A1 | 8/2003 | Casscells |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0236443 A1 | 12/2003 | Cespedes et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0220511 A1 | 11/2004 | Scott et al. |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0100667 A1 | 5/2006 | Machado et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0229677 A1 | 10/2006 | Moffitt et al. |
| 2006/0235474 A1 | 10/2006 | Demarais |
| 2006/0265015 A1 | 11/2006 | Demarais et al. |

FOREIGN PATENT DOCUMENTS

| | | |
|---|---|---|
| EP | 0811395 A2 | 6/1997 |
| WO | WO-85/01213 | 3/1985 |
| WO | WO-91/04725 | 4/1991 |
| WO | WO-93/02740 | 2/1993 |
| WO | WO-93/07803 | 4/1993 |
| WO | WO-94/00188 | 1/1994 |
| WO | WO-96/04957 | 1/1995 |
| WO | WO-95/33514 | 12/1995 |
| WO | WO-96/11723 | 4/1996 |
| WO | WO-97/13550 | 4/1997 |
| WO | WO-97/49453 | 12/1997 |
| WO | WO-98/37926 | 9/1998 |
| WO | WO-98/43700 | 10/1998 |
| WO | WO-98/43701 | 10/1998 |
| WO | WO-98/48888 | 11/1998 |
| WO | WO-99/33407 | 7/1999 |
| WO | WO-99/51286 | 10/1999 |
| WO | WO-99/52424 | 10/1999 |
| WO | WO-01/26729 | 4/2001 |
| WO | WO-02/09808 | 2/2002 |
| WO | WO-02/26314 | 4/2002 |
| WO | WO-02/053207 | 7/2002 |
| WO | WO-02/070039 A2 | 9/2002 |
| WO | WO-02/070047 | 9/2002 |
| WO | WO-02/085448 | 10/2002 |
| WO | WO-03/018108 | 3/2003 |
| WO | WO-03/028802 | 4/2003 |
| WO | WO-03/063692 | 8/2003 |
| WO | WO-03/071140 A2 | 8/2003 |
| WO | WO-03/076008 | 9/2003 |
| WO | WO-03/082080 | 10/2003 |
| WO | WO-03/082403 | 10/2003 |
| WO | WO-2004/026370 | 4/2004 |
| WO | WO-2004/026371 | 4/2004 |
| WO | WO-2004/026374 | 4/2004 |

| | | |
|---|---|---|
| WO | WO-2004/030718 | 4/2004 |
| WO | WO-2004/032791 | 4/2004 |
| WO | WO-2004/107965 | 12/2004 |
| WO | WO-2005014100 | 2/2005 |
| WO | WO-2005016165 | 2/2005 |
| WO | WO-2005/032646 | 4/2005 |
| WO | WO-2005/065284 | 7/2005 |
| WO | WO-2005/084389 A2 | 9/2005 |
| WO | WO-2005/097256 A2 | 10/2005 |
| WO | WO-2005/123183 | 12/2005 |
| WO | WO-2006/007048 A2 | 1/2006 |
| WO | WO-2006018528 A1 | 2/2006 |
| WO | WO-2006/031899 A2 | 3/2006 |
| WO | WO-2006/041881 | 4/2006 |
| WO | WO-2007/078997 | 7/2007 |
| WO | WO-2007/146834 | 12/2007 |
| WO | WO-2008/061150 | 5/2008 |

OTHER PUBLICATIONS

U.S. Appl. No. 60/370,190.
U.S. Appl. No. 60/408,665.
U.S. Appl. No. 60/415,575.
U.S. Appl. No. 60/442,970.
"Atrial Fibrillation" Heart and Vascular Health on Yahoo! Health. 2 pages. <URL: http://health.yahoo.com/topic/heart/overview/article/healthwise/hw160872;_ylt=AiBT43Ey74HQ7ft3jAb4C.sPu7cF>.
"Heart Arrhythmia" Heart and Vascular Health on Yahoo! Health. 13 pages. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF>.
"Isovue: Data Sheet". Regional Health Limited. 8 pages. Mar. 11, 2003.
"Micro ETS Hyperhidrosis USA" Hyperhidrosis USA. 2 pages. <URL: http://www.hyperhidrosis-usa.com/Index.html>.
Amersham Health. "Hypaque-Cysto" 6 pages. 2003.
Arentz, Thomas et al. "Incidence of pulmonary vein stenosis 2 years after radiofrequency catheter ablation of refractory atrial fibrillation." European Heart Journal. 2003. 24; pp. 963-969.
Boehmer, John P. "Resynchronization Therapy for Chronic CHF: Indications, Devices and Outcomes". Penn State College of Medicine: Penn State Heart and Vascular Institute. Transcatheter Cardiovascular Therapeutics 2005. 31 slides.
Bourge, Robert C. "Heart Failure Monitoring Devices: Rationale and Status" 28 pages.
Braunwald, E., Heart Disease, "A Textbook of Cardiovascular Medicine," 5th Ed., vol. 2, 1997, pp. 480-481, 824-825, 1184-1288 and 1923-1925, W.B. Saunders Company.
Bunch, Jared T. et al. "Mechanisms of Phrenic Nerve Injury During Radiofrequency Ablation at the Pulmonary Vein Orifice." Journal of Cardiovascular Electrophysiology. vol. 16, No. 12. pp. 1318-1325. Dec. 2005.
Burkhoff, Daniel. "Interventional Device-Based Therapy For CHF Will Redefine Current Treatment Paradigms". Columbia University. 2004. 32 slides.
Canbaz, Suat et al. "Electrophysiological evaluation of phrenic nerve injury during cardiac surgery—a prospective, controlled clinical study." BioMed Central. 5 pages. 2004.
Carson, Peter. "Device-based Treatment For Chronic Heart Failure: Electrical Modulation of Myocardial Contractility". Transcatheter Cardiovascular Therapeutics 2005. 21 slides.
Chiou, CW et al. "Efferent Vagal Innervation of the Canine Atria and Sinus and Atrioventricular Nodes". Circulation. Jun. 1997. 95(11):2573-2584. Abstract only. 2 pages.
Cryovascular Systems, Inc. "Pre-Clinical Testing Establishing Parameters". PowerPoint Presentation. 18 slides.
Daniel, Alan and Honig, Carl R. "Does Histamine Influence Vasodilation Caused by Prolonged Arterial Occlusion or Heavy Exercise?" The Journal of Pharmacology and Experimental Therapeutics. vol. 215 No. 2. Aug. 21, 1980. pp. 533-538.
Dong, Jun et al. "Incidence and Predictors of Pulmonary Vein Stenosis Following Catheter Ablation of Atrial Fibrillation Using the Anatomic Pulmonary Vein Ablation Approach: Results from Paired Magnetic Resonance Imaging." Journal of Cardiovascular Electrophysiology. vol. 16, No. 8, Aug. 2005, pp. 845-852.
Fava, M. "Clinical Testing Establishing Safety & Efficacy". PowerPoint Presentation. Cryovascular Systems, Inc. 14 slides.
Fava, M. et al. "Initial Human Experience with CryoPlasty™ in the Treatment of Infrainguinal Arterial Disease." Abstract. 1 page.
Fischell, Tim A. et al. "Ultrasonic Energy: Effects on Vascular Function and Integrity." Circulation: Journal of the American Heart Association. 1991. 84;pp. 1783-1795.
Hodgkin, Douglas D. et al. "Electrophysiologic Characteristics of a Pulsed Iontophoretic Drug-Delivery System in Coronary Arteries." Journal of Cardiovascular Pharmacology. 29(1):pp. 39-44, Jan. 1997. Abstract. 2 pages.
International Search Report, PCT/US04/38498, Mailed Feb. 18, 2005, Applicant: G & L Consulting, LLC (3 pages).
Jia, Jianping and Pollock, Martin. "The pathogenesis of non-freezing cold nerve injury: Observations in the rat." Brain. 120;pp. 631-646. 1997.
Jia, Jianping et al. "Cold injury to nerves is not due to ischaemia alone." Brain. 121;pp. 989-1001. 1998.
Jin, Yuanzhe. Et al. "Pulmonary Vein Stenosis and Remodeling After Electrical Isolation for Treatment of Atrial Fibrillation: Short- and Medium-Term Follow-Up." PACE, vol. 27, pp. 1362-1370. Oct. 2004.
Joye, James D. and Tatsutani, Kristine. "In Vitro Studies of Arterial Freezing Injury". 4 pages.
Joye, James D. and Tatsutani, Kristine. "In Vivo Study of Endovascular Cryotherapy for the Prevention of Restenosis." 4 pages.
Knot, Harm J. and Nelson, Mark T. "Regulation of arterial diameter and wall [Ca2+] in cerebral arteries of rat by membrane potential and intravascular pressure." The Journal of Physiology. 1998. 508; pp. 199-209.
Kok, Lai Chow et al. "Effect of Heating on Pulmonary Veins: How to Avoid Pulmonary Vein Stenosis." Journal of Cardiovascular Electrophysiology. vol. 14, No 3, Mar. 2003. pp. 250-254.
Lee, Michael A. (editor). SPORTSMed. Connecticut State Medical Society Committee on the Medical Aspects of Sports. Fall/Winter 2005. 10 pages.
Mathur, Vandana S. "Intra-Renal Drug Delivery for Fluid Overload". FlowMedica. Transcatheter Cardiovascular Therapeutics 2005. 31 slides.
Mehran, Roxana. "Renal insufficiency and contrast nephropathy: The most common, least understood risk factor". Cardiovascular Research Foundation. Columbia University Medical Center. 2005. 86 slides.
Packer, Douglas L. et al. "Clinical Presentation, Investigation, and Management of Pulmonary Vein Stenosis Complication Ablation for Atrial Fibrillation." Circulation: Journal of the American Heart Association. Feb. 8, 2005. pp. 546-554.
Pappone, Carlo and Santinelli, Vincenzo. "[2005][P2-70] Safety Report of Circumferential Pulmonary Vein Ablation. A 9-Year Single-Center Experience on 6,442 Patients with Atrial Fibrillation." Abstract only. 1 page.
Pappone, Carlo et al. "[2004][759] Pulmonary Vein Denervation Benefits Paroxysmal Atrial Fibrillation Patients after Circumferential Ablation." Abstract only. 1 page.
Purerfellner, Helmut and Martinek, Martin. "Pulmonary vein stenosis following catheter ablation of atrial fibrillation." Current Opinion in Cardiology. 20; pp. 484-490. 2005.
Purerfellner, Helmut et al. "Pulmonary Vein Stenosis by Ostial Irrigated-Tip Ablation: Incidence, Time Course, and Prediction." Journal of Cardiovascular Electrophysiology. vol. 14, No. 2, Feb. 2003. pp. 158-164.
Saad, Eduardo B. et al. "Pulmonary Vein Stenosis After Radiofrequency Ablation of Atrial Fibrillation: Functional Characterization, Evolution, and Influence of the Ablation Strategy." Circulation. 108; pp. 3102-3107. 2003.
Sabbah, Hani N. "Animal Models for Heart Failure and Device Development". Henry Ford Health System. 24 slides.
Schauerte, P et al. "Catheter ablation of cardiac autonomic nerves for prevention of vagal atrial fibrillation." Circulation. 102(22). Nov. 28, 2000. Abstract only. 2 pages.

Schauerte, P et al. "Focal atrial fibrillation: experimental evidence for a pathophysiologic role of the autonomic nervous system." Journal of Cardiovascular Electrophysiology. 12(5). May 2001. Abstract only. 2 pages.

Schauerte, P. et al. "Transvenous parasympathetic nerve stimulation in the inferior vena cava and atrioventricular conduction." Journal of Cardiovascular Electrophysiology. 11(1). Jan. 2000. Abstract only. 2 pages.

Scherlag, BJ and Po, S. "The intrinsic cardiac nervous system and atrial fibrillation." Current Opinion in Cardiology. 21(1):51-54, Jan. 2006. Abstract only. 2 pages.

Schmitt, Joseph et al. "Intravascular Optical Coherence Tomography—Opening a Window into Coronary Artery Disease". LightLab Imaging, Inc. Business Briefing: European Cardiology 2005.

Serrador, Jorge M. "Autonomic Regulation of the Cardiovascular System". MIT Lecture. 8 pages, 48 slides.

Siegel, RJ et al. "Clinical demonstration that catheter-delivered ultrasound energy reverses arterial vasoconstriction." Journal of the American College of Cardiology. 1992. 20; 732-735. Summary only. 2 pages.

Sobotka, Paul A. "Treatment Strategies for Fluid Overload, CHF Patients". CHF Solutions. Transcatheter Cardiovascular Therapeutics 2005. 20 slides.

Steffen, W. et al. "Catheter-delivered high intensity, low frequency ultrasound induces vasodilation in vivo." European Heart Journal. 1994. 15;pp. 369-376.

Steg, PG et al. "Pulsed ultraviolet laser irradiation produces endothelium-independent relaxation of vascular smooth muscle". Circulation: Journal of the American Heart Association. 1989. pp. 189-197.

Taka, Tomomi et al. "Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats". Pathophysiology of Haemostasis and Thrombosis. Dec. 23, 2002. pp. 184-189.

Tamborero, David et al. "Incidence of Pulmonary Vein Stenosis in Patients Submitted to Atrial Fibrillation Ablation: A Comparison of the Selective Segmental Ostial Ablation vs. the Circumferential Pulmonary Veins Ablation." Journal of Intervocational Cardiac Electrophysiology. 14; pp. 41-25. 2005.

Terashima, Mitsuyasu et al. "Feasibility and Safety of a Novel CryoPlasty™ System". Poster. 1 page.

Thomas, John R. And Oakley, E. Howard N. "Chapter 15: Nonfreezing Cold Injury" *Medical Aspects of Harsh Environments*, vol. 1. pp. 467-490.

Vince, D. Geoffrey. "Virtual Histology: A new technique for the assessment of plaque composition". The Cleveland Clinic Foundation. 28 pages.

Yu, Wen-Chung et al. "Acquired Pulmonary Vein Stenosis after Radiofrequency Catheter Ablation of Paroxysmal Atrial Fibrillation." Journal of Cardiovascular Electrophysiology. vol. 12, No. 8. Aug. 2001. pp. 887-892.

U.S. Appl. No. 11/504,117, Demarais et al.
U.S. Appl. No. 11/599,649, Demarais et al.
U.S. Appl. No. 11/599,723, Demarais et al.
U.S. Appl. No. 11/599,882, Demarais et al.
U.S. Appl. No. 11/599,890, Demarais et al.
U.S. Appl. No. 11/688,178, Levin et al.
U.S. Appl. No. 11/129,765, filed May 13, 2005, Deem.
U.S. Appl. No. 11/144,173, filed Jun. 3, 2005, Levin et al.
U.S. Appl. No. 11/145,122, filed Jun. 3, 2005, Levin et al.
U.S. Appl. No. 11/189,563, filed Jul. 25, 2005, Deem.
U.S. Appl. No. 11/144,298, filed Jun. 3, 2005, Levin et al.
U.S. Appl. No. 11/133,925, filed May 20, 2005, Gelfand.
U.S. Appl. No. 10/900,199, filed Jul. 28, 2004, Gelfand.
U.S. Appl. No. 11/266,993, Denise Demarais.
U.S. Appl. No. 11/368,553, Demarais.
U.S. Appl. No. 11/368,971, Denise Demarais.
U.S. Appl. No. 11/368,809, Denise Demarais.
U.S. Appl. No. 11/368,949, Denise Demarais.
U.S. Appl. No. 11/368,577, Demarais.
U.S. Appl. No. 11/368,836, Demarais.
U.S. Appl. No. 11/324,188, Denise Demarais.
U.S. Appl. No. 11/252,462, Denise Demarais.
U.S. Appl. No. 11/233,814, Denise Demarais.
U.S. Appl. No. 10/408,665, filed Apr. 8, 2003, Levin et al.

"2003 European Society of Hypertension-European Society of Cardiology guidelines for the management of arterial hypertension," Journal of Hypertension 2003, vol. 21, No. 6, pp. 1011-1053.

"Advanced Neuromodulation Systems' Comparison Chart," 1 page.

"Advances in the role of the sympathetic nervous system in cardiovascular medicine," 2001 SNS Report, No. 3, Springer, published with an educational grant from Servier, pp. 1-8.

"Cardiac Glycosides," Heart Disease—A Text Book of Cardiovascular Medicine vol. 2, Edited by Eugene Braunwald, 5th Edition, WB Saunders Company, pp. 480-481.

"Clinical Trials in Hypertension and Renal Diseases," Slide Source, www.hypertensiononline.org, 33 pages.

"ECM 830 Specifications Sheet," tech@genetronics.com, 20-001796-01 Rev D, 2 pages.

"Effects of Renal Failure on the Cardiovascular System," 5th Edition Heart Disease, A Textbook of Cardiovascular Medicine, vol. 2, Edited by Eugene Braunwald, W.B. Saunders Company, pp. 1923-1925.

"Electrical Stimulation for the Treatment of Chronic Wounds," Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pages.

"Electropermeabilization (Electroporation)," Cyto Pulse Sciences Inc., http://www.cytopulse.com/electroporation.html (last accessed Mar. 3, 2005), 3 pages.

"Electroporation based Technologies and Treatments," ESPE Newsletter No. 6, QLK 02002-2003, Jan. 2005, www.cliniporator.com, 4 pages.

"End-stage renal disease payment policies in traditional Medicare," Report to the Congress: Medicare Payment Policy, Mar. 2001, Medpac, pp. 123-138.

"Epidemiology of Renal Disease in Hypertension," slide presentation by hypertensiononline.org, 21 pages.

"Fact Book Fiscal Year 2003," National Institutes of Health National Heart, Lung, and Blood Institute, Feb. 2004, 197 pages.

"Heart Disease and Stroke Statistics-2004 update," American Heart Association, American Stroke Association, Dallas, Texas, © 2003 American Heart Association, 52 pages.

"Hypertension and Renal Disease: Mechanisms," Slide Show by www.hypertensiononline.org, 22 pages.

"Hypertension Incidence and Prevalence, Age Specific Rates, By Gender, B.C., 2001/2002," Graph., Chronic Disease Management, May 2003, British Columbia Ministry of Health Services, 1 page.

Implantable Pump—The Medtronic MiniMed 2007 Implantable Insulin Pump System, Medtronic MiniMed 2004, 4 pages.

"Infumedics Inc.,"Background and products paper and comparison of Medtronic SynchroMed II and Infumedics Prometra pumps, 3 pages.

"Introduction to Autonomic Pharmacology," Chapter 3, Part 2 Autonomic Pharmacology, pp. 18-26.

Aars, H. and S. Akre, "Reflex Changes in Sympathetic Activity and Arterial Blood Pressure Evoked by Afferent Stimulation of the Renal Nerve," Feb. 26, 1999, Acta Physiol. Scand., vol. 78, 1970, pp. 184-188.

Abramov, G.S. et al., "Alteration in sensory nerve function following electrical shock," Burns vol. 22, No. 8, © 1996 Elsevier Science Ltd., pp. 602-606.

Achar, Suraj, M.D. And Suriti Kundu, M.D., "Principles of Office Anesthesia: Part I Infiltrative Anesthesia," Office Procedures, American Family Physician, Jul. 1, 2002, vol. 66, No. 1, pp. 91-94.

Agnew, William F. et al., "Evolution and Resolution of Stimulation-Induced Axonal Injury in Peripheral Nerve," May 21, 1999, Muscle and Nerve, vol. 22, Oct. 1999, © 1999 John Wiley & Sons, pp. 1393-1402.

Ahadian, Farshad M., M.D., "Pulsed Radiofrequency Neurotomy: Advances in Pain Medicine," Current Pain and Headache Reports 2004, vol. 8, © 2004 Current Science Inc., pp. 34-40.

Alford, J.Winslow, M.D. and Paul. D. Fadale, M.D., "Evaluation of Postoperative Bupivacaine Infusion for Pain Management After Anterior Cruciate Ligament Reconstruction," The Journal of Arthroscopic and Related Surgery October, vol. 19, No. 8, © 2003 Arthroscopy Association of North America, pp. 855-861.

Andrews, B.T. et al., "The use of surgical sympathectomy in the treatment of chronic renal pain," Mar. 5, 1997, British Journal of Urology, vol. 80, © 1997 British Journal of Urology, pp. 6-10.

Antman, Elliott M. and Eugene Braunwald, "Chapter 37—Acute Myocardial Infarction," Heart Disease—A Textbook of Cardiovascular Medicine, 5th Edition, vol. 2, 1997, Edited by Eugene Braunwald, pp. 1184-1288.

Archer, Steffan et al., "Cell Reactions to Dielectrophoretic Manipulation," Mar. 1, 1999, Biochemical and Biophysical Research Communications, 1999 Academic Press, pp. 687-698.

Arias, Manuel J., M.D., "Percutaneous Radio Frequency Thermocoagulation with Low Temperature in the Treatment of Essential Glossopharyngeal Neuralgia," Surg. Neurol. 1986, vol. 25, © 1986 Elsevier Science Publishing Co. Inc., pp. 94-96.

Aronofsky, David H., D.D.S., "Reduction of dental postsurgical symptoms using nonthermal pulsed high-peak-power electromagnetic energy," Oral Surg., Nov. 1971, vol. 32, No. 5, pp. 688-696.

Aspelin, Peter, M.D., Ph.D. et al, "Nephrotoxic Effects in High-Risk Patients Undergoing Angiography," Feb. 6, 2003, New England Journal of Medicine 2003, vol. 348, No. 6, 2003 Massachusetts Medical Society, pp. 491-499.

Augustyniak, Robert A. et al., "Sympathetic Overactivity as a Cause of Hypertension in Chronic Renal Failure," Aug. 14, 2001, Journal of Hypertension, 2002, vol. 20, 2002 Lippincott Williams & Wilkins, pp. 3-9.

Awwad, Ziad M., FRCS and Bashir A. Atiyat, GBA, JBA, "Pain relief using continuous bupivacaine infusion in the paravertebral space after loin incision," May 15, 2004, Saudi Med. J. 2004, vol. 25, No. 10, pp. 1369-1373.

Badyal, D.K., H. Lata and A.P. Dadhich, "Animal Models of Hypertension and Effect of Drugs," Aug. 19, 2003, Indian Journal of Pharmacology 2003, vol. 35, pp. 349-362.

Baker, Carol E. et al., "Effect of pH of Bupivacaine on Duration of Repeated Sciatic Nerve Blocks in the Albino Rat," Anesth. Analg. 1991, vol. 72, © 1991 The International Anesthesia Research Society, pp. 773-778.

Balazs, Tibor, "Development of Tissue Resistance to Toxic Effects of Chemicals," Jan. 26, 1974, Toxicology, vol. 2, © 1974 Elsevier/North Holland, Amsterdam, pp. 247-255.

Barrett, Carolyn J. et al., "Long-term control of renal blood flow: what is the role of renal nerves?" Jan. 4, 2001, Am. J. Physiol. Regulatory Integrative Comp. Physiol. 2001, vol. 280, © the American Physiological Society, pp. R1534-R1545.

Barrett, Carolyn J. et al., "What Sets The Long-Term Level of Renal Sympathetic Nerve Activity?, " May 12, 2003, Integrative Physiology, Circulation Research 2003, vol. 92, © 2003 American Heart Association, pp. 1330-1336.

Bassett, C. Andrew L. et al., "Augmentation of Bone Reapair by Inductively Coupled Electromagnetic Fields," May 3, 1974, Science, vol. 184, pp. 575-577.

Bassett, C. Andrew L., "Fundamental and Practical Aspects of Therapeutic Uses of Pulsed Electromagnetic Fields (PEMFs)," Critical Reviews in Biomedical Engineering, vol. 17, No. 5, 1989, pp. 451-514.

Beebe, Stephen J. et al., "Nanosecond Pulsed Electric Field (nsPEF) Effects on Cells and Tissues: Apoptosis Induction and Tumor Growth Inhibition," Oct. 11, 2001, IEEE Transactions on Plasma Science, vol. 30, No. 1, Feb. 2002, © 2002 IEEE, pp. 286-292.

Beebe, Stephen J. et al., "Nanosecond pulsed electric fields modulate cell function through intracellular signal transduction mechanisms," Apr. 8, 2004, Physiological Measurement, vol. 25, 2004, © 2004 IOP Publishing Ltd., pp. 1077-1093.

Berde, Charles and Gary R. Strichartz, "Local Anesthetics," Anesthesia, Chapter 13, 5th addition, Churchill-Livingston, Philadelphia 2000, pp. 491-521.

Bhadra, Niloy and Kevin L. Kilgore, "Direct Current Electrical Conduction Block of Peripheral Nerve," Feb. 25, 2004, IEEE Transactions on Neural Systems and Rehabilitation Engineering, vol. 12, No. 13, Sep. 2004, pp. 313-324.

Bhatt, Deepak L. et al., "Rhabdomyolysis Due to Pulsed Electric Fields," May 11, 1989, Plastic and Reconstructive Surgery Jul. 1990, pp. 1-11.

Bigler, D. et al., "Tachyphylaxis during postoperative epidural analgesia-new insights," Apr. 15, 1987, Letter to the Editor, Acta Anesthesiol. Scand. 1987, vol. 31, pp. 664-665.

Binder, Allan et al., "Pulsed Electromagnetic Field Therapy of Persistent Rotator Cuff Tendinitis," The Lancet, Saturday Mar. 31, 1984, The Lancet Ltd., pp. 695-698.

Black, Henry R., M.D., "Resistant Hypertension 2004," presentation at Rush University Medical Center, Jul. 15, 2004, 40 pages.

Blad, B., et al., "An Electrical Impedance index to Assess Electroporation in Tissue," Tissue and Organ (Therapy) 2001, Oslo, pp. 31-34.

Blair, M.L. et al., "Sympathetic activation cannot fully account for increased plasma renin levels during water deprivation," Sep. 23, 1996, Am J Physiol 1997, vol. 272, © 1997 the American Physiological Society, pp. R1197-R1203.

Blomberg, Sture G., M.D., Ph.D., "Long-Term Home Self-Treatment with High Thoracic Epidural Anesthesia in Patients with Severe Coronary Artery Disease," Mar. 29, 1994, Anesth. Analg. 1994, vol. 79, © 1994 International Anesthesia Research Society, pp. 413-421.

Cahana, A. et al., "Acute Differential Modulation of Synaptic Transmission and Cell Survival During Exposure to Pulsed and Continuous Radiofrequency Energy," The Journal of Pain, May 2003, vol. 4, No. 4, © 2003 by the American Pain Society, pp. 197-202.

Cahana, Alex, M.D., "Pulsed Radiofrequency: A Neurobiologic and Clinical Reality," May 17, 2005, Anesthesiology 2005, vol. 103, No. 6, Dec. 2005, © 2005 American Society of Anesthesiologists, Inc., Lippincott Williams & Wilkins, Inc., p. 1311.

Calaresu, F.R. et al., "Haemodynamic Responses and Renin Release During Stimulation of Afferent Renal Nerves in the Cat," Aug. 12, 1975, J. Physiol. 1976, vol. 255, pp. 687-700.

Campese, V.M. et al., "Renal Afferent Denervation Prevents the Progression of Renal Disease in the Renal Ablation Model of Chronic Renal Failure in the Rat," Jun. 13, 1995, American Journal of Kidney Diseases 1995, vol. 26, No. 5, 1995 the National Kidney Foundation, Inc., pp. 861-865.

Campese, V.M., "A new model of neurogenic hypertension caused by renal injury: pathophysiology and therapeutic implications," Clin. Exp. Nephrol 2003, vol. 7, © 2003 Japanese Society of Nephroloogy, pp. 167-171.

Campese, V.M., "Neurogenic factors and hypertension in chronic renal failure," Journal of Nephrology, vol. 10, No. 4, © 1997 Societa Italiana di Nefrologia, pp. 184-187.

Carls, G., et al., "Electrical and magnetic stimulation of the intercostal nerves: a comparative study," Electromyogr. clin. Neurophysiol., vol. 37, 1997, pp. 509-512.

Carlson, Scott H. and J. Michael Wyss, "e-Hyertension, Opening New Vistas,"Introductory Commentary, Hypertension 2000, vol. 35, American Heart Association, Inc., 2000, p. 538.

Chang, Donald C., "Cell poration and cell fusion using an oscillating electric field," Biophysical Journal, vol. 56, Oct. 1989, Biophysical Society, pp. 641-652.

Chobanian, Aram V. et al., "Seventh Report of the Joint National Committee on Prevention, Detection, Evaluation, and Treatment of High Blood Pressure," Nov. 6, 2003, Hypertension 2003, vol. 42, © 2003 American Heart Association, Inc., pp. 1206-1252.

Codman 3000, Implantable Constant-Flow Infusion Pump Pamphlet, For Continuous Intrathecal Drug Delivery, 2 pages.

Conradi, E., Ines Helen Pages, "Effects of Continuous and Pulsed Microwave Irradiation on Distribution of Heat in the Gluteal Region of Minipigs," Scand. J. Rehab. Med., vol. 21, 1989, pp. 59-62.

Converse Jr., R.L. et al., "Sympathetic Overactivity in Patients with Chronic Renal Failure," New England Journal of Medicine, Dec. 31, 1992, vol. 327 (27), pp. 1912-1918.

Cosman, Eric R., Jr. et al., "Electric and Thermal Field Effects in Tissue Around Radiofrequency Electrodes," Pain Medicine, vol. 6, No. 6, 2005, American Academy of Pain Medicine, pp. 405-424.

Cosman, Eric R., Ph.D., "A Comment on the History of the Pulsed Radiofrequency Technique for Pain Therapy," Anesthesiology Dec. 2005, vol. 103, No. 6, © 2005 American Society of Anesthesiologists, Inc. Lippincott Williams & Wilkins, Inc., p. 1312.

Crawford, William H. et al., "Pulsed Radio Frequency Therapy of Experimentally Induced Arthritis in Ponies," Dec. 18, 1989, Can. J. Vet. Res. 1991, vol. 55, pp. 76-85.

Dahm, Peter et al., "Efficacy and Technical Complications of Long-Term Continuous Intraspinal Infusions of Opioid and/or Bupivacaine in Refractory Nonmalignant Pain . . . ," Oct. 6, 1997, The Clinical Journal of Pain 1998, vol. 14, No. 1, © 1998 Lippincott-Raven Publishers, pp. 4-16.

Dahm, Peter O. et al., "Long-Term Intrathecal Infusion of Opioid and/or Bupivacaine in the Prophylaxis and Treatment of Phantom Limb Pain," Neuromodulation 1998, vol. 1, No. 3, © 1998 International Neuromodulation Society, pp. 111-128.

Dang, Nicholas C. et al., "A Novel Approach to Increase Total Urine Output in Heart Failure: Renal Nerve Blockade," ACC 2005 poster, 1 page.

Davalos, R. et al., "Electrical Impedance Tomography for Imaging Tissue Electroporation," Jul. 25, 2003, IEEE Transactions on Biomedical Engineering, vol. 51, No. 5, May 2004, IEEE 2004, pp. 761-767.

Davalos, R.V. et al., "Tissue Ablation with Irreversible Electroporation," Sep. 7, 2004, Annals of Biomedical Engineering, vol. 33, No. 2, © 2005 Biomedical Engineering Society, pp. 223-231.

De Leeuw, Peter W. et al., "Renal Vascular Tachyphylaxis to Angiotensin II: Specificity of the Response for Angiotensin," Dec. 28, 1981, Life Sciences, vol. 30, © 1982 Pergamon Press Ltd., pp. 813-819.

Deng, Jingdong et al., "The Effects of Intense Submicrosecond Electrical Pulses on Cells," Nov. 26, 2002, Biophysical Journal, vol. 84, Apr. 2003, © 2003 Biophysical Society, pp. 2709-2714.

Denton, Kate M. et al., "Differential Neural Control of Glomerular Ultrafiltration," Jan. 30, 2004, Proceedings of the Australian Physiological and Pharmacological Society Symposium: Hormonal, Metabolic and Neural Control of the Kidney, Clinical and Experimental Pharmacology and Physiology (2004), 31, pp. 380-386.

Dev, Nagendu B., Ph.D. et al., "Intravascular Electroporation Markedly Attenuates Neointima Formation After Balloon Injury of the Carotid Artery in the Rat," Journal of Interventional Cardiology, vol. 13, No. 5, 2000, pp. 331-338.

Dev, Nagendu B., Ph.D. et al., "Sustained Local Delivery of Heparin to the Rabbit Arterial Wall With an Electroporation Catheter," May 5, 1998, Catheterization and Cardiovascular Diagnosis 1998, vol. 45, © 1998 Wiley-Liss Inc., pp. 337-345.

DiBona, G., "Neural Control of the Kidney: Functionally Specific Renal Sympathetic Nerve Fibers," Starling Lecture, Am J Physiol Regulatory Integrative Comp Physiol 2000, 279, 2000 The American Physiological Society, pp. R1517-R1524.

Dibona, Gerald F., "Sympathetic Nervous System and the Kidney in Hypertension," Current Opinion in Nephrology and Hypertension 2002, vol. 11, 2002 Lippincott Williams & Wilkins, pp. 197-200.

Dibona, Gerald F. and Linda L. Sawin, "Role of renal nerves in sodium retention of cirrhosis and congestive heart failure," Sep. 27, 1990, Am J Physiol 1991, vol. 260, © 1991 the American Physiological Society, pp. R298-R305.

Dibona, Gerald F. and Ulla C. Kopp, "Neural Control of Renal Function," Physiological Reviews Jan. 1997, vol. 77, No. 1, © 1997 American Physiological Society, pp. 75-197.

Dibona, Gerald F. and Ulla C. Kopp, "Role of the Renal Sympathetic Nerves in Pathophysiological States," Neural Control of Renal Function, vol. 77, pp. 142-197.

Dibona, Gerald F., "Functionally Specific Renal Sympathetic Nerve Fibers: Role in Cardiovascular Regulation," Mar. 6, 2001, American Journal of Hypertension 2001, vol. 14, 2001 American Journal of Hypertension, Ltd. Published by Elsevier Science Inc., pp. 163S-170S.

Dibona, Gerald F., "Nervous Kidney—Interaction Between Renal Sympathetic Nerves and the Renin-Angiotensin System in the Control of Renal Function," Jun. 21, 2000, Hypertension 2000, vol. 36, 2000 American Heart Association, Inc., pp. 1083-1088.

Dibona, Gerald F., "Neural Control of the Kidney-Past, Present, and Future," Nov. 4, 2002, Novartis Lecture, Hypertension 2003, vol. 41, part 2, © 2002 American Heart Association, pp. 621-624.

Dibona, Gerald F., "Peripheral and Central Interactions between the Renin-Angiotensin System and the Renal Sympathetic Nerves in Control of Renal Function," Annals New York Academy of Sciences, pp. 395-406.

Dibona, Gerald F., "Renal Innervation and Denervation: Lessons from Renal Transplantation Reconsidered," Artificial Organs, vol. 11, No. 6, Raven Press Ltd., © 1987 International Society for Artificial Organs, pp. 457-462.

Dibona, Gerald F., "The Sympathetic Nervous System and Hypertension," Dec. 4, 2003, Hypertension Highlights, Hypertension Feb. 2004, vol. 43, © 2004 American Heart Association, pp. 147-150.

Dibona, Gerald F., L.L. Sawin, "Effect of renal denervation on dynamic autoregulation of renal blood flow," Feb. 12, 2004, Am J Physiol Renal Physiol 286, pp. F1209-F1218.

Dibona, Gerald F., Susan Y. Jones, "Dynamic Analysis of Renal Nerve Activity Responses to Baroreceptor Denervation in Hypertensive Rats," Sep. 19, 2000, Hypertension Apr. 2001, © 2001 American Heart Association, pp. 1153-1163.

Dorros, Gerald, M.D., "Renal Artery Stenting State of the Art," presentation, TCT, Washington D.C., Sep. 2003, 27 pages.

Dueck, Ron, M.D., "Noninvasive Cardiac Output Monitoring," The Cardiopulmonary and Critical Care Journal, Chest. vol. 120, sec. 2, Aug. 2001, American College of Chest Physicians 2005, pp. 339-341, 5 pages.

Dunn, Matthew D. et al., "Laparoscopic Nephrectomy in Patients With End-Stage Renal Disease and Autosomal Dominant Polycystic Kidney Disease," Oct. 25, 1999, American Journal of Kidney Diseases Apr. 2000, vol. 35, No. 4, © 2000 National Kidney Foundation, Inc., pp. 720-725.

Durand, D.M., "Electrical Field Effects in Hyperexcitable Neural Tissue: A Review," Radiation Protection Dosimetry, vol. 106, No. 4, 2003, Nuclear Technology Publishing, pp. 325-331.

Erdine, Serap and Alev Arat-Ozkan, "Resistant Hypertension," European Society of Hypertension Scientific Newsletter: Update on Hypertension Management, 2003, vol. 4, No. 15, 2 pages.

Fareed, Jawad, Ph.D. et al., "Some Objective Considerations for the Use of Heparins and Recombinant Hirudin in Percutaneous Transluminal Coronary Angoplasty," Seminars in Thrombosis and Hemostasis 1991, vol. 17, No. 4, © 1991 Thieme Medical Publishers, Inc., pp. 455-470.

Ferguson, D.R et al., "Responses of the pig isolated renal artery to transmural electrical stimulation and drugs," Dec. 7, 1984, Br. J. Pharmac. 1985, vol. 84, © 1985 The Macmillan Press Ltd., pp. 879-882.

Fernandez-Ortiz, Antonio et al., "A New Approach for Local Intravascular Drug Delivery—Iontophoretic Balloon,," Intravascular Iontophoretic Local Delivery, Circulation, vol. 89, No. 4, Apr. 1994, pp. 1518-1522.

Fields, Larry E. et al, "The Burden of Adult Hypertension in the United States 1999 to 2000—A Rising Tide," May 18, 2004, © 2004 the American Heart Association, Hypertension Oct. 2004, pp. 1-7.

Freeman, Scott A. et al., "Theory of Electroporation of Planar Bilayer Membranes: Predictions of the Aqueous Area, Change in Capacitance, and Pore-Pore Separation," Feb. 23, 1994, Biophysical Journal, Jul. 1994, vol. 67, © 1994 by the Biophysical Society, pp. 42-56.

Fukuoka, Yuko et al., "Imaging of neural conduction block by neuromagnetic recording," Oct. 16, 2002, Clinical Neurophysiology 2002, vol. 113, © 2002 Elsevier Science Ireland Ltd., pp. 1985-1992.

Gami, Apoor S., M.D. and Vesna D. Garovic, M.D., "Contrast Nephropathy After Coronary Angiography," Mayo Clin Proc. 2004, vol. 79, 2004 Mayo Foundation for Medical Education and Research, pp. 211-219.

Gattone II, Vincent H. et al., "Contribution of Renal Innervation to Hypertension in Polycystic Kidney Disease in the Rat," University of Chicago Section of Urology, 16 pages.

Gaylor, D.C. et al., "Significance of Cell Size and Tissue Structure in Electrical Trauma," Jan. 26, 1998, J. Theor. Biol. 1988, vol. 133, © 1988 Academic Press Limited, pp. 223-237.

Gehl, Julie et al., "In vivo electroporation of skeletal muscle: threshold, efficacy and relation to electric field distribution," Biochimica et Biophysica Acta, 1428, 1999, Elsevier Science B.V. 1999, pp. 233-240.

Ghoname, El-sayed A. et al., "Percutaneous electrical nerve stimulation: an alternative to TENS in the management of sciatica," Apr. 26, 1999, Pain 1999, vol. 83, © 1999 International Association for the Study of Pain / Published by Elsevier Science B.V., pp. 193-199.

Gimple, M.D., Lawrence et al., "Effect of Chronic Subcutaneous or Intramural Administration of Heparin on Femoral Artery Restenosis After Balloon Angioplasty in Hypercholesterolemic Rabbits" Laboratory Investigation, Circulation, vol. 86, No. 5, Nov. 1992, pp. 1536-1546.

Goldberger, Jeffrey J. et al., "New technique for vagal nerve stimulation," Jun. 2, 1999, Journal of Neuroscience Methods 91, © 1999 Elsevier Science B.V., pp. 109-114.

Gorbunov, F.E. et al., "The Use of Pulsed and Continuous Short Wave Diathermy (Electric Field) in Medical Rehabilitation of the Patients with Guillan-Barre Syndrome and Other Peripheral Myelinopathies," May 6, 1994, 5 pages (most of article in Russian language).

Greenwell, T.J. et al., "The outcome of renal denervation for managing loin pain haematuria syndrome," Oct. 30, 2003, Institute of Urology and Nephrology, London, UK, © 2004 BJU International, 4 pages.

Gruberg, Luis, M.D. et al., "The Prognostic Implications of Further Renal Function Deterioration Within 48 h of Interventional Coronary Procedures in Patients with Pre-existent Chronic Renal Insufficiency," Jun. 19, 2000, Journal of the American College of Cardiology 2000, vol. 36, No. 5, © 2000 by the American College of Cardiology, pp. 1542-1548.

Hajjar, Ihab, M.D., M.S. and Theodore A. Kotchen, M.D., "Trends in Prevalence, Awareness, Treatment, and Control of Hypertension in the United States, 1988-2000," JAMA, Jul. 9, 2003, vol. 290, No. 2, pp. 199-206.

Hamza, M.D., Mohamed A. et al., "Effect of the Duration of Electrical Stimulation on the Analgesic Response in Patients with Low Back Pain," Anesthesiology, vol. 91, No. 6, Dec. 1999, © 1999 American Society of Anesthesiologists, Inc., pp. 1622-1627.

Han, Hyo-Kyung and Gordon L. Amidon, "Targeted Prodrug Design to Optimize Drug Delivery," Mar. 21, 2000, AAPS Pharmsci. 2000, vol. 2, No. 1, article 6, pp. 1-11.

Heida, Tjitske et al., "Investigating Membrane Breakdown of Neuronal Cells Exposed to Nonuniform Electric Fields by Finite-Element Modeling and Experiments," May 9, 2002. IEEE Transactions on Biomedical Engineering, vol. 49, No. 10, Oct. 2002, © 2002 IEEE, pp. 1195-1203.

Higuchi, Yoshinori, M.D., Ph.D. et al., "Exposure of the Dorsal Root Ganglion in Rats to Pulsed Radiofrequency Currents Activates Dorsal Horn Lamina I and II Neurons," Dec. 4, 2001, Experimental Studies, Neurosurgery, vol. 50, No. 4, Apr. 2002, pp. 850-856.

Hildebrand, Keith R., D.V.M., Ph.D. et al., "Stability, Compatibility, and Safety of Intrathecal Bupivacaine Administered Chronically via an Implantable Delivery System," May 18, 2001, The Clinical Journal of Pain, vol. 17, No. 3, © 2001 Lippincott Williams & Wilkins Inc., pp. 239-244.

Hing, Esther, M.P.H. and Kimberly Middleton, B.S.N., M.P.H., "National Hospital Ambulatory Medical Care Survey: 2001 Outpatient Department Summary," Aug. 5, 2003, Advance Data From Vital and Health Statistics, No. 338, CDC, 32 pages.

Hopp, Francis A. and Jeanne L. Seagard, "Respiratory Responses to Selective Blockade of Carotid Sinus Baroreceptors in the Dog," Jun. 22, 2005, Am J Physiol Regul Integr Comp Physiol 1998, vol. 275, 2005 American Physiological Society, pp. R10-R18.

Horwich, Tamara, M.D., "New Advances in the Diagnosis and Management of Acute Decompensated Heart Failure," the Heart.org Satellite program, Rapid Review, CME Symposium presented on Nov. 8, 2004 at the Sheraton New Orleans Hotel, 4 pages.

Huang, Wann-Chu et al. "Renal Denervation Prevents and Reverses Hyperinsulinemia-Induced Hypertension in Rats," Mar. 25, 1998, Hypertension 1998, vol. 32, 1998 American Heart Association, Inc., pp. 249-254.

Huang, Yifei et al., "Remodeling of the chronic severely failing ischemic sheep heart after coronary microembolization: functional, energetic, structural, and cellular responses," Jan. 8, 2004, Am J Physiol. 2004, vol. 286, © 2004 the American Physiological Society, pp. H2141-H2150.

Hughes, Gordon B., M.D. et al., "A Comparative Study of Neuropathologic Changes Following Pulsed and Direct Current Stimulation of the Mouse Sciatic Nerve," Jun. 27, 1980, American Journal of Otolaryngology, Nov. 1980, vol. 1, No. 5, pp. 378-384.

Israili, ZH., "Clinical pharmacokinetics of angiotensin II (AT) receptor blockers in hypertension," Journal of Human Hypertension 2000, Macmillan Publishers Ltd., vol. 14, pp. S73-S86.

Janssen, Ben J.A. et al., "Effects of complete renal denervation and selective afferent renal denervation on the hypertension induced by intrarenal norepinephrine infusion on conscious rats," Jan. 4, 1989, Journal of Hypertension 1989, vol. 7, No. 6, © 1989 Current Science Ltd., pp. 447-455.

Johansson, Bjorn, "Electrical Membrane Breakdown, A Possible Mediator of the Actions of Electroconvulsive Therapy," Medical Hypotheses 1987, vol. 24, © 1987 Longman Group UK Ltd., pp. 313-324.

Jorgensen, William A. et al., "Electrochemical Therapy of Pelvic Pain: Effects of Pulsed Electromagnetic Fields (PEMF) on Tissue Trauma," Eur. J. Surg. 1994, vol. 160, Suppl. 574, © 1994 Scandinavian University Press, pp. 83-86.

Joshi, R.P. et al., "Improved energy model for membrane electroporation in biological cells subjected to electical pulses," Apr. 9, 2002, Physical Review E, vol. 65, 041920-1, © 2002 The American Physical Society, 8 pages.

Joshi, R.P. et al., "Self-consistent simulations of elctroporation dynamics in biological cells subjected to ultrashort electrical pulses," Jun. 21, 2001, Physical Review E, vol. 64, 011913, © 2001The American Physical Society, pp. 1-10.

Joshi, R.P., K.H. Schoenbach, "Mechanism for membrane electroporation irreversibility under high-intensity, ultrashort electrical pulse conditions," Nov. 11, 2002, Physical Review 2002, E 66, © 2002 The American Physical Society, pp. 052901-1-052901-4.

Kanduser, Masa et al., "Effect of surfactant polyoxyethylene glycol $(C_{12}E_8)$ on electroporation of cell line DC3F," Aug. 20, 2002, Colloids and Surfaces A: Physiochem. Eng. Aspects 2003, vol. 214, © 2002 Elsevier Science B.V., pp. 205-217.

Katholi, Richard E., "Renal nerves in the pathogenesis of hypertension in experimental animals and humans," Am J Physiol., vol. 245, © 1983 the American Physiological Society, pp. F1-F14.

Kelleher, Catherine L. et al., "Characteristics of Hypertension in Young Adults With Autosomal Dominant Polycystic Kidney Disease Compared With the General U.S. Population," Jun. 9, 2004, American Journal of Hypertension 2004, pp. 1029-1034.

King, Ronald W.P., "Nerves in a Human Body Exposed to Low-Frequency Electromagnetic Fields," Jun. 7, 1999, IEEE Transactions on Biomedical Engineering Dec. 1999, vol. 46, No. 12, © 1999 IEEE, pp. 1426-1431.

Kinney, Brian M., M.D., "High-Tech Healing—The evolution of therapeutic electromagnetic fields in plastic surgery," Plastic Surgery Products, Jun. 2004, pp. 32-36, 3 pages.

Kok, R.J. et al., "Specific Delivery of Captopril to the Kidney with the Prodrug Captopril-Lysozyme," Aug. 16, 1998, The Journal of Pharmacology and Experimental Therapeutics, vol. 288, No. 1, © 1999 by the American Society for Pharmacology and Experimental Therapeutics, pp. 281-285.

Kon, Valentina, "Neural Control of Renal Circulation," Miner Electrolyte Metab 1989, vol. 15, © 1989 S. Karger AG, pp. 33-43.

Koyama, Shozo et al., "Relative Contribution of Renal Nerve and Adrenal Gland to Renal Vascular Tone During Prolonged Canine Hemorrhagic Hypotension," Sep. 24, 1992, Circulatory Shock 1993, vol. 39, © 1993 Wiley-Liss Inc., pp. 269-274.

Kozak, Lola Jean, Ph.D. et al., "National Hospital Discharge Survey: 2001 Annual Summary with Detailed Diagnosis and Procedure Data," Vital Health Statistics, Series 13, No. 156, Jun. 2004, CDC, 206 pages.

Lafayette, Richard A., M.D., "How Does Knocking Out Angiotensin II Activity Reduce Renal injury in Mice?" Jun. 14, 1999, Journal Club, American Journal of Kidney Diseases, vol. 35, No. 1, Jan. 2000, © 2000 National Kidney Foundation Inc., pp. 166-172.

Lavie, Peretz, Ph.D. and Victor Hoffstein, M.D., "Sleep Apnea Syndrome: A Possible Contributing Factor to Resistant Hypertension," Jun. 2001, Sleep 2001, vol. 24, No. 6, pp. 721-725.

Lee, Raphael C. and Jurgen Hannig, "Membrane Biology and Biophysics," Chapter 25, Surgical Research, © 2001 Academic Press, pp. 297-305.

Lee, Raphael C. et al., "Biophysical Injury Mechanisms in Electrical Shock Trauma," Annu. Rev. Biomed. Eng., 2000, vol. 2, Copyright © 2000 by Annual Reviews, pp. 477-509.

Lee, Raphael C. et al., "Clinical Sequelae Manifested in Electrical Shock Survivors," Presentation by the Electrical Trauma Research Program, The University of Chicago, 37 pages.

Lee, Raphael C., M.D., Sc.D. and Michael S. Kolodney, S.B., "Electrical Injury Mechanisms: Electrical Breakdown of Cell Membranes," Oct. 1, 1986, Plastic and Reconstructive Surgery Nov. 1987, vol. 80, No. 5, pp. 672-679.

Ligtenberg, Gerry, M.D. et al., "Reduction of Sympathetic Hyperactivity by Enalapril in Patients with Chronic Renal Failure," Apr. 29, 1999, New England Journal of Medicine 1999, vol. 340, No. 17, © 1999 Massachusetts Medical Society, pp. 1321-1328.

Lin, Vernon W. H. et al, "High intensity magnetic stimulation over the lumbosacral spine evokes antinociception in rats," Apr. 16, 2002, Clinical Neurophysiology, vol. 113, © 2002 Elsevier Science Ireland Ltd., pp. 1006-1012.

Lipfert, Peter, M.D. et al., "Tachyphylaxis to Local Anesthetics Does Not Result From Reduced Drug Effectiveness at the Nerve Itself," Aug. 3, 1988, Anesthesiology 1989, vol. 70, pp. 71-75.

Lohmeier Thomas E. et al, "Baroreflexes prevent neurally induced sodium retention in angiotensin hypertension," Am. J. Physiol. Regulatory Integrative Comp. Physiol., vol. 279, © 2000 the American Physiological Society, pp. R1437-R1448.

Lohmeier, Thomas E. and Drew A. Hildebrandt, "Renal Nerves Promote Sodium Excretion in Angiotensin-Induced Hypertension," Oct. 20, 1997, Hypertension 1998, vol. 31, Part 2, © 1998 American Heart Association, Inc., pp. 429-434.

Lohmeier, Thomas E. et al., "Prolonged Activation of the Baroflex Produces Sustained Hypotension," Harry Goldblatt Award, Nov. 26, 2003, Hypertension 2004, vol. 43, part 2, © 2004 American Heart Association, Inc., pp. 306-311.

Lohmeier, Thomas E. et al., "Renal Nerves Promote Sodium Excretion During Long-Term Increases in Salt Intake," Oct. 23, 1998, Hypertension 1999, vol. 33, part 2, © 1999 American Heart Association, pp. 487-492.

Lohmeier, Thomas E. et al., "Sustained influence of the renal nerves to attenuate sodium retention in angiotensin hypertension," Apr. 13, 2001, Am J Physiol Regulatory Integrative Comp. Physiol., vol. 281, © 2001 the American Physiological Society, pp. R434-R443.

Lohmeier, Thomas E., "Interactions Between Angiotensin II and Baroreflexes in Long-Term Regulation of Renal Sympathetic Nerve Activity," Circulation Research, Jun. 27, 2003, © 2003 American Heart Association Inc., pp. 1282-1284.

"Market for infusion pumps grows with an aging population," NWL 97-01, The BBI Newsletter, vol. 20, No. 2, Feb. 1, 1997, American Health Consultants Inc., 6 pages.

"PHCL 762 Pharmacology of the Autonomic Nervous System," Chapter 2 and 6.8 in Mosby, http://www.kumc.edu/research/medicine/pharmacology/CAI/phcl762.html, last accessed Aug. 24, 2004, 14 pages.

"Programmable Infusion System," Pumps and Pump Selection, Medtronic Pain Therapies, Medtronic, Inc. Sep. 5, 2001, 2 pages.

"Pulmonary Concepts in Critical Care Breath Sounds," http://rnbob.tripod.com/breath.htm, last accessed Aug. 23, 2004, 5 pages.

"Pulmonary Function Testing," http://jan.ucc.nau.edu/~daa/lecture/pft.htm, last accessed Aug. 23, 2004, 8 pages.

"Renal Parenchymal Disease," Ch. 26, 5th Edition Heart Disease, A Textbook of Cardiovascular Medicine vol. 2, Edited by Eugene Braunwald, WB Saunders Company, pp. 824-825.

"Sensorcaine-MPF Spinal Injection," informational document, AstraZeneca 2001, 2 pages.

"Summary," Critical Reviews in Biomedical Engineering, vol. 17, Issue 5, 1989, pp. 515-529.

"The Antihypertensive and Lipid-Lowering Treatment to Prevent Heart Attack Trial," ALLHAT Research Group, JAMA 2002, vol. 288, pp. 2981-2997.

Luff, S.E. et al., "Two types of sympathetic axon innervating the juxtaglomerular arterioles of the rabbit and rat kidney differ structurally from those supplying other arteries," May 1, 1991, Journal of Neurocytology 1991, vol. 20, © 1991 Chapman and Hall Ltd., pp. 781-795.

Lundborg, C. et al., "Clinical experience using intrathecal (IT) bupivacaine infusion in three patients with complex regional pain syndrome type I (CRPS-I)," Acta Aneaesthesiol. Scand. 1999, vol. 43, pp. 667-678.

MacArthur, Dr. Alison, "Spinal Anesthesia and Severe Gestational Hypertension," presentation at Mount Sinai Hospital, 25 pages.

Maeder, Micha, M.D. et al., "Contrast Nephropathy: Review Focusing on Prevention," Jun. 22, 2004, Journal of the American College of Cardiology Nov. 2, 2004, vol. 44, No. 9, © 2004 by the American College of Cardiology Foundation, pp. 1763-1771.

Malpas, Simon C., "What sets the long-term level of sympathetic nerve activity: is there a role for arterial baroreceptors?" Invited Review, Am J Physiol Regul. Integr. Comp. Physiol. 2004, vol. 286, © 2004 the American Physiological Society, pp. R1-R12.

Marenzi, Giancarlo, M.D. et al., "The Prevention of Radiocontrast-Agent-Induced Nephropathy by Hemofiltration," New England Journal of Medicine, Oct. 2, 2003, vol. 349 (14), © 2003 Massachusetts Medical Society, pp. 1333-1340.

Martin, Jason B. et al., "Gene Transfer to Intact Mesenteric Arteries by Electroporation," Mar. 27, 2000, Journal of Vascular Research 2000, vol. 37, 2000 S. Karger AG, Basel, pp. 372-380.

McCreery, Douglas B. et al., "Charge Density and Charge Per Phase as Cofactors in Neural Injury Induced by Electrical Stimulation," IEEE Transactions on Biomedical Engineering, vol. 17, No. 10, Oct. 1990, pp. 996-1000.

McCullough, Peter A., M.D., MPH et al., "Acute Renal Failure after Coronary Intervention: Incidence, Risk Factors and Relationship to Mortality," Apr. 14, 1997, Am J Med. 1997, vol. 103, 1997 Excerpta Medica, Inc., pp. 368-375.

McMurray, John J.V., M.D. and Eileen O'Meara, M.D., "Treatment of Heart Failure with Spironolactone-Trial and Tribulations," Aug. 5, 2004, New England Journal of Medicine, vol. 351, No. 6, © 2004 Massachusetts Medical Society, pp. 526-528.

McRobbie, D. and M.A. Foster, "Thresholds for biological effects of time-varying magnetic fields," Dec. 16, 1983, Clin. Phys. Physiol. Meas. 1984, vol. 5, No. 2, © 1984, The Institute of Physics, pp. 67-78.

Medtronic Neurostimulation Systems, "Expanding the Array of Pain Control Solutions," informational pamphlet, 1999 Medtronic, Inc., 6 pages.

Medtronic, "Spinal Cord Stimulation," Patient Management Guidelines for Clinicians, Medtronic, Inc. 1999, 115 pages.

Medtronic, "SynchroMed Infusion System—Clinical Reference Guide for Pain Therapy," Medtronic, Inc. 1998, 198 pages.

Mess, Sarah A., M.D. et al., "Implantable Baclofen Pump as an Adjuvent in Treatment of Pressure Sores," Mar. 1, 2003, Annals of Plastic Surgery, vol. 51, No. 5, Nov. 2003, © 2003 Lippincott Williams & Wilkins, pp. 465-467.

Mihran, Richard T. et al., "Temporally-Specific Modification of Myelinated Axon Excitability in Vitro Following A Single Ultrasound Pulse," Sep. 25, 1989, Ultrasound in Med.& Biol. 1990, vol. 16, No. 3, pp. 297-309.

Miklavcic, D. et al, "A Validated Model of in Vivo Electric Field Distribution in Tissues for Electrochemotherapy and for DNA Electrotransfer for Gene Therapy," Biochimica et Biophysica Acta, 1523, 2000, pp. 73-83, www.elsevier.com/locate/bba.

Mitchell, G.A.G., "The Nerve Supply of the Kidneys," Aug. 20, 1949, Acta Anatomica, vol. 10, Fasc. 1/2, 1950, pp. 1-37.

Moss, Nicholas G., "Renal function and renal afferent and efferent nerve activity," Am J Physiol 1982, vol. 243, © 1982, the American Physiological Society, pp. F425-F433.

Munglani, Rajesh, "The longer term effect of pulsed radiofrequency for neuropathic pain," Jun. 8, 1998, Pain, vol. 80, © 1999 International Association for the Study of Pain, Published by Elsevier Science B.V., pp. 437-439.

Naropin (ropivacaine HCI) injection, Rx only description, AstraZeneca 2001, 3 pages.

National High Blood Pressure Education Program, "1995 Update of the Working Group Reports on Chronic Renal Failure and Renovascular Hypertension," presentation, 13 pages.

National Kidney Foundation, "Are You At Increased Risk for Chronic Kidney Disease?" © 2002 National Kidney Foundation, Inc., 14 pages.

Nelson, Lawrence D. And Jeffrey L Osborn, "Neurogenic Control of Renal Function in Response to Graded Nonhypotensive Hemorrhage in Conscious Dogs," Sep. 13, 1992, Am. J. Physiol. 264, 1993, American Physiological Society 1993, pp. R661-R667.

Nikolsky, Eugenia, M.D. et al., "Radiocontrast Nephropathy: Identifying the High-Risk Patient and the Implications of Exacerbating Renal Function," Rev Cardiovasc Med. 2003, vol. 4, Supp. 1, © 2003 MedReviews, LLC, pp. S7-S14.

Nozawa, Takashi et al., "Effects of Long Term Renal Sympathetic Denervation on Heart Failure After Myocardial Infarction in Rats," Sep. 22, 2001, Heart Vessels 2002, vol. 16, Springer-Verlag 2002, pp. 51-56.

Palmer, Biff F., M.D., "Managing Hyperkalemia Caused by Inhibitors of the Renin-Angiotensin-Aldosterone System," Aug. 5, 2004, The New England Journal of Medicine 2004, vol. 351, No. 6, © 2004 Massachusetts Medical Society, pp. 585-592.

Peacock, J.M. and R. Orchardson, "Action potential conduction block of nerves in vitro by potassium citrate, potassium tartrate and potassium oxalate," May 6, 1998, Journal of Clinical Periodontology, © 1999 Munksgaard, vol. 26, pp. 33-37.

Pettersson, A. et al., "Renal interaction between sympathetic activity and ANP in rats with chronic ischaemic heart failure," Nov. 25, 1998, Acta Physiol. Scand. 1989, vol. 135, pp. 487-492.

Pliquett, U., "Joule heating during solid tissue electroporation," Oct. 22, 2002, Medical & Biological Engineering and Computing 2003, vol. 41, pp. 215-219.

Podhajsky, R. J., et al. "The Histologic Effects of Pulsed and Continuous Radiofrequency Lesions at 42° C to Rat Dorsal Root Ganglion and Sciatic Nerve," Spine, vol. 30, No. 9, 2005, Lippincott Williams & Wilkins Inc., pp. 1008-1013.

Popovic, Jennifer .R. and Margaret J. Hall," 1999 National Hospital Discharge Survey," Advance Data, No. 319, CDC, pp. 1-17 & 20.

Practice Guidelines Writing Committee and ESH/ESC Hypertension Guidelines Committee, "Practice Guidelines For Primary Care Physicians: 2003 ESH/ESC Hypertension Guidelines," Published in Journal of Hypertension 2003, vol. 21, No. 10: 1011-1053, © 2003 European Society of Hypertension, pp. 1779-1786.

Pucihar, Gorazd et al., "The influence of medium conductivity on electropermeabilization and survival of cells in vitro," May 31, 2001, Bioelectrochemistry, vol. 54, 2001, Elsevier Science B.V. 2001, pp. 107-115.

Raji, A. R. M. and R. E. M. Bowden, "Effects of High-Peak Pulsed Electromagnetic Field on the Degeneration and Regeneration of the Common Peroneal Nerve in Rats," The Journal of Bone and Joint Surgery Aug. 1983, vol. 65-B, No. 4, © 1983 British Editorial Society of Bone and Joint Surgery, pp. 478-492.

Ram, C. Venkata S., M.D., "Understanding refractory hypertension," May 15, 2004, Patient Care May 2004, vol. 38, pp. 12-16, 7 pages from http://www.patientcareonline.com/patcare/content/printContentPopup.jsp?id=108324.

Ravalia, A. et al., "Tachyphylaxis and epidural anesthesia," Edgware General Hospital, Correspondence, p. 529.

Ribstein, Jean and Michael H. Humphreys, "Renal nerves and cation excretion after acute reduction in functioning renal mass in the rat," Sep. 22, 1983, Am J Physiol, vol. 246, © 1984 the American Physiological Society, pp. F260-F265.

Richebe, Philippe, M.D. et al., "Immediate Early Genes after Pulsed Radiofrequency Treatment: Neurobiology in Need of Clinical Trials," Oct. 13, 2004, Anesthesiology Jan. 2005, vol. 102, No. 1, © 2004 American Society of Anesthesiologists, Inc. Lippincott Williams & Wilkins, Inc., pp. 1-3.

Rihal, Charanjit S. et al., "Incidence and Prognostic Importance of Acute Renal Failure After Percutaneous Coronary Intervention," Mar. 6, 2002, Circulation May 14, 2002, vol. 10, © 2002 American Heart Association, Inc., pp. 2259-2264.

Rosen, S.M. et al., "Relationship of Vascular Reactivity to Plasma Renin Concentration in Patients with Terminal Renal Failure," Proc. Dialysis Transplant Forum 1974, pp. 45-47.

Roth, Bradley J. and Peter J. Basser, "A Model of the Stimulation of a Nerve Fiber by Electromagnetic Induction," IEEE Transactions on Biomedical Engineering, vol. 37, No. 6, Jun. 1990, pp. 588-597.

Rudin, Asa, M.D. et al., "Postoperative Epidural or Intravenous Analgesia after Major Abdominal or Thoraco-Abdominal Surgery," The Journal of the American Society of Anesthesiologists, Inc., Anesthesiology 2001, vol. 95, A-970, 1 page.

Rudnick, Michael R. et al., "Contrast-induced nephropathy: How it develops, how to prevent it," Cleveland Clinic Journal of Medicine Jan. 2006, vol. 73, No. 1, pp. 75-87.

Rump, L.C., "The Role of Sympathetic Nervous Activity in Chronic Renal Failure," J Clinical Basic Cardiology 2001, vol. 4, pp. 179-182.

Ruohonen, Jarmo et al., "Modeling Peripheral Nerve Stimulation Using Magnetic Fields," Journal of the Peripheral Nervous System 1997, vol. 2, No. 1, © 1997 Woodland Publications, pp. 17-29.

Scheiner, Avram, Ph.D., "The design, development and implementation of electrodes used for functional electrial stimulation," Thesis paper, Case Western Reserve University, May 1992, 220 page.

Schoenbach, Karl H. et al., "Intracellular Effect of Ultrashort Electrical Pulses," Dec. 26, 2000, Bioelectromagnetics 2001, vol. 22, © 2001 Wiley-Liss Inc., pp. 440-448.

Schrier, Robert et al., "Cardiac and Renal Effects of Standard Versus Rigorous Blood Pressure Control in Autosomal-Dominant Polycystic Kidney Disease," Mar. 23, 2002, Journal of the American Society of Nephrology, © 2002 American Society of Nephrology, pp. 1733-1739.

Scremin, Oscar U., M.D., Ph.D. and Danel P. Holschneider, M.D., "31. & 32. An Implantable Bolus Infusion Pump for the Neurosciences," FRP, 04-05, 3 pages.

Shu-Qing, Liu et al., "Old spinal cord injury treated by pulsed electric stimulation," General Hospital of Beijing Command, Beijing, 5 pages (full article in Chinese; abstract on last page).

Shupak, Naomi M., "Therapeutic Uses of Pulsed Magnetic-Field Exposure: A Review," Radio Science Bulletin Dec. 2003, No. 307, pp. 9-32.

Simpson, B. et al, "Implantable Spinal Infusion Devices for Chronic Pain and Spasticity: An Accelerated Systematic Review," ASERNIP-S Report No. 42, May 2003, 56 pages.

Sisken, B.F. et al., "229.17 Influence of Non-Thermal Pulsed Radiofrequency Fields (PRF) on Neurite Outgrowth," Society for Neuroscience, vol. 21, 1995, 2 pages.

Skeie, B. et al., "Effect of chronic bupivacaine infusion on seizure threshold to bupivacaine," Dec. 28, 1986, Acta Anaesthesiol. Scand. 1987, vol. 31, pp. 423-425.

Skopec, M., "A Primer on Medical Device Interactions with Magnetic Resonance Imaging Systems," Feb. 4, 1997, CDRH Magnetic Resonance Working Group, U.S. Department of Health and Human Services, Food and Drug Administration, Center for Devices and Radiological Health, Updated May 23, 1997, 17 pages, http://www.fde.gov/cdrh/ode/primerf6.html, (last accessed Jan. 23, 2006.

Slappendel, Robert et al., "The efficacy of radiofrequency lesioning of the cervical spinal dorsal root ganglion in a double blinded randomized study," Jun. 26, 1997, Pain, vol. 73, © 1997 International Association of the Study of Pain, Elsevier Science B.V., pp. 159-163.

Sluijter, M.D., Ph.D., "Pulsed Radiofrequency," May 17, 2005, Anesthesiology Dec. 2005, vol. 103, No. 6, © 2005 American Society of Anesthesiologists, Inc. Lippincott Williams & Wilkins, Inc., pp. 1313-1314.

Sluijter, M.D., Ph.D., "Radiofrequency Part 1: the Lumbosacral Region," Chapter 1 Mechanisms of Chronic Pain and part of Chapter 2 Spinal Pain, © 2001 FlivoPress SA, Meggen (LU), Switzerland, pp. 1-26.

Sluijter, M.D., Ph.D., "Radiofrequency Part 2: Thoracic and Cervical Region, Headache and Facial Pain," various pages from, FlivoPress SA, Meggen (LU), Switzerland, 13 pages.

Sluijter, M.D., Ph.D., "The Role of Radiofrequency in Failed Back Surgery Patients," Current Review of Pain 2000, vol. 4, © 2000 by Current Science Inc., pp. 49-53.

Souza, D.R.B. et al., "Chronic experimental myocardial infarction produces antinatriuresis by a renal nerve-dependent mechanism," Oct. 14, 2003, Brazilian Journal of Medical and Biological Research 2004, vol. 37, pp. 285-293.

Standl, Thomas, M.D., et al, "Patient-controlled epidural analgesia reduces analgesic requirements compared to continuous epidural infusion after major abdominal surgery," Aug. 29, 2002, Canada Journal of Anesthesia 2003, vol. 50, No. 3, pp. 258-264.

Stone, Gregg W., M.D. et al., "Fenoldopam Mesylate for the Prevention of Contrast-Induced Nephropathy," JAMA Nov. 5, 2003, vol. 290, No. 17, © 2003 American Medical Association, pp. 2284-2291.

Sung, Duk Hyun, M.D. et al., "Phenol Block of Peripheral Nerve Conduction: Titrating for Optimum Effect," Jun. 27, 2000, Arch. Phys. Med. Rehabil., vol. 82, May 2001, pp. 671-676.

Taler, Sandra J. et al., "Resistant Hypertension, Comparing Hemodynamic Management to Specialist Care," Mar. 12, 2002, Hypertension 2002, vol. 39, 2002 American Heart Association, Inc., pp. 982-988.

Tay, Victoria KM et al., "Computed tomography fluoroscopy-guided chemical lumbar sympathectomy: Simple, safe and effective," Oct. 31, 2001, Diagnositc Radiology, Australasian Radiology 2002, vol. 46, pp. 163-166.

Thompson, Gregory W. et al, "Bradycardia Induced by Intravascular Versus Direct Stimulation of the Vagus Nerve," Aug. 24, 1997, The Society of Thoracic Surgeons 1998, pp. 637-642.

Thrasher, Terry N., "Unloading arterial baroreceptors causes neurogenic hypertension," Dec. 4, 2001, Am J Physiol Regulatory Integrative Comp. Physiol., vol. 282, © 2002 the American Physiological Society, pp. R1044-R1053.

Tokuno, Hajime A. et al., "Local anesthetic effects of cocaethylene and isopropylcocaine on rat peripheral nerves," Oct. 7, 2003, Brain Research 996, 2004, © 2003 Elsevier B.V., pp. 159-167.

Trapani, Angelo J. et al., "Neurohumoral interactions in conscious dehydrated rabbit," Am J Physiol 1988, Vol. 254, © 1988 the American Physiological Society, pp. R338-R347.

Trock, David H. et al., "The Effect of Pulsed Electromagnetic Fields in the Treatment of Osteoarthritis of the Knee and Cervical Spine. Report of Randomized, Double Blind, Placebo Controlled Trials," Mar. 22, 1994, The Journal of Rheumatology 1994, vol. 21, pp. 1903-1911.

Troiano, Gregory C. et al., "The Reduction in Electroporation Voltages by the Addition of a Surfactant to Planar Lipid Bilayers," May 12, 1998, Biophysical Journal, vol. 75, Aug. 1998, © the Biophysical Society, pp. 880-888.

Trumble, Dennis R., and James A. Magovern, "Comparison of Dog and Pig Models for Testing Substernal Cardiac Compression Devices," Nov. 2003, ASAIO Journal 2004, pp. 188-192.

Tsai, E., "Intrathecal drug delivery for pain indications, technique, results," Pain Lecture presentation, Jun. 8, 2001, 31 pages.

Uematsu, Toshihiko, M.D., Ph.D., F.I.C.A. et al., "Extrinsic Innervation of the Canine Superior Vena Cava, Pulmonary, Portal and Renal Veins," Angiology-Journal of Vascular Diseases, Aug. 1984, pp. 486-493.

United States Renal Data System, "USRDS 2003 Annual Data Report: Atlas of End-Stage Renal Disease in the United States," National Institutes of Health, National Institute of Diabetes and Digestive and Kidney Diseases, 2003, 593 pages.

Upadhyay, Pramod, "Electroporation of the skin to deliver antigen by using a piezo ceramic gas igniter," Jan. 27, 2001, International Journal of Pharmaceutics, vol. 217, © 2001 Elsevier Science B.V., pp. 249-253.

Valente, John F. et al., "Laparoscopic renal denervation for intractable ADPKD-related pain," Aug. 24, 2000, Nephrology Dialysis Transplantation 2001, vol. 16, European Renal Association-European Dialysis and Transplant Association, p. 160.

Van Antwerp, Bill and Poonam Gulati., "Protein Delivery from Mechanical Devices Challenges and Opportunities," Medtronic Presentation, 19 pages.

Velazquez, Eric J., "An international perspective on heart failure and left ventricular systolic dysfunction complicating myocardial infarction: the Valiant registry," Aug. 5, 2004, European Heart Journal, vol. 25, © 2004 Elsevier Ltd., pp. 1911-1919.

Velez-Roa, Sonia, M.D., et al., "Peripheral Sympathetic Control During Dobutamine Infusion: Effects of Aging and Heart Failure," Jul. 7, 2003, Journal of the American College of Cardiology 2003, vol. 42, No. 9, © 2003 American College of Cardiology Foundation, pp. 1605-1610.

Vigilance, Deon W. et al., "A Novel Approach to Increase Total Urine Output in Acute Heart Failure: Unilateral Renal nerve Blockade," RNB Abstract AHA, 2 pages.

Villarreal, Daniel et al., "Effects of renal denervation on postprandial sodium excretion in experimental heart failure," Oct. 29, 1993, Am J Physiol 266, 1994, pp. R1599-R1604.

Villarreal, Daniel et al., "Neurohumoral modulators and sodium balance in experimental heart failure," Nov. 6, 1992, Am J Physiol, vol. 264, 1993, pp. H1187-H1193.

Wagner, C.D. et al, "Very low frequency oscillations in arterial blood pressure after autonomic blockade in conscious dogs," Feb. 5, 1997, Am J Physiol Regul Integr Comp Physiol 1997, vol. 272, © 1997 the American Physiological Society, pp. 2034-2039.

Wald, Jan D. Ph.D. et al., "Cardiology Update 2003," Sep. 11, 2003, © 2003 AG Edwards, 120 pages.

Wang, Xi et al., "Alterations of adenylyl cyclase and G proteins in aortocaval shut-induced heart failure," Jul. 2004, Am J Physiol Heart Circ Physiol., vol. 287, © 2004 the American Physiological Society, pp. H118-H125.

Weaver, James C., "Chapter 1: Electroporation Theory, Concepts and Mechanisms," Methods in Molecular Biology, vol. 55, Plant Cell Electroporation and Electrofusion Protocols, Edited by J.A. Nickoloff, © Humana Press Inc., pp. 3-28.

Weaver, James C., "Electroporation: A General Phenomenon for Manipulating Cells and Tissues," Oct. 22, 1992, Journal of Cellular Biochemistry, vol. 51, © 1993 Wiley-Liss, Inc., pp. 426-435.

Weiner, Richard L., M.D., "Peripheral nerve neurostimulation," Neurosurgery Clinics of North America 2003, vol. 14, © 2003 Elsevier Inc., pp. 401-408.

Weisbord, Steven D., M.D. and Paul M. Palevsky, M.D., "Radiocontrast-Induced Acute Renal Failure," Jul. 10, 2004, Journal of Intensive Care Medicine 2005, vol. 20 (2), © 2005 Sage Publications, pp. 63-75.

Wilson, D.H. et al., "The Effects of Pulsed Electromagnetic Energy on Peripheral Nerve Regeneration," Annals New York Academy of Sciences, pp. 575-585.

Wolinsky, Harvey, M.D., Ph.D. and Swan N. Thung, M.D., "Use of a Perforated Balloon Catheter to Deliver Concentrated Heparin Into the Wall of the Normal Canine Artery," Aug. 30, 1989, JACC 1990, vol. 15, © 1990 The American College of Cardiology, pp. 475-481.

Wyss, J.Michael et al., "Neuronal control of the kidney: Contribution to hypertension," Apr. 8, 1991, Can. J. Physiol. Pharmacol., vol. 70, 1992, pp. 759-770.

Yamaguchi, Jun-ichi et al., "Prognostic Significance of Serum Creatinine Concentration for In-Hospital Mortality in Patients With Acute Myocardial Infarction Who Underwent Successful Primary Percutaneous Coronary Intervention (from the Heart Institute of Japan Acute Myocardial Infarction [Hijami] Registry)," Feb. 24, 2004, The American Journal of Cardiology, vol. 93, Jun. 15, 2004, © 2004 by Excerpta Medica, Inc., pp. 1526-1528.

Ye, Richard D., M.D., Ph.D., "Pharmacology of the Peripheral Nervous System," E-425 MSB, 6 pages.

Ye, Shaohua et al., "Renal Injury Caused By Intrarenal Injection of Phenol Increases Afferent and Efferent Renal Sympathetic Nerve Activity," Mar. 12, 2002, American Journal of Hypertension Aug. 2002, vol. 15, No. 8, © 2002 the American Journal of Hypertension, Ltd. Published by Elsevier Science Inc., pp. 717-724.

Yong-Quan, Dong et al., "The therapeutic effect of pulsed electric field on experimental spinal cord injury," Beijing Army General Hospital of People's Liberation Army, Beijing, 5 pages (full article in Chinese; abstract on last page).

Young, James B., M.D., FACC, "Management of Chronic Heart Failure: What Do Recent Clinical Trials Teach Us?" Reviews in Cardiovascular Medicine 2004, vol. 5, Suppl. 1, © 2004 MedReviews, LLC, pp. S3-S9.

Zanchetti, A. et al., "Neural Control of the Kidney—Are There Reno-Renal Reflexes?" Clin. and Exper. Hyper. Theory and Practice, A6 (1&2), © 1984 Marcel Dekker Inc., pp. 275-286.

Zimmermann, Ulrich, "Electrical Breakdown, Electropermeabilization and Electrofusion," Rev. Physiol. Biochem. Pharmacol., vol. 105, © Springer-Verlag 1986, pp. 175-256.

Zucker, Irving H. et al., "The origin of sympathetic outflow in heart failure: the roles of angiotensin II and nitric oxide" Progress in Biophysics & Molecular Biology 2004, vol. 84, © 2003 Elsevier Ltd., pp. 217-232.

Zundert, Jan Van, M.D. Fipp and Alex Cahana, M.D. Daapm, "Pulsed Radiofrequency in Chronic Pain Management: Looking for the Best Use of Electrical Current," Pain Practice 2005, vol. 5, Issue 2, © 2005 World Institute of Pain, pp. 74-76.

Cameron, Tracy. "Micromodular Implants to Provide Electrical Stimulation of Paralyzed Muslces and Limbs." IEEE Transactions on Biomedical Engineering, vol. 44, No. 9, Sep. 1997. pp. 781-790.

Guimaraes, Sarfim. "Vascular Adrenoceptors: An Update" pp. 319-356.

Hammer, Leah W. "Differential Inhibition of Functional Dilation of Small Arterioles by Indomethacin and Glibenclamide." Hypertension. Feb. 2001 Part II. pp. 599-603.

Hortobagyi, Gabriel N. "Randomized Trial of High-Dose Chemotherapy and Blood Cell Autografts for High-Risk Primary Breast Carcinoma" Journal of the National Cancer Institute, vol. 92, No. 3, Feb. 2, 2000 pp. 225-233.

Janda, J., "Impact of the electrical stimulation apparatus rebox on the course of ischemic renal damage in rats," British Library-"The world's knowledge" pp. 252-254 (translated and untranslated versions).

Bello-Reuss, E. et al., "Effect of renal sympathetic nerve stimulation on proximal water and sodium reabsorption," J Clin Invest, 1976;57:1104-1107.

Bhandari, A. and Ellias, M., "Loin pain hematuria syndrome: Pain control with RFA to the Splanchanic plexus," The Pain Clinic, 2000, vol. 12, No. 4, pp. 323-327.

Final Office Action; U.S. Appl. No. 11/451,728; Mailed on Jan. 13, 2009, 7 pages.

Final Office Action; U.S. Appl. No. 11/599,649; Mailed on Jan. 15, 2009. 10 pages.

International Search Report and Written Opinion, PCT/US05/35757, Mailed on Dec. 27, 2006, Applicant: Ardian, Inc., 8 pages.

International Search Report and Written Opinion, PCT/US06/48822, Mailed on Aug. 15, 2008, Applicant: Ardian, Inc., 12 pages.

International Search Report and Written Opinion, PCT/US07/70799, Mailed on Jul. 2, 2008, Applicant: Ardian, Inc., 7 pages.

International Search Report and Written Opinion, PCT/US07/84701, Mailed on Aug. 21, 2008, Applicant: Ardian, Inc., 11 pages.

Non-Final Office Action; U.S. Appl. No. 11/129,765; Mailed on May 18, 2007, 10 pages.

Non-Final Office Action; U.S. Appl. No. 11/129,765; Mailed on Sep. 10, 2007, 5 pages.

Non-Final Office Action; U.S. Appl. No. 11/129,765; Mailed on Oct. 6, 2006, 30 pages.

Non-Final Office Action; U.S. Appl. No. 11/144,173; Mailed on Apr. 5, 2007, 33 pages.

Non-Final Office Action; U.S. Appl. No. 11/144,173; Mailed on Sep. 10, 2007, 5 pages.

Non-Final Office Action; U.S. Appl. No. 11/145,122; Mailed on Apr. 11, 2007, 33 pages.

Non-Final Office Action; U.S. Appl. No. 11/145,122; Mailed on Sep. 10, 2007, 5 pages.

Non-Final Office Action; U.S. Appl. No. 11/451,728; Mailed on Jun. 12, 2008, 41 pages.

Non-Final Office Action; U.S. Appl. No. 11/599,649; Mailed on Mar. 30, 2009, 10 pages.

Non-Final Office Action; U.S. Appl. No. 11/599,649; Mailed on Jun. 23, 2008, 9 pages.

Osborn, et al., "Effect of renal nerve stimulation on renal blood flow autoregulation and antinatriuresis during reductions in renal perfusion pressure," in Proceedings of the Society for Experimental Biology and Medicine, vol. 168, 77-81, 1981. (Abstract).

* cited by examiner

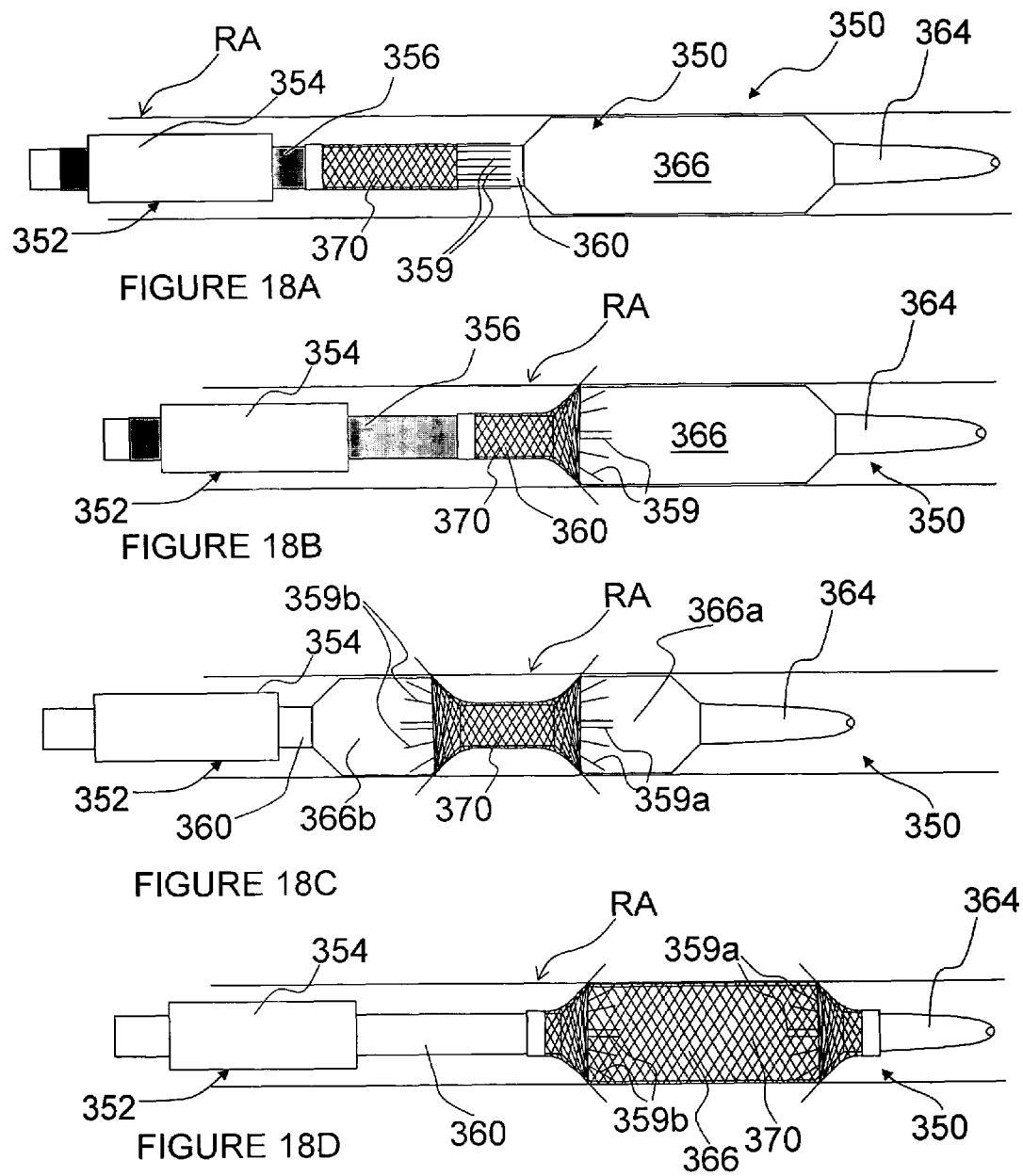

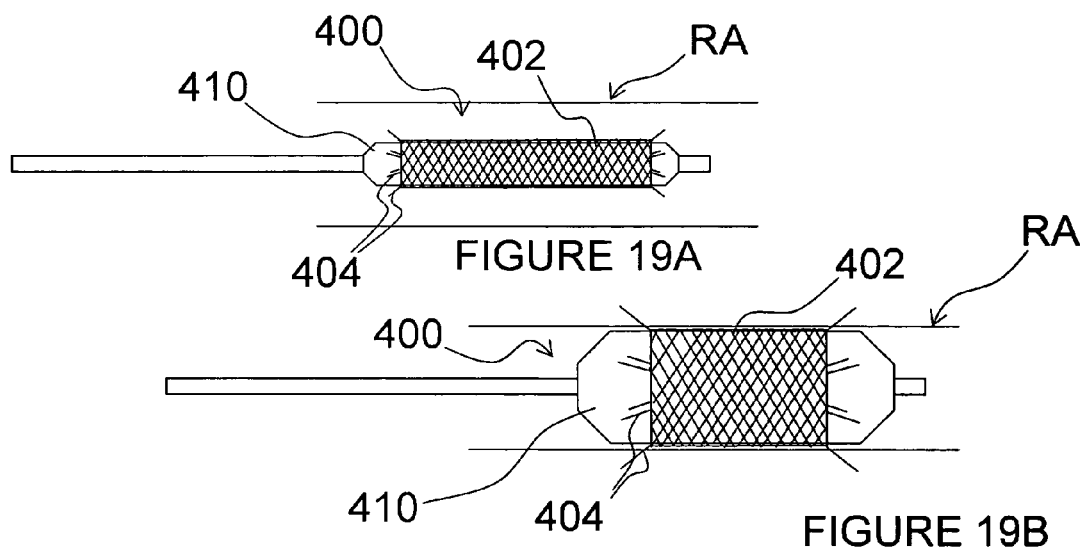

METHODS AND APPARATUS FOR PULSED ELECTRIC FIELD NEUROMODULATION VIA AN INTRA-TO-EXTRAVASCULAR APPROACH

CROSS REFERENCE TO RELATED APPLICATIONS

The present application claims the benefit of U.S. Provisional Application No. 60/813,589, filed on Dec. 29, 2005, entitled "METHODS AND APPARATUS FOR PULSED ELECTRIC FIELD NEUROMODULATION VIA AN INTRA-TO-EXTRAVASCULAR APPROACH" and originally filed as U.S. application Ser. No. 11/324,188), which is incorporated by reference herein. Further the present application is a continuation-in-part of each of the following co-pending U.S. Patent Applications:

(a) U.S. patent application Ser. No. 11/129,765, filed on May 13, 2005, which claims the benefit of U.S. Provisional Application Nos. 60/616,254, filed on Oct. 5, 2004; and 60/624,793, filed on Nov. 2, 2004. Further, this application is a continuation-in-part of U.S. patent application Ser. No. 10/408,665, filed on Apr. 8, 2003 (published as United States Patent Publication 2003/0216792 on Nov. 20, 2003), which claims the benefit of U.S. Provisional Patent Application Nos. 60/442,970, filed on Jan. 29, 2003; 60/415,575, filed on Oct. 3, 2002; and 60/370,190, filed on Apr. 8, 2002.

(b) U.S. patent application Ser. No. 11/189,563, filed on Jul. 25, 2005.

(c) U.S. patent application Ser. No. 11/266,933, filed on Nov. 4, 2005.

TECHNICAL FIELD

The present invention relates to methods and apparatus for neuromodulation. More particularly, the present invention relates to methods and apparatus for achieving pulsed electric field neuromodulation via an intra-to-extravascular approach.

BACKGROUND

Congestive Heart Failure ("CHF") is a condition that occurs when the heart becomes damaged and reduces blood flow to the organs of the body. If blood flow decreases sufficiently, kidney function becomes impaired, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to vasoconstriction of blood vessels supplying the kidneys, decreased renal blood flow, decreased removal of water and sodium from the body, and increased renin secretion. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, co-pending U.S. patent applications Ser. No. 11/129,765, filed on May 13, 2005, and Ser. No. 11/189,563, filed on Jul. 25, 2005, both of which are incorporated herein by reference in their entireties. A pulsed electric field ("PEF") may initiate renal neuromodulation, e.g., denervation, for example, via irreversible electroporation or via electrofusion. The PEF may be delivered from apparatus positioned intravascularly, extravascularly, intra-to-extravascularly or a combination thereof. As used herein, electrofusion comprises fusion of neighboring cells induced by exposure to an electric field. Contact between target neighboring cells for the purposes of electrofusion may be achieved in a variety of ways, including, for example, via dielectrophoresis. In tissue, the target cells may already be in contact, thus facilitating electrofusion.

As used herein, electroporation and electropermeabilization are methods of manipulating the cell membrane or intracellular apparatus. For example, the porosity of a cell membrane may be increased by inducing a sufficient voltage across the cell membrane through, e.g., short, high-voltage pulses. The extent of porosity in the cell membrane (e.g., size and number of pores) and the duration of effect (e.g., temporary or permanent) are a function of multiple variables, such as field strength, pulse width, duty cycle, electric field orientation, cell type or size and other parameters.

Cell membrane pores will generally close spontaneously upon termination of relatively lower strength electric fields or relatively shorter pulse widths (herein defined as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

In some patients, when a PEF sufficient to initiate irreversible electroporation is applied to renal nerves and/or other neural fibers that contribute to renal neural functions, applicants believe that denervation induced by the PEF would result in increased urine output, decreased plasma renin levels, decreased tissue (e.g., kidney) and/or urine catecholamines (e.g., norepinephrine), increased urinary sodium excretion, and/or controlled blood pressure that would prevent or treat CHF, hypertension, renal system diseases, and other renal or cardio-renal anomalies. PEF systems could be used to modulate efferent or afferent nerve signals, as well as combinations of efferent and afferent nerve signals.

A potential challenge of using intravascular PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring tissue impedance or conductivity to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005, which is incorporated herein by reference in its entirety. Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of target and/or non-target tissue may be utilized to determine the onset of electroporation and to determine the type or extent of electroporation. Furthermore, monitoring data may be used in one or more manual or automatic feedback loops to control the electroporation.

Regardless of whether or not monitoring techniques are utilized, the applied energy or voltage from an intravascular PEF system necessary to establish an electric field of sufficient magnitude in the vicinity of target neural fibers in order to modulate the target neural fibers may be of a magnitude that causes persistent damage to non-target tissue, such as smooth muscle cells of the vessel wall. Thus, a desired treatment outcome, e.g., renal denervation, may not be achievable with some intravascular PEF systems in certain patients without concomitantly inducing persistent damage to the non-target tissue. It therefore would be desirable to provide methods and apparatus for reducing the required magnitude of applied energy or voltage necessary to achieve desired neuromodulation in target tissue and/or to increase localization of the sufficient magnitude induced electric field to the vicinity of the target tissue.

SUMMARY

The present invention provides methods and apparatus for pulsed electric field ("PEF") neuromodulation via an intra-to-extravascular ("ITEV") approach, e.g., to effectuate irreversible electroporation or electrofusion, necrosis and/or inducement of apoptosis, alteration of gene expression, changes in cytokine upregulation, and other conditions in target neural fibers. In some embodiments, the ITEV PEF system comprises an intravascular catheter having one or more electrodes configured for intra-to-extravascular placement across a wall of a patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation may be reduced relative to an intravascular PEF system having one or more electrodes positioned solely intravascularly. The methods and apparatus of the present invention may, for example, be used to modulate one or more target neural fibers that contribute to renal function.

Pulsed electric field parameters may be altered and combined in any combination, as desired. Such parameters can include, but are not limited to, voltage, field strength, pulse width, pulse duration, the shape of the pulse, the number of pulses and/or the interval between pulses (e.g., duty cycle), etc. For example, suitable field strengths can be up to about 10,000 V/cm and suitable pulse widths can be up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, or combinations. The field includes at least one pulse, and in many applications the field includes a plurality of pulses. Suitable pulse intervals include, for example, intervals less than about 10 seconds. These parameters are provided as suitable examples and in no way should be considered limiting.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which:

FIGS. 18A-18D are schematic side-views, partially in section, of alternative embodiments of the methods and apparatus of FIG. 17.

FIGS. 19A and 19B are schematic side-views, partially in section, of methods and apparatus for pulsed electric field neuromodulation comprising a stent having electrodes configured for intra-to-extravascular placement.

DETAILED DESCRIPTION

A. Overview

The present invention relates to methods and apparatus for neuromodulation, e.g., denervation. More particularly, the present invention relates to methods and apparatus for achieving pulsed electric field neuromodulation via an intravascular-to-extravascular approach. In some embodiments, the ITEV PEF system comprises an intravascular catheter having one or more electrodes configured for intra-to-extravascular placement across a wall of patient's vessel into proximity with target neural fibers. With the electrode(s) passing from an intravascular position to an extravascular position prior to delivery of the PEF, a magnitude of applied voltage or energy delivered via the electrode(s) and necessary to achieve desired neuromodulation is reduced relative to an intravascular PEF system having one or more electrodes positioned solely intravascularly. The methods and apparatus of the present invention may, for example, be used to modulate one or more target neural fibers that contribute to renal function.

The methods and apparatus of the present invention may be used to modulate a neural fiber that contributes to renal function and may exploit any suitable electrical signal or field parameters, e.g., any electric field that will achieve the desired neuromodulation (e.g., electroporative effect). To better understand the structures of devices of the present invention and the methods of using such devices for renal neuromodulation and monitoring, it is instructive to examine the renal anatomy in humans.

B. Selected Embodiments of Methods for Neuromodulation

Figure 1:
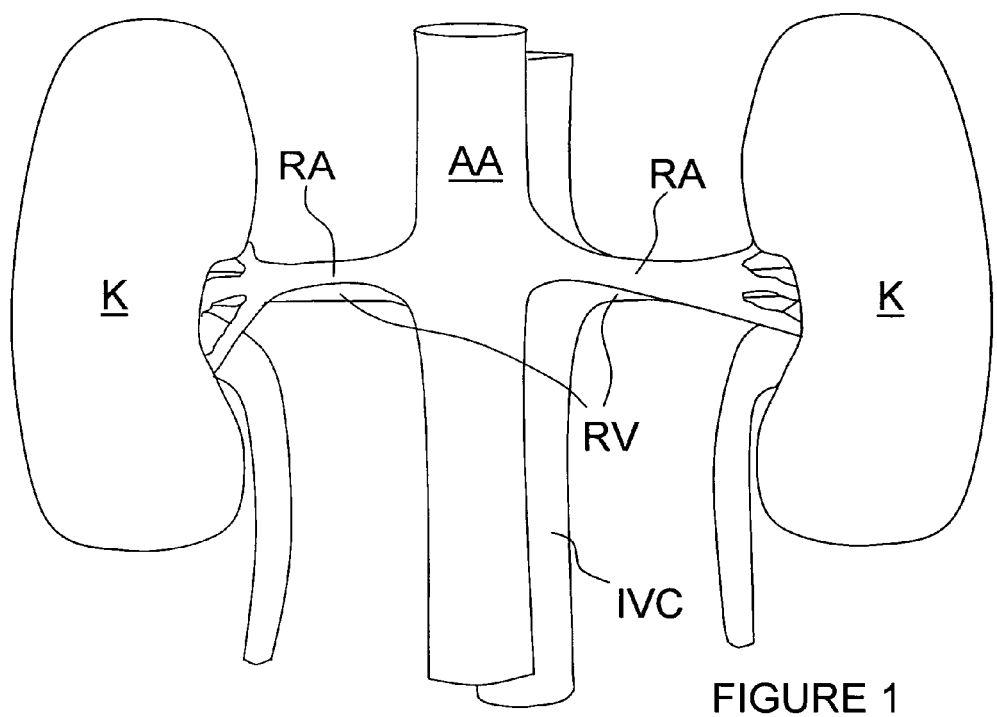
FIG. 1 is a schematic view illustrating human renal anatomy.
Figure 2:
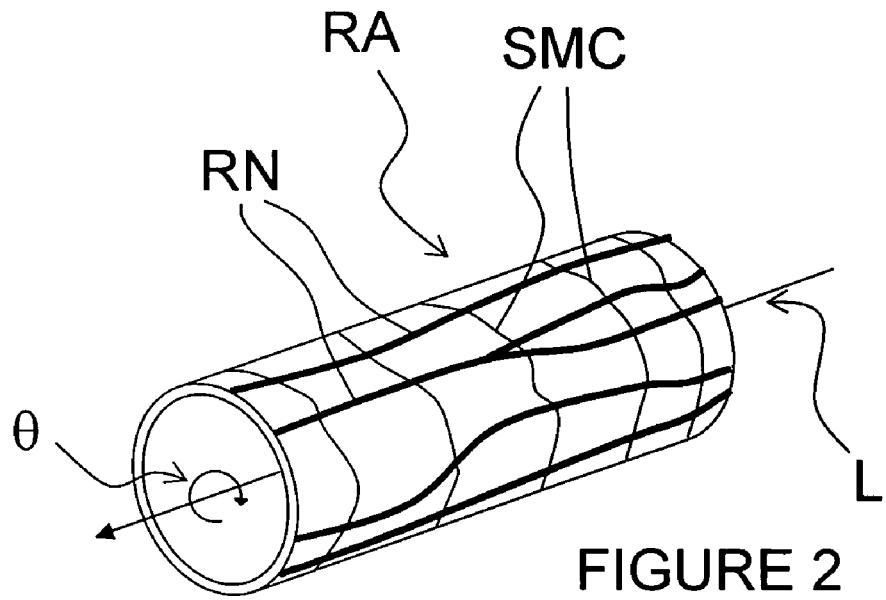
FIG. 2 is a schematic detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
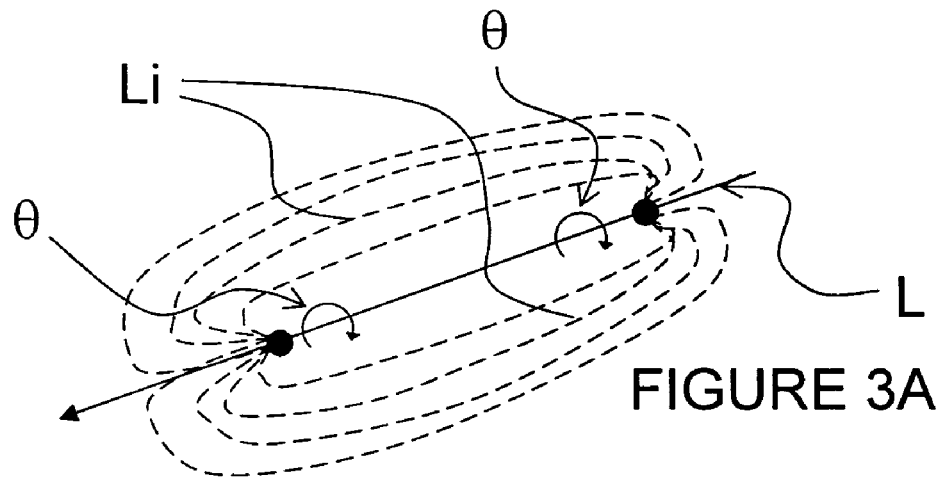
FIGS. 3A and 3B are schematic side- and end-views, respectively, illustrating orienting of an electric field for selectively affecting renal nerves.
Figure 3B:
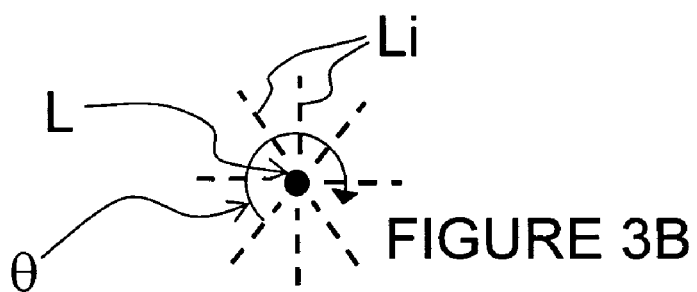

Referring to FIG. 3, the cellular misalignment of the renal nerves and the smooth muscle cells may be exploited to selectively affect renal nerve cells with reduced effect on smooth muscle cells. More specifically, because larger cells require a lower electric field strength to exceed the cell membrane irreversibility threshold voltage or energy for irreversible electroporation, embodiments of electrodes of the present invention may be configured to align at least a portion of an electric field generated by the electrodes with or near the longer dimensions of the cells to be affected. In specific embodiments, the device has electrodes configured to create an electrical field aligned with or near the lengthwise dimension L of the renal artery RA to affect renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells, to induce apoptosis, to alter gene expression, to change cytokine upregulation, and/or to induce other suitable processes. This is expected to reduce total energy delivered to the system and to mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning the PEF with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIG. 3, applying a PEF with propagation lines Li generally aligned with the longitudinal dimension L of the renal artery RA is expected to preferentially cause electroporation, electrofusion, denervation or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

A PEF system placed within and/or at least partially across the wall of the renal artery, e.g., via an intra-to-extravascular ("ITEV") approach, may propagate an electric field having a longitudinal portion that is aligned to run with the longitudinal dimension of the artery in the region of the renal nerves RN and the smooth muscle cell SMC of the vessel wall so that the wall of the artery remains at least substantially intact while the outer nerve cells are destroyed, fused or otherwise affected. Monitoring elements may be utilized to assess an extent of, e.g., electroporation, induced in renal nerves and/or in smooth muscle cells, as well as to adjust PEF parameters to achieve a desired effect.

C. Exemplary Embodiments of Systems and Additional Methods for Neuromodulation

With reference to FIG. 4, embodiments of intra-to-extravascular ("ITEV") PEF systems and methods of the present invention are described. ITEV PEF systems of the present invention are configured for temporary intravascular placement and for passage of one or more electrodes across a wall of the vasculature for extravascular placement. Furthermore, the systems are configured to deliver pulsed electric fields to neural fibers for neuromodulation. In one particular example, the systems are configured to deliver the pulsed electric fields to neural fibers that contribute to renal function in order to achieve renal neuromodulation. For the purposes of the present invention, extravascular shall refer to any position external to the intima and media layers of the vasculature. Extravascular may, for example, include positions within the adventitia of the vessel or within surrounding fatty tissue.

In FIGS. 4A-D, an ITEV PEF system 100 comprises an intravascular catheter 102 having a lumen 103, a shaped cannula 104 configured for low-profile delivery within the lumen 103 and for advancement from the lumen 103 in order to pierce the wall of a patient's vasculature, and a first guide wire electrode 106 configured for advancement through a lumen 105 of the cannula 104. The cannula 104 may, for example, be fabricated from a shape memory material (e.g., Nitinol) or a flexible, pre-formed elastic material (e.g., thin-walled stainless steel).

Figure 4A:
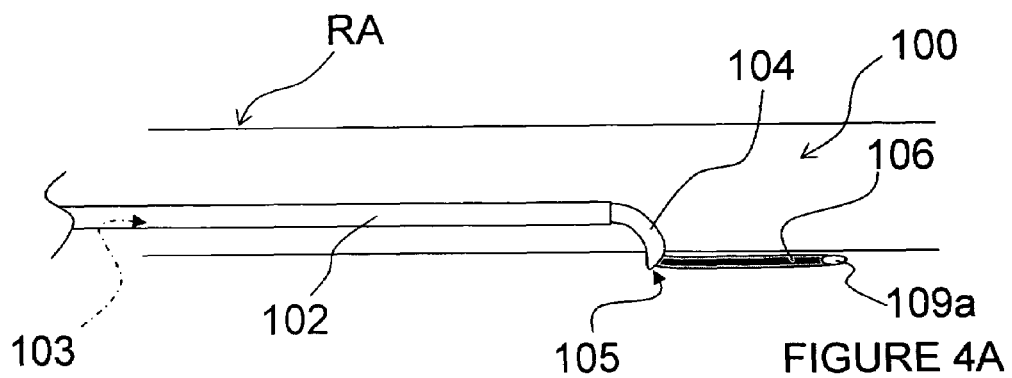
FIGS. 4A-4D are schematic side-views, partially in section, illustrating methods and apparatus for pulsed electric field neuromodulation via an intra-to-extravascular approach having a bipolar electrode pair with at least one of the electrodes of the pair positioned extravascularly.
Figure 4B:
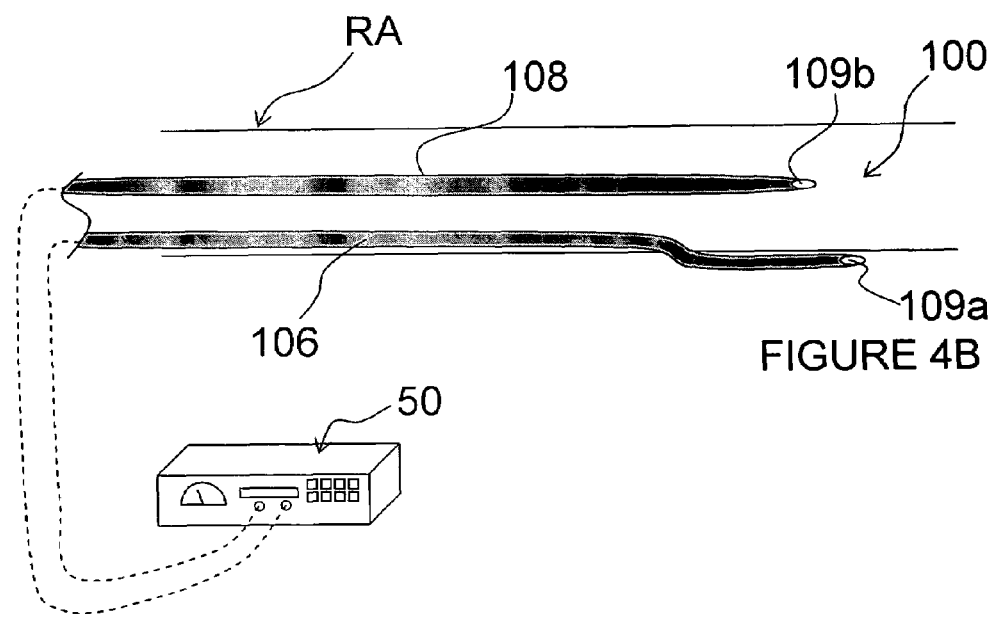

In the embodiment of FIGS. 4A and 4B, system 100 further comprises a second guide wire electrode 108 (FIG. 4B) configured for intravascular positioning. The guide wire electrodes 106 and 108, which form a bipolar electrode pair, optionally may be insulated at all regions, except their distal ends. The electrodes are electrically connected to a pulsed electric field generator 50 (FIG. 4B) located external to the patient. The generator may be utilized with any embodiment of the present invention to deliver a PEF with desired field parameters. It should be understood that several examples of PEF-delivery electrodes described below may be electrically connected to the generator even though the generator is not explicitly shown or described with each embodiment.

In use, the catheter 102 may be delivered to renal artery RA as shown in FIG. 4A, or it may be delivered through a guide catheter or other device to a renal vein or to any other vessel in proximity to target neural tissue (e.g., target neural tissue that contributes to renal function). The catheter preferably is delivered via a percutaneous technique, such as via a percutaneous femoral artery access. Once the shaped cannula 104 is positioned within the patient's vasculature, it may be advanced past the outlet of the lumen 103 of the catheter 102 such that the cannula 104 assumes a curved or otherwise angular profile. As the cannula 104 advances further, it pierces the wall of the patient's vasculature to be positioned extravascularly (i.e., at least within the adventitia). The first guide wire electrode 106 is then advanced through the cannula lumen 105 such that a non-insulated distal region 109a of the first electrode 106 is positioned extravascularly via an intra-to-extravascular approach. The cannula 104 may be retracted, and the catheter 102, as well as the cannula 104 may be removed from the patient or from the treatment site. The second guide wire electrode 108 has a non-insulated distal region 109b that is positioned intravascularly (before, during or after extravascular placement of the first electrode 106) to form a bipolar electrode pair with the first electrode 106 (FIG. 4B).

The first electrode 106 preferably comprises the active electrode and the second electrode 108 preferably comprises the return electrode. However, it should be understood that the electrode polarities optionally may be reversed. The non-insulated distal regions 109a-b of the electrodes 106 and 108 optionally may be in substantial alignment along a cross-sectional plane through renal artery RA. Alternatively, the distal regions 109a-b may be spaced apart longitudinally. Such longitudinal spacing of the distal regions 109a-b may, for example, better align a pulsed electric field delivered across the electrodes with a longitudinal dimension of the renal artery to facilitate modulation of renal nerves with limited effect on non-target smooth muscle cells or other cells, as described previously with respect to FIG. 3.

With the first and second electrodes 106 and 108 positioned as desired, a pulsed electric field generated by the PEF generator 50 is transmitted through the electrodes 106 and 108 and delivered across the non-insulated distal regions 109a-b of the electrodes. The PEF therapy modulates activity along neural fibers that directly or indirectly contribute to renal function (e.g., denervates neural fibers related to renal function). This may be achieved, for example, via irreversible electroporation, electrofusion, necrosis and/or inducement of apoptosis in the nerve cells, alteration of gene expression, changes in cytokine upregulation, and/or other suitable processes. After delivery of PEF therapy, the ITEV PEF system 100 may be removed from the patient to conclude the procedure.

It is expected that PEF therapy using the ITEV PEF system 100 will alleviate clinical symptoms of CHF, hypertension, renal disease and/or other cardio-renal diseases for a period of months, potentially up to six months or more. This time period might be sufficient to allow the body to heal; for example, this period might reduce the risk of CHF onset after an acute myocardial infarction, thereby alleviating a need for subsequent re-treatment. Alternatively, as symptoms reoccur, or at regularly scheduled intervals, the patient might return to the physician for a repeat therapy.

In order to denervate or otherwise modulate target neural fibers, the ITEV PEF system 100 should generate an electric field of sufficient strength or magnitude across the fibers to induce such denervation or modulation. When utilizing an intravascular PEF system, depending upon the arrangement and positioning of the PEF electrodes, as well as the physiology of the patient, the applied voltage necessary to achieve a field strength of sufficient magnitude at the target neural fibers also may be of sufficient magnitude to induce undesirable persistent injury in non-target tissue, such as smooth muscle cells and/or the vessel wall. It is expected that the extravascular positioning of electrode 106 via an intra-to-extravascular approach will reduce the necessary applied voltage for denervation or modulation (e.g., renal denervation or modulation) via PEF therapy compared to the applied voltage required when utilizing solely intravascular apparatus with similarly spaced and sized electrodes. Specifically, extravascular placement of electrode 106 in closer proximity to the target neural fibers is expected to increase localization of the peak induced electric field to the vicinity of the target neural fibers.

Figure 4C:
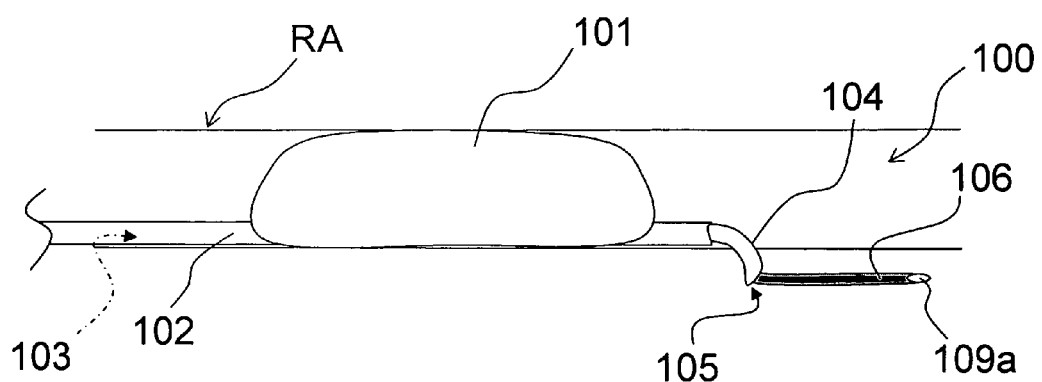
Figure 4D:
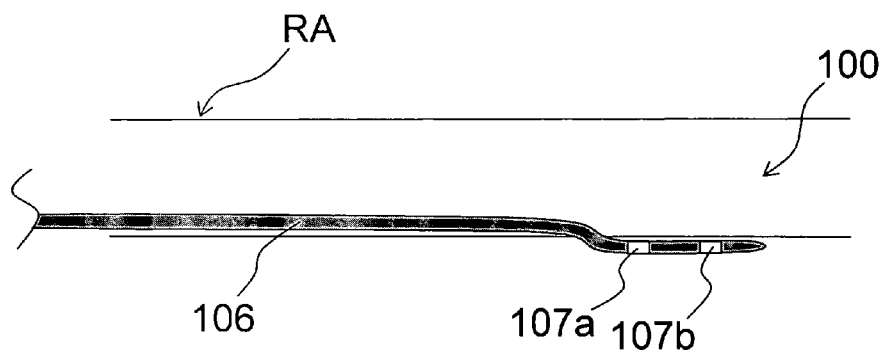

As seen in FIG. 4C, the catheter 102 optionally may comprise an expandable element 101 (e.g., an inflatable balloon) that stabilizes the catheter 102 within the patient's vessel. The expandable element 101 further facilitates piercing of the vessel wall with the cannula 104 to position the first electrode 106 at an extravascular location. As seen in FIG. 4D, the first electrode 106 may comprise a spaced bipolar electrode pair 107a and 107b to obviate the need for the intravascular second electrode 108. The PEF therapy may be delivered extravascularly across the bipolar electrode pair 107a-b.

The extravascular second electrode 106 optionally may be replaced with a virtual electrode. For example, conductive saline may be injected through cannula 104 into the extravascular space. The conductive saline may provide a virtual electrode surrounding all or part of the circumference of the vessel and may be used in a bipolar fashion with intravascular electrode 108.

Figure 5:
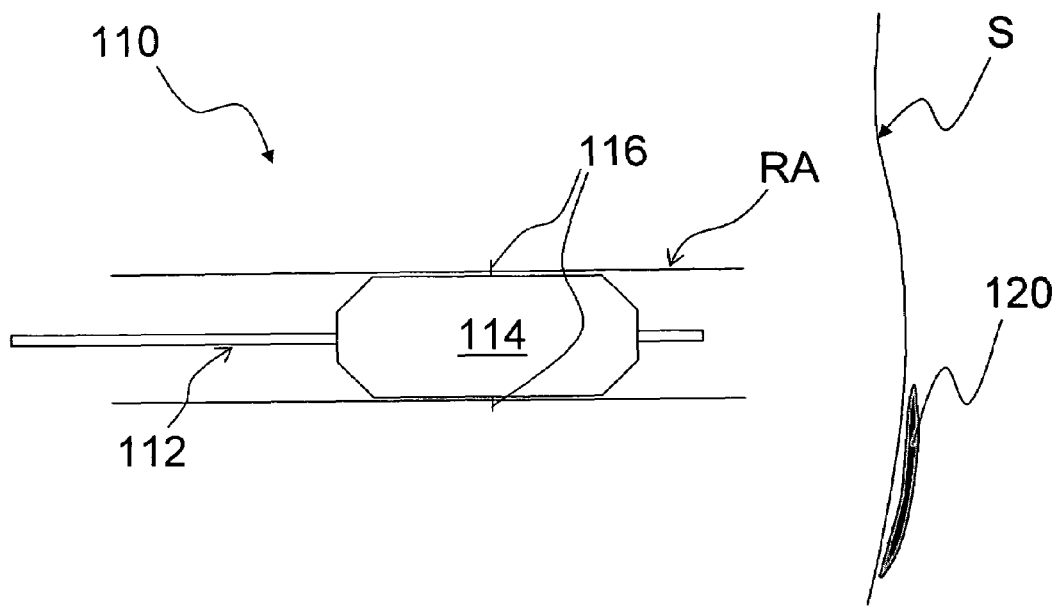
FIG. 5 is a schematic view, partially in section, illustrating methods and apparatus for monopolar pulsed electric field neuromodulation via an intra-to-extravascular approach.

The examples of the ITEV PEF systems of FIGS. 4A-D optionally may be utilized in a monopolar fashion by replacing the intravascular second electrode 108 with a ground pad coupled to the PEF generator 50 and attached to the exterior of the patient. FIG. 5 illustrates an alternative monopolar ITEV PEF system 110 comprising a catheter 112 having an expandable element 114 with one or more needle-like ITEV electrodes 116 coupled to the expandable element. When multiple needle electrodes 116 are provided, they may be spaced circumferentially and/or longitudinally about/along the expandable element 114. The system 110 further comprises a ground pad 120 attached to the skin S of the patient along the exterior of the patient (e.g., to the patient's flank, back or thigh) and coupled to the PEF generator 50 as a return electrode. The ground pad 120 optionally may be positioned directly lateral to the ITEV electrode(s) 116 to direct the PEF therapy along the patient's vasculature (e.g., along renal artery RA).

The expandable element 114 comprises a member or structure configured for intravascular delivery to (and retrieval from) a target location in a low profile configuration and for expansion to an expanded deployed configuration at the target location. The expandable element 114 may comprise, for example, an inflatable balloon, an expandable basket or cage, or other expandable structure. As seen in FIG. 5, expansion of the expansion element 114 causes the ITEV electrode(s) 116 to pierce the wall of renal artery RA and move from an intravascular location to an extravascular location. With the ITEV electrode(s) 116 positioned extravascularly and coupled to the PEF generator 50, the ITEV electrode(s) may be energized as active electrodes in a monopolar PEF therapy with the external ground pad 120 serving as the return electrode.

Figure 6A:
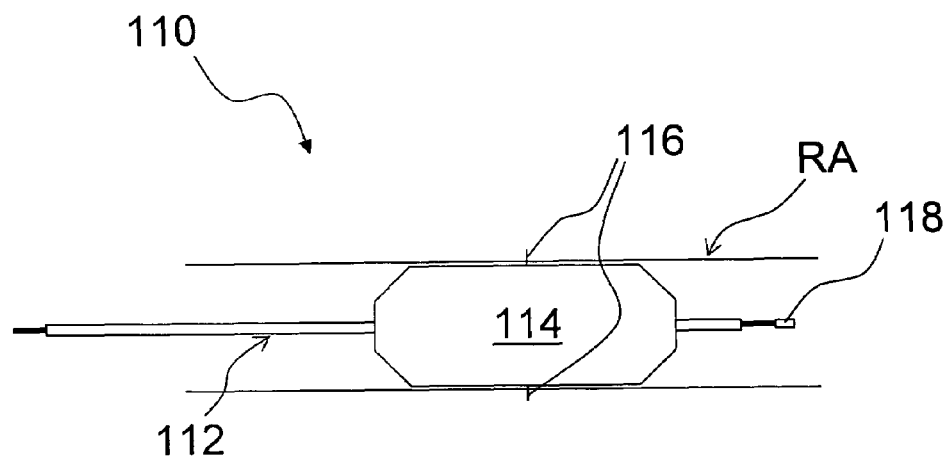
FIGS. 6A-6C are schematic side-views, partially in section, illustrating alternative embodiments of the methods and apparatus of FIG. 5, the methods and apparatus comprising a bipolar electrode pair having a first electrode positioned extravascularly and a second electrode positioned intravascularly.
Figure 6B:
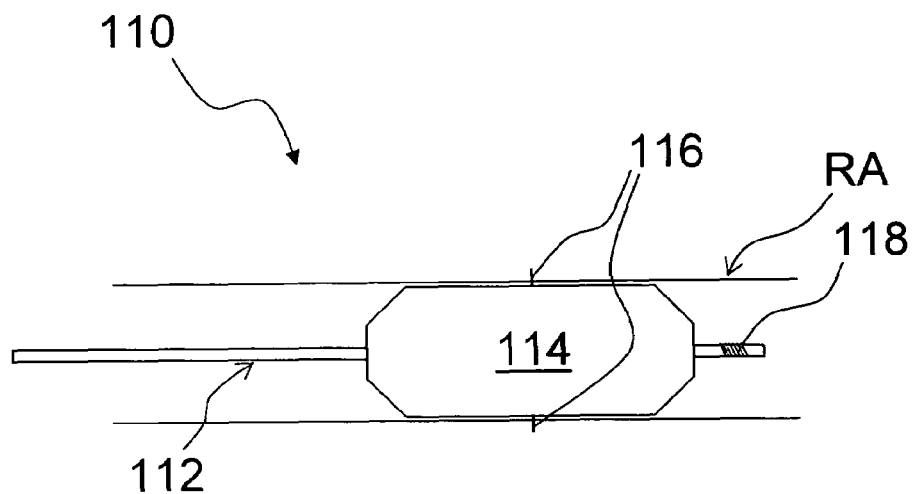
Figure 6C:
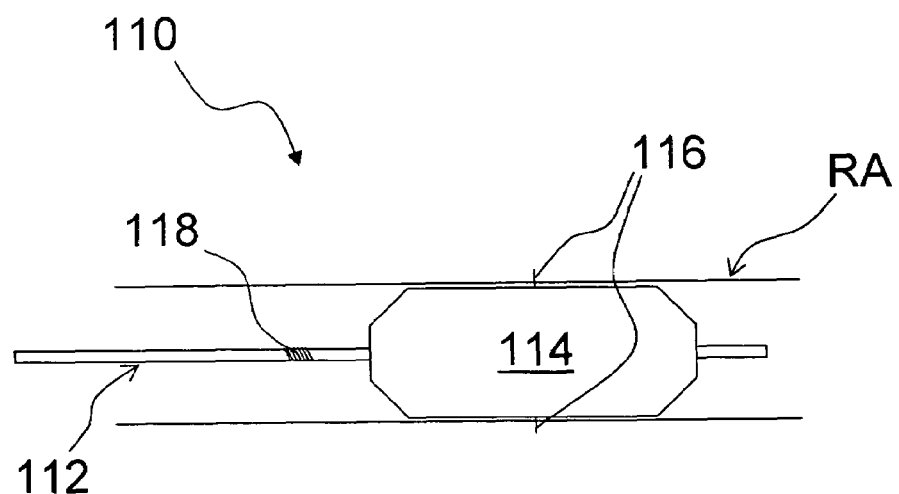

Referring now to FIGS. 6A-C, alternative embodiments of the ITEV PEF system 110 are described comprising a first electrode positioned extravascularly and a second electrode positioned intravascularly. In FIGS. 6A-C, the ITEV PEF systems 110 again comprise the catheter 112 having the expandable element 114 with one or more ITEV electrodes 116 coupled to the expandable element and configured for intra-to-extravascular delivery. The systems 110 further comprise an intravascular second electrode 118 positioned within the vessel. In FIG. 6A, the second electrode 118 comprises a guidewire electrode positioned within the lumen of the catheter 112. The guidewire electrode 118 is coupled to the PEF generator 50 and is insulated at regions other than a distal region positioned distal of the catheter 112. In FIG. 6B, the second electrode 118 is coupled to the shaft of the catheter 112 distally of the expandable element 114. In FIG. 6C, the second electrode 118 is coupled to the shaft of catheter 112 proximally of the expandable element 114. In use, the ITEV electrode(s) 116 may comprise active electrode(s) and the second electrode 118 may comprise a return electrode, or vice versa. The second electrode 118 optionally may be longitudinally spaced relative to the ITEV electrode(s) 116 to align the PEF therapy with a longitudinal axis of the patient's vasculature, as described previously with respect to FIGS. 2 and 3. The second electrodes 118 may, for example, be fabricated from wound coils of wire. When utilizing relatively long electrodes, wound coils allow the catheter 112 to maintain desired flexibility.

Figure 7A:
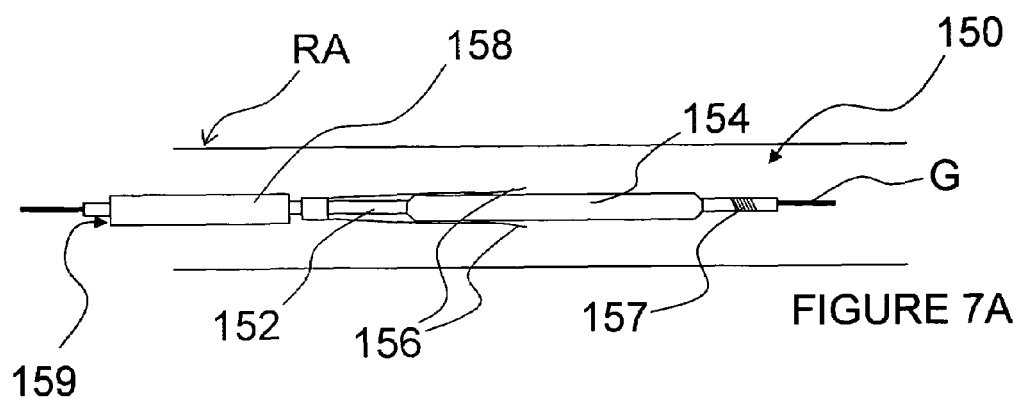
FIGS. 7A and 7B are schematic side-views, partially in section, illustrating additional methods and apparatus for pulsed electric field neuromodulation via a bipolar electrode pair, the bipolar electrode pair comprising at least one first electrode positioned extravascularly and at least one second electrode positioned intravascularly.
Figure 7B:
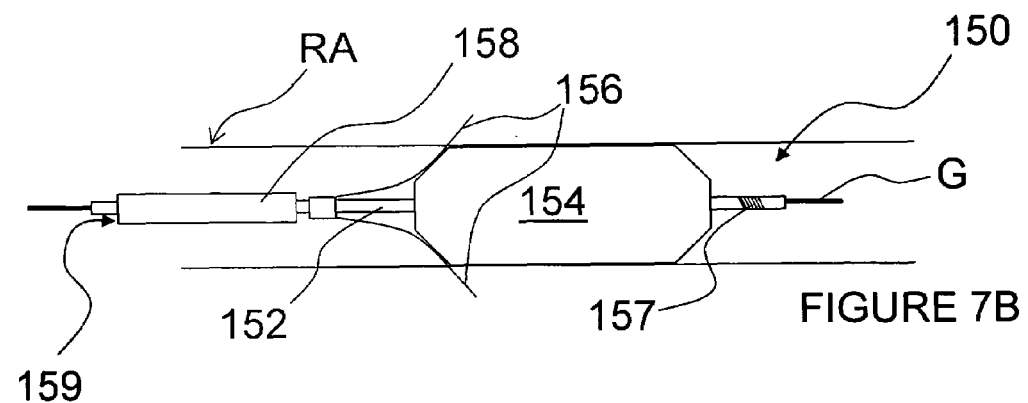

Referring now to FIGS. 7A and 7B, additional methods and apparatus for pulsed electric field neuromodulation via a bipolar electrode pair having a first electrode positioned extravascularly and a second electrode positioned intravascularly are described. FIGS. 7A and 7B, more specifically, illustrate an ITEV PEF system 150 comprising a catheter 152 and an expandable element 154, which may comprise an inflatable balloon or an expandable wire cage. The system 150 further comprises one or more ITEV needle electrodes 156 that are coupled to the catheter 152, illustratively proximal of expandable element 154, and return electrode 157, illustratively coupled to the shaft of catheter 152 distal of expandable element 154. Additionally, the system comprises a protective sheath 158 having a lumen 159 in which the catheter 152 may be positioned for percutaneous advancement and/or retrieval.

In FIGS. 7A and 7B, the distal regions of the ITEV electrodes 156 extend laterally over, but are not connected to, at least a portion of the expandable element 154. This is in contrast to the previously described ITEV PEF systems of FIGS. 4-6 that have ITEV electrodes coupled directly to an expandable element. By separating the ITEV electrode(s) 156 from the expandable element 154, the system 150 of FIGS. 7A and 7B may simplify manufacturing and/or enhance expansion reliability.

As seen in FIG. 7A, the catheter 152 and the protective sheath 158 may be advanced into position within the patient's vasculature (e.g., within renal artery RA over guidewire G). Once in position, the sheath 158 may be retracted relative to the catheter 152 and/or the catheter 152 may be advanced relative to the sheath 158 such that the expandable element 154, the ITEV electrode(s) 156 and the return electrode 157 are positioned distally of the protective sheath 158. As seen in FIG. 7B, the expandable element 154 then may be expanded, such that the ITEV needle electrode(s) 156 puncture the vessel wall and are positioned extravascularly via an ITEV approach. Once the electrode(s) 156 are positioned extravascularly, PEF therapy may proceed between the ITEV electrode(s) 156 and the return electrode 157. The PEF therapy, for example, can modulate and/or denervate a neural fiber that contributes to renal function. Upon completion of the PEF therapy, the expandable element 154 may be collapsed, and the sheath 158 may be advanced relative to the catheter 152, such that the ITEV electrodes 156 are removed from the vessel wall. The system 150 then may be removed from the patient to complete the procedure.

Figure 8A:
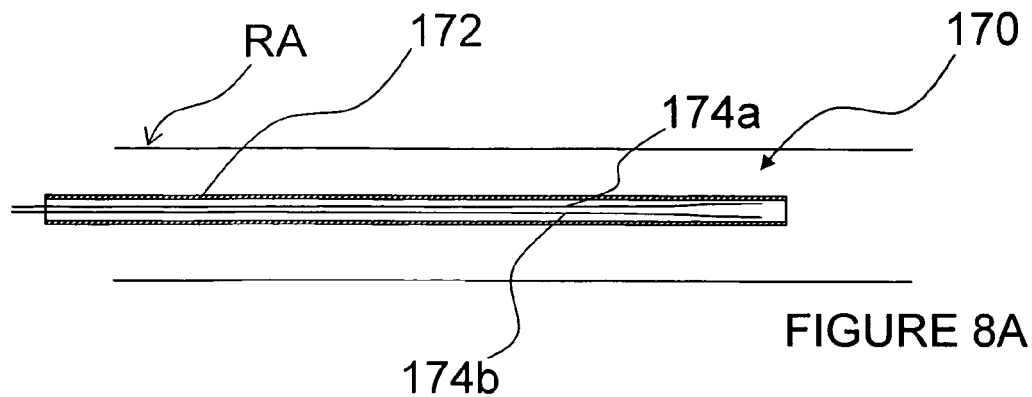
FIGS. 8A-8C are a schematic side-sectional view and schematic side-views, partially in section, illustrating methods and apparatus for pulsed electric field neuromodulation having at least one bipolar electrode pair with both electrodes of each electrode pair positioned extravascularly via an intra-to-extravascular approach.
Figure 8B:
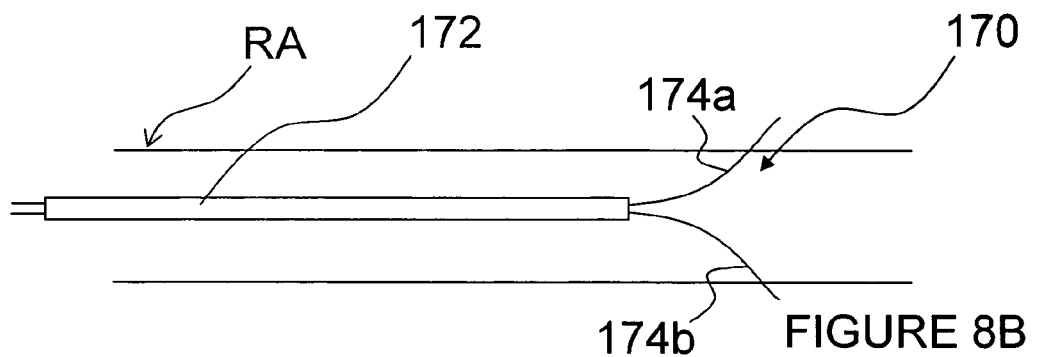
Figure 8C:
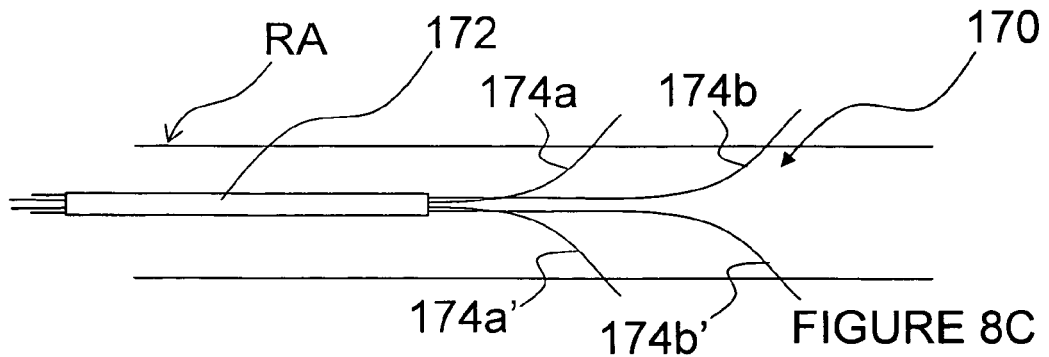

Referring now to FIGS. 8A-C, methods and apparatus for pulsed electric field neuromodulation are described utilizing one or more bipolar electrode pairs with both electrodes of each pair positioned extravascularly via an intra-to-extravascular approach. One example of such an ITEV PEF system 170 comprises a catheter or sheath 172 having shaped ITEV bipolar needle electrodes 174a and 174b that are configured for advancement to an intravascular location within the sheath. The electrodes 174a-b may have shape-memory properties (e.g., may be fabricated from a shape-memory alloy such as Nitinol) and may be insulated at locations other than their distal regions. As seen in FIG. 8B, upon advancement of the electrodes 174a-b to a position distal of the sheath 172 (e.g., via retraction of the sheath), the electrodes 174a-b assume their preformed shape and puncture the wall of the patient's vasculature, illustratively renal artery RA, such that the distal regions of the electrodes 174*a-b* are positioned extravascularly via an ITEV approach. As will be apparent, electrodes 174*a* and 174*b* may be longitudinally spaced relative to one another to better align the PEF therapy with a longitudinal dimension of the patient's vasculature. Furthermore, although the electrodes illustratively are spaced radially about 180° apart, it should be understood that the electrodes alternatively may be spaced with any desired radial separation (or lack thereof).

FIG. 8C illustrates another example of the ITEV PEF system 170 comprising multiple pairs of ITEV electrodes that are longitudinally spaced. The system 170, for example, can comprise a first bipolar electrode pair 174*a* and 174*b*, and a second bipolar electrode pair 174*a'* and 174*b'*. Additional pairs of bipolar electrodes at different circumferential positions or with different longitudinal spacing may be utilized as desired in other examples.

Once properly positioned, PEF therapy may be delivered across the electrodes 174 to achieve desired neuromodulation. Upon completion of the PEF therapy, the needle electrodes 174 may be retracted relative to the sheath 172, and/or the sheath 172 may be advanced relative to the electrodes 174, such that the electrodes are removed from the wall of the patient's vasculature and coaxed back into a constrained retrieval configuration within the sheath. The ITEV PEF system 170 then may be removed from the patient to complete the procedure.

Figure 9:
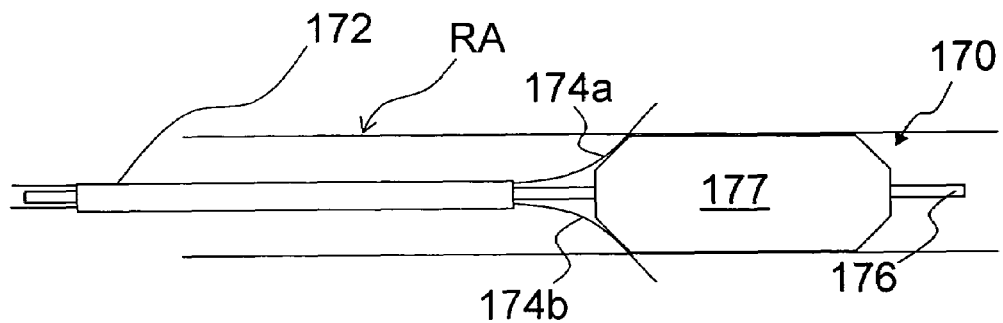
FIG. 9 is a schematic side-view, partially in section, of an alternative embodiment of the apparatus and methods of FIG. 8.

With reference to FIG. 9, an alternative embodiment of the ITEV PEF system 170 is described comprising a catheter 176 having an expandable element 177. The expandable element 177 acts as a guide that, when expanded, directs or forces the electrodes 174 across the vessel wall. More specifically, the expandable element 177 can direct the electrodes 174 through the vessel wall by advancing the electrodes 174 along the expandable element 177 after it has been expanded. Alternatively, the expandable element 177 can force the electrodes 174 across the vessel wall by advancing the electrodes 174 over the expandable element 177 while the expandable element 177 is in a reduced profile configuration and then expanding of the expandable element 177 to force the electrodes 174 across the wall of the vessel.

Figure 10A:
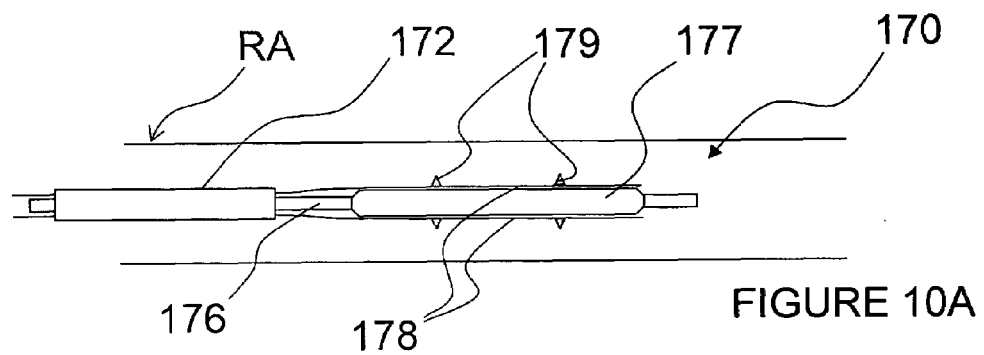
FIGS. 10A-10F are schematic side-views, partially in section, of alternative embodiments of the apparatus and methods of FIG. 9 comprising multiple pairs of bipolar electrodes.
Figure 10B:
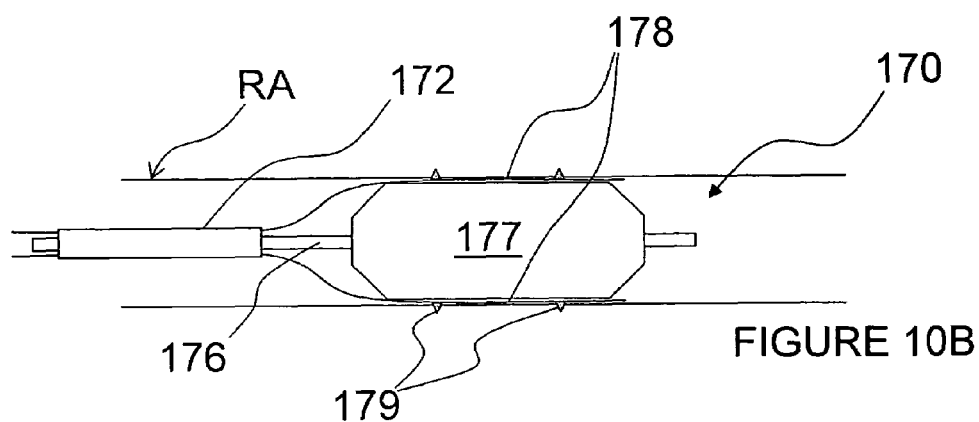

FIGS. 10A-F illustrate additional alternative embodiments of the ITEV PEF system 170 comprising multiple pairs of bipolar electrodes. In FIGS. 10A and 10B, the ITEV electrodes 174 have been replaced with ITEV electrode carriers 178. Each ITEV electrode carrier 178 comprises multiple electrodes 179. For example, each electrode carrier 178 may comprise a pair of electrically-isolated bipolar electrodes 179. Alternatively, each carrier 178 may comprise multiple electrodes 179 of a common polarity. The electrodes 179 comprise sharpened points, pins, or other raised features for penetrating the wall of the patient's vasculature. As seen in FIG. 10A, the electrodes 179 may be delivered to the stimulation site in a low profile configuration, e.g., through or within the sheath 172. The electrodes 179 then may be positioned extravascularly via an ITEV approach by expanding the expandable element 177, as in FIG. 10B.

Figure 10C:
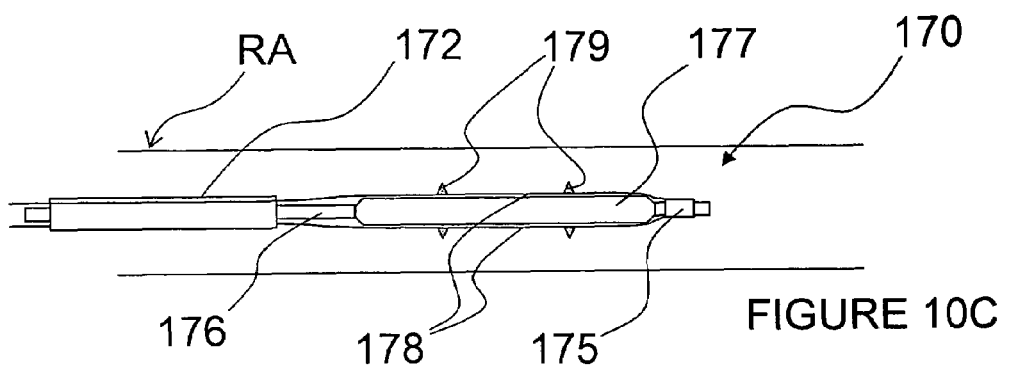
Figure 10D:
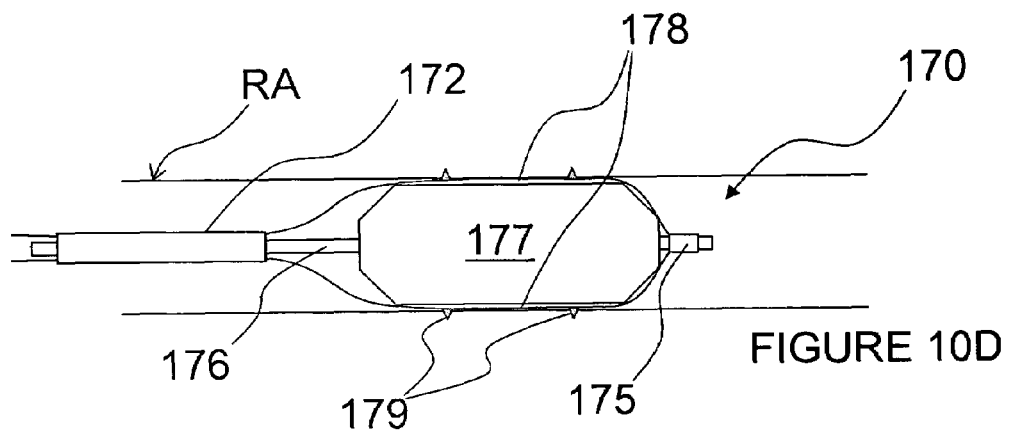

As seen in FIGS. 10C and 10D, the electrode carriers 178 optionally may be coupled to a catheter 176 distal of the expandable element 177 at a collar 175. The collar 175 may be slidingly attached to the catheter 176 and/or may be longitudinally constrained. An expected benefit of attaching the carriers to the catheter is good control of the extravascular positioning of electrodes 179 via an ITEV approach.

Figure 10E:
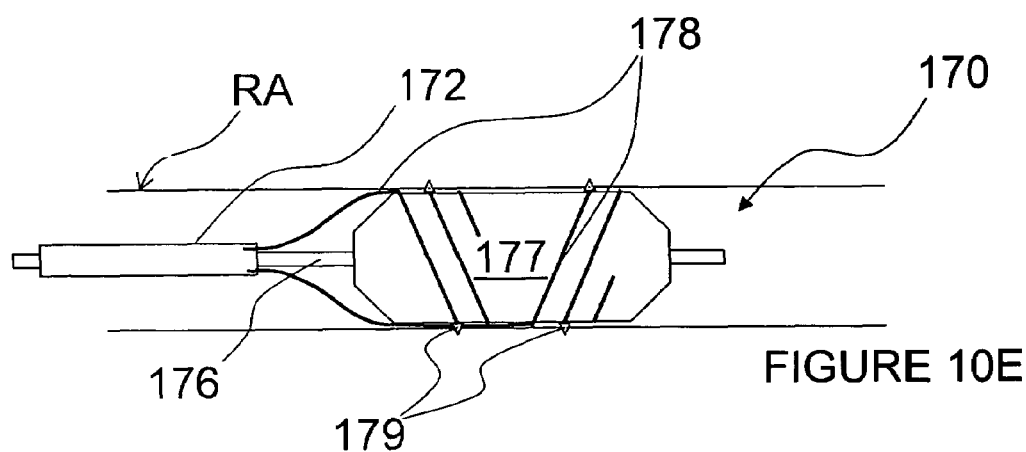

As seen in FIG. 10E, the electrode carriers 178 optionally may spiral around the expandable element 177. The carriers 178 optionally may comprise several electrodes 179 positioned at multiple circumferential positions to facilitate more circumferential PEF therapy. The electrode carriers 178 preferably are electrically isolated from one another. For example, the carriers 178 may be insulated at all regions except for at the electrodes 179.

Figure 10F:
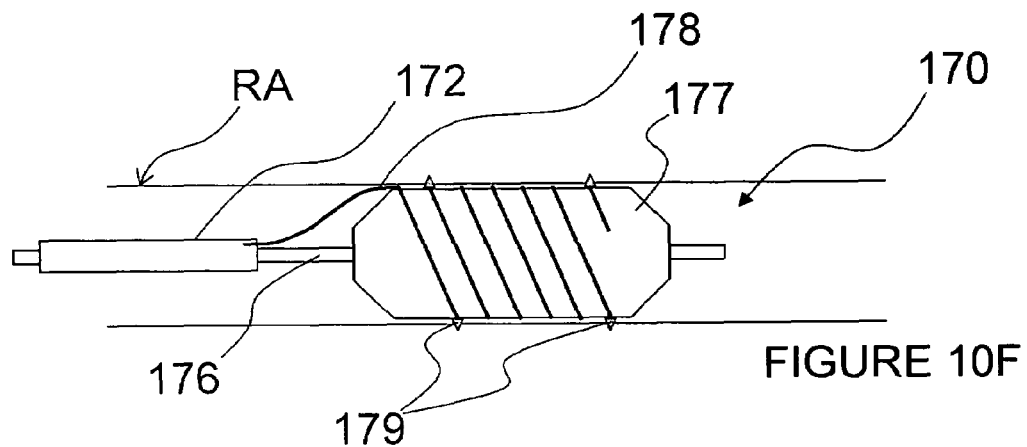

As seen in FIG. 10F, the system 170 optionally may comprise a single electrode carrier 178 that spirals around the expandable element 177. A plurality of the electrodes along the unitary carrier may be of a common polarity and/or may be electrically isolated from one another and of varying polarity to form bipolar electrode pair(s). The electrodes 179 may be positioned a multiple circumferential positions, as desired.

Figure 11A:
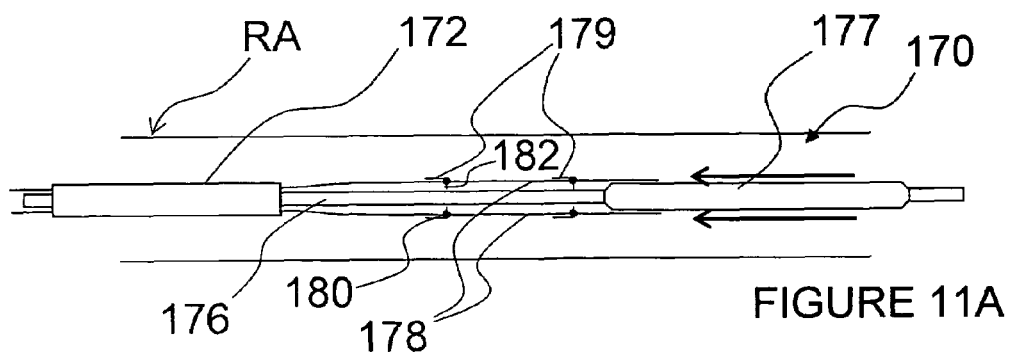
FIGS. 11A-11C are schematic side-views, partially in section, of an alternative embodiment of the apparatus and methods of FIG. 10 comprising a safety feature for intravascular delivery of the electrodes prior to extravascular placement.
Figure 11B:
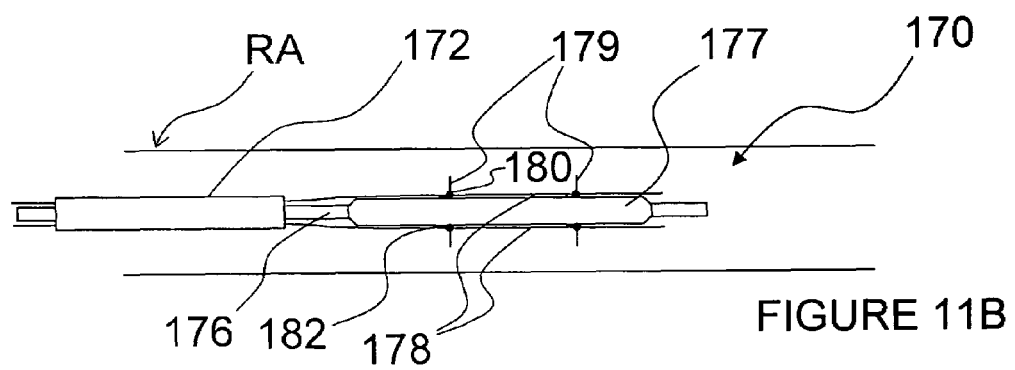
Figure 11C:
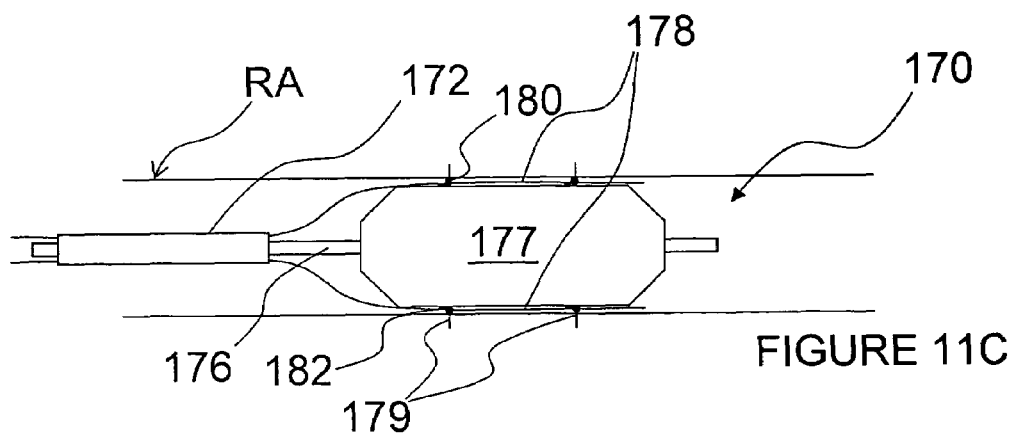

FIGS. 11A-C show additional examples of the ITEV PEF system 170 comprising a safety feature that facilitates intravascular delivery of the electrodes 179 prior to extravascular placement of the electrodes. In the embodiment of FIGS. 11A-C, the electrodes 179 are coupled to electrode carriers 178 in a manner that facilitates rotation of the electrodes 179 relative to the respective carriers 178. For example, the electrodes 179 may be coupled to the carriers 178 at pivots 180, which may comprise rotational bearing surfaces. Furthermore, the electrodes 179 comprise extensions 182 that co-act with the expandable element 177 to selectively rotate the electrodes 179 between a reduced delivery and retrieval profile and an expanded profile suitable for ITEV delivery of the electrodes. The electrodes 179 optionally may be biased towards the reduced profile, e.g., via a spring mechanism. The reduced profile serves as a safety feature that reduces a risk of inadvertent perforation of vascular tissue prior to ITEV placement of the electrodes at a treatment site.

As seen in FIG. 11A, the electrodes 179 lie flat near or against the electrode carrier 178 during delivery to an intravascular treatment site (e.g., through or within the sheath 172). The electrodes 179 are positioned proximal of the expandable element 177 during delivery. Once positioned within the vessel, the electrodes 179 are expanded such that their tips point radially outward by retracting the expandable element 177 relative to the electrode carriers 178. As seen in FIG. 11B, retraction of the expandable element 177 causes it to engage the extensions 182 of the electrodes 179 such that the electrodes 179 rotate about the pivots 180 to the expanded configuration suitable for ITEV delivery of the electrodes 179. The expandable element 177 then is expanded, such that the electrodes 179 are forced through the vessel wall via an ITEV approach, as in FIG. 11C. ITEV PEF therapy then may proceed, as desired. Upon completion of the therapy, the expandable element 177 and the electrodes 179 are returned to the reduced profile configuration for retrieval from the patient.

Figure 12:
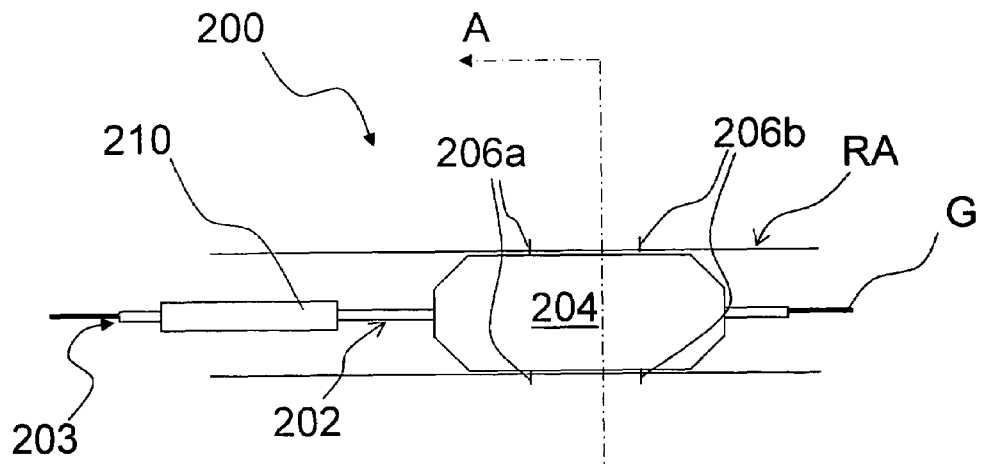
FIG. 12 is a schematic side-view, partially in section, of methods and apparatus for pulsed electric field neuromodulation via at least one angularly-aligned, longitudinally-spaced bipolar electrode pair positioned extravascularly via an intra-to-extravascular approach.

With reference now to FIG. 12, methods and apparatus for pulsed electric field neuromodulation via at least one angularly-aligned, longitudinally-spaced bipolar electrode pair positioned extravascularly via an intra-to-extravascular approach are described. FIG. 12, more specifically, shows an example of an ITEV PEF system 200 that comprises a catheter 202 having an expandable element 204 with at least one pair of longitudinally-spaced bipolar needle electrodes 206*a* and 206*b*. The needle electrodes 206*a-b* are positioned at substantially the same angular position along the expandable element (in FIG. 12, the system illustratively comprises two pairs of longitudinally-spaced, angularly-aligned bipolar electrodes 206*a-b* positioned at distinct circumferential positions). Angular alignment of the longitudinally-spaced bipolar electrodes 206*a-b* may align the PEF therapy with a longitudinal axis of target neural fibers, as described previously. The bipolar pairs of needle electrode 206 may comprise any desired longitudinal spacing; for example, the electrodes may comprise spacing in the range of about 0.5-10 mm.

The ITEV PEF system 200 may be delivered to an intravascular treatment site, such as a site within renal artery RA, using well-known percutaneous techniques. For example, the system 200 may be advanced over a guidewire G positioned with a lumen 203 of a catheter 202, which may be advanced through/within a guide catheter or a sheath 210. Once positioned at the treatment site, an expansion element 204 is expanded to force the bipolar needle electrodes 206 across the wall of the vessel such that the ends of the electrodes 206 are positioned extravascularly via an ITEV approach. The expansion element 204 may, for example, be expanded by (a) inflating a balloon, (b) self-expanding a basket or cage after positioning the element 204 distal of sheath 210, and/or (c) mechanical expanding a basket or cage via various push/pull and/or tension/compression techniques.

Positioning the electrodes 206 using an ITEV technique places the electrodes in closer proximity to target neural fibers that contribute to renal function. As discussed previously, renal nerves may be located in the adventitia of the renal arteries and/or in tissue immediately surrounding the renal arteries. Such ITEV positioning of the electrodes, as well as selected angular alignment of the bipolar electrode pair(s), may reduce energy requirements necessary to achieve desired neuromodulation, as compared to a PEF system comprising intravascularly-positioned electrodes.

The electrodes 206 preferably are of small enough caliber to safely cross the wall of renal artery RA without significant risk of bleeding, vessel wall injury, etc. For example, the electrodes may be of a caliber less than about 23 Gauge. Furthermore, the electrodes may be solid or may comprise one or more lumens. When with lumen(s), the needle electrodes may be configured for infusion of agents that either enhance the desired neuromodulatory effect (e.g., saline injection may be used to locally enhance conductivity during PEF therapy) or provide protective effects (e.g., cooling agents may be injected to protect non-target tissues).

The needle electrodes 206 also may be conductive along their entire lengths or may be insulated along at least part of their lengths. For example, the needle electrodes 206 can be insulated at locations other than their distal ends. Insulation along part of the lengths of electrodes 206 may reduce undesirable delivery of pulsed electric field therapy to non-target tissues, e.g., the intima or to the media of the patient's vessel. Such insulated electrodes preferably comprise lengths sufficient to place the non-insulated portions of the electrodes extravascularly at positions at least within the vasculature adventitia during ITEV positioning of the electrodes.

Figure 13A:
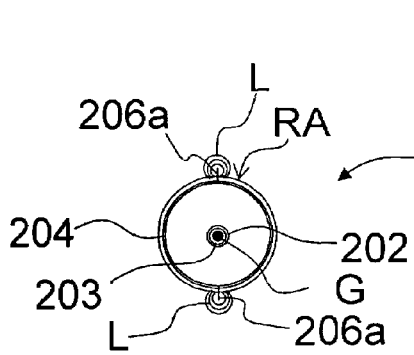
FIGS. 13A-13D are schematic cross-sectional views along section line A-A of FIG. 12, illustrating methods and apparatus for circumferential pulsed electric field modulation of target neural fibers via multiple pairs of angularly-aligned, longitudinally-spaced ITEV bipolar electrode pairs, each pair positioned at a different circumferential position.
Figure 13B:
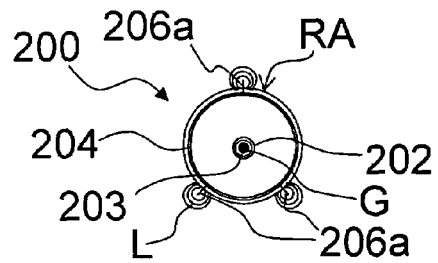
Figure 13C:
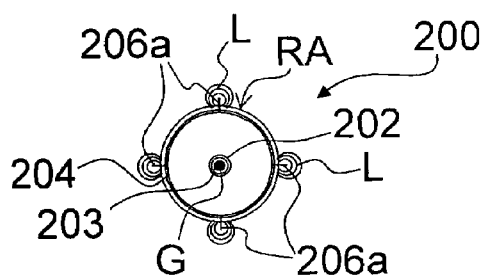

Referring now to FIGS. 13A-D, methods and apparatus for circumferential pulsed electric field modulation of target neural fibers via multiple pairs of angularly-aligned, longitudinally-spaced ITEV bipolar electrode pairs in which each electrode pair is positioned at a different circumferential position. FIGS. 13A-D illustrate several examples of the ITEV PEF system 200 along section line A-A of FIG. 12. In FIG. 13A, the ITEV PEF system 200 comprises two pairs of angularly-aligned, longitudinally-spaced bipolar electrodes 206 circumferentially positioned approximately 180° apart, as in FIG. 12. In FIG. 13B, the system 200 comprises three pairs of such bipolar electrodes spaced approximately 120° apart. In FIG. 13C, the system 200 comprises four pairs spaced roughly 90° apart, and in FIG. 13D, the system 200 comprises eight pairs spaced about 45° apart. As will be apparent, any desired number of electrode pairs may be provided. Furthermore, although the electrode pairs shown in FIGS. 13A-D have been equally circumferentially spaced, they alternatively may be circumferentially spaced at any other desired spacing, including any other desired unequal circumferential spacing.

Figure 13D:
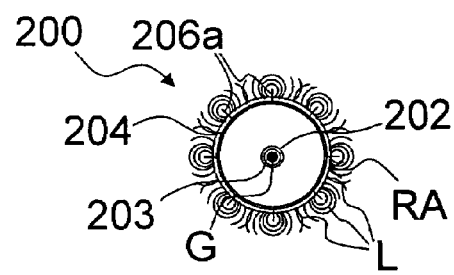

As illustrated by field lines L in FIGS. 13A-D, the tissue region affected by PEF therapy delivery across each bipolar electrode pair, e.g., the tissue region experiencing desired neuromodulation, is confined to a narrow circumferential segment of the treatment site. Providing multiple pairs of bipolar ITEV electrode pairs 206 may provide a more circumferential treatment. As seen in FIG. 13D, adding additional pairs of ITEV bipolar electrodes 206 eventually causes the circumferentially-affected segments to overlap, thereby providing full circumferential treatment. In some cases, it may be desirable to provide full circumferential treatment, while in other cases it may be desirable to provide less than complete circumferential treatment. The medical practitioner may provide any desired level of circumferential treatment and/or may utilize any desired number of circumferentially-spaced bipolar electrode pairs. Circumferential PEF therapy along a longitudinal segment of the patient's vessel may be achieved by collapsing the expansion element 204, rotating the catheter 202 a desired amount about its longitudinal axis, and then re-expanding the expansion element 204 to re-position electrode pairs 206 extravascularly for treatment of another circumferential longitudinal segment of the patient's vessel. This process can be repeated at a single longitudinal location as desired.

Figure 14A:
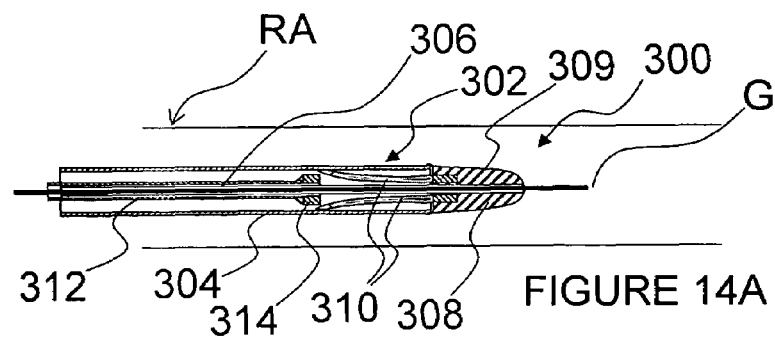
FIGS. 14A-14D are schematic side-sectional views and schematic side-views, partially in section, illustrating alternative methods and apparatus for pulsed electric field neuromodulation via electrodes positioned extravascularly via an intra-to-extravascular approach.
Figure 14B:
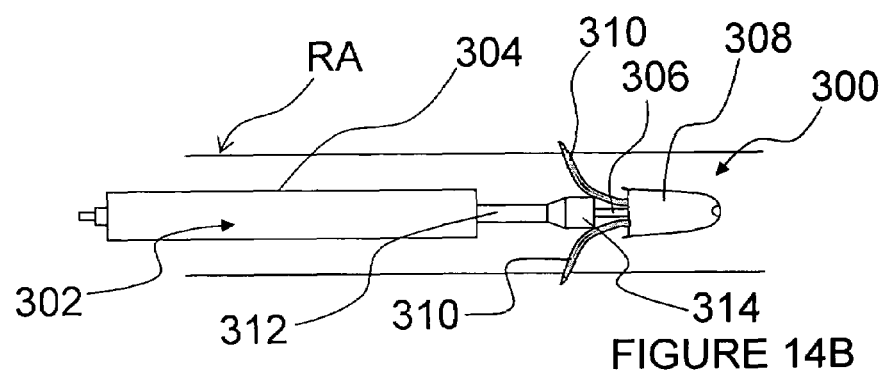

FIGS. 14A and 14B show additional ITEV PEF systems 300 that comprise a catheter 302 having an outer sheath 304, a guidewire tube 306, and an atraumatic nosecone 308. The guidewire tube 302 is coupled to and extends through or communicates with a lumen 309 of the atraumatic nosecone 308. The system 300 also includes a number of proximally-oriented ITEV needle electrodes 310 coupled to the nosecone 308 at their distal regions, and a pusher tube 312 coaxially positioned about the guidewire tube 306. The pusher tube 312 optionally has a flared tip 314, which may be relatively stiff and/or radiopaque. The electrodes 310 may be coupled to the PEF generator 50 via electrical contacts formed with or within the guidewire tube 306 (e.g., via a metallic braid, coil or wire on or near an outer diameter of the guidewire tube). The electrodes 310 may physically contact these electrical contacts to facilitate delivery of PEF therapy. In some embodiments, the flared tip 314 completes the circuit upon contacting the electrodes, as in FIG. 14B.

FIG. 14A shows the system 300 in the reduced delivery and retrieval configuration with the electrodes 310 positioned within the sheath 304. Upon intravascular placement at a treatment site, the sheath 304 is retracted and/or the guidewire tube 306 is advanced, such that the electrodes 310 are removed from the sheath 304. The electrodes 310 preferably are fabricated from an elastic material that resists deformation and applies a restoring force upon deformation. Furthermore, the electrodes 310 preferably are coupled to the nosecone 308 in a manner that biases the electrodes 310 to the reduced profile shown in FIG. 14A.

As seen in FIG. 14B, when the catheter 302 is positioned at a treatment site (e.g., within the renal artery RA), the pusher tube 312 is advanced relative to the guidewire tube 306 such that the flared tip 314 engages and elastically deforms the electrodes 310 radially outward. The electrodes 310 pierce the vessel to position the tips of the electrodes extravascularly via an ITEV approach. The catheter 302 optionally may be retracted after deformation of the electrodes 310 to engage the electrodes with the patient's vessel and place the electrodes extravascularly. PEF therapy then may proceed to achieve desired neuromodulation. Upon completion of the treatment, the pusher tube 312 is retracted relative to the guidewire tube 306 and the electrodes 310. The guidewire tube 306 is advanced slightly to release the electrodes 310 from the vessel wall. The restoring force provided by the electrodes 310 returns the electrodes 310 to the reduced at-rest profile. The sheath 304 then may be advanced relative to the guidewire tube 306, such that the needle electrodes 310 are once again positioned within the sheath 304 as in FIG. 16A for retrieval and removal from the patient.

In an additional or alternative embodiment of the apparatus of FIGS. 14A and 14B, the needle electrodes 310 may be replaced with needle housings through which the needle electrodes may be advanced. The needle housings are expanded into contact with a vessel wall, and the needle electrodes then are advanced across the vessel wall. Such advancement may be accomplished via a variety of mechanical means. For example, advancement of the pusher tube past a specified position relative to the guidewire tube, the nosecone and/or the needle housings may release a spring-loaded member that advances the needles.

Figure 14C:
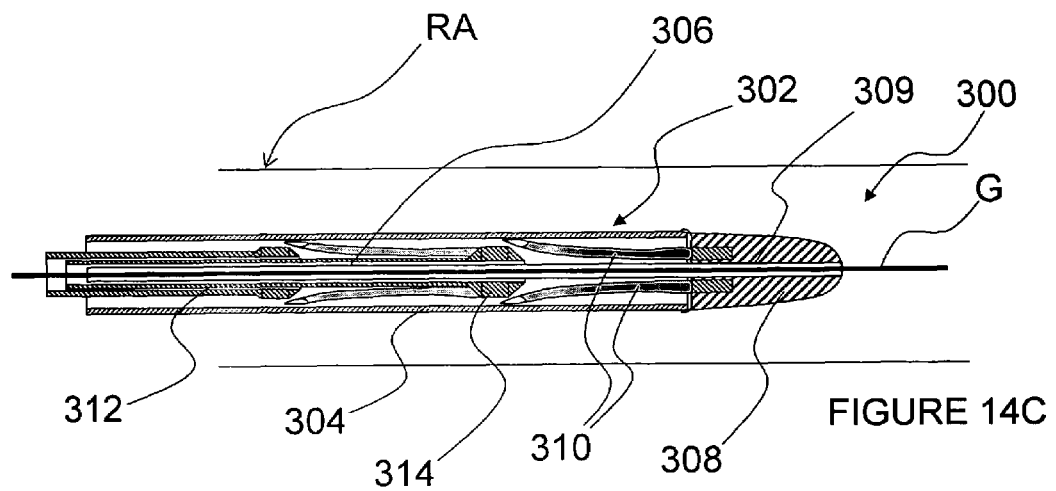
Figure 14D:
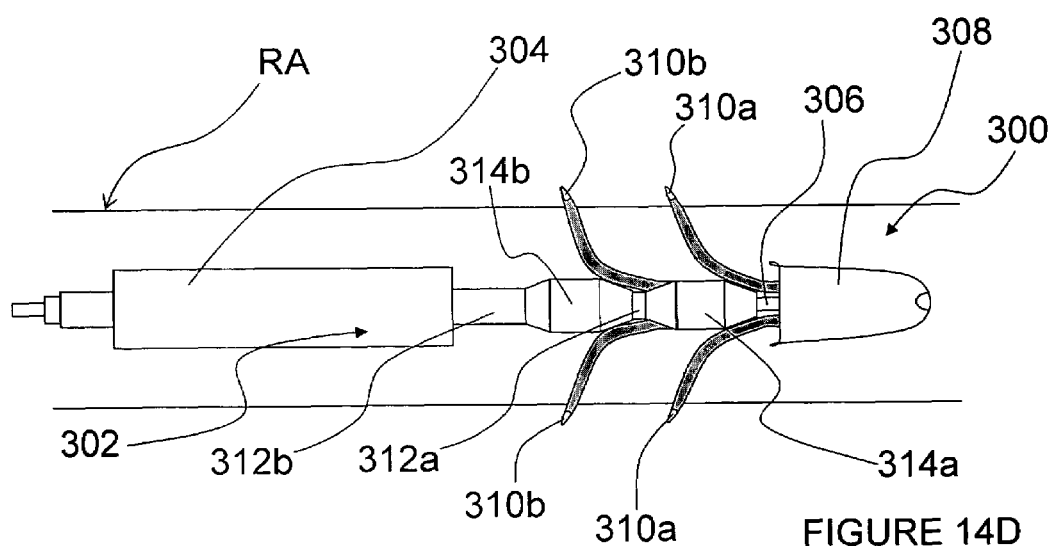

FIGS. 14C and 14D illustrate an alternative embodiment of the ITEV PEF system 300 comprising one or more longitudinally spaced pairs of bipolar electrodes. In FIGS. 14C and 14D, needle electrodes 310a are coupled to the nosecone 308, and needle electrodes 310b are coupled to a proximal region of a first flared tip 314a of a first pusher tube 312a. The system 300 further comprises a second pusher tube 312b having a second flared tip 314b. The second pusher tube 312b is coaxially disposed about the first pusher tube 312a.

Electrodes 310a and 310b form one or more longitudinally spaced pairs of bipolar electrodes. For example, electrodes 310a may comprise active electrodes and electrodes 310b comprise return electrodes, or vice versa. As seen in FIG. 14C, the electrodes may be delivered within the sheath 304. Once positioned at a treatment site, the sheath 304 may be withdrawn, and the electrodes 310 may be positioned extravascularly via an ITEV approach, as in FIG. 14D. Specifically, the first pusher tube 312a may be advanced relative to the guidewire tube 306, such that first flared tip 314a impinges upon and deforms the needle electrodes 310a. This urges the electrodes 310a across the vessel wall. Likewise, the second pusher tube 312b may be advanced relative to the first pusher tube 312a such that the second flared tip 314b impinges upon and deforms the needle electrodes 310b. This mechanism urges the electrodes 310b across the vessel wall. In the embodiment of FIGS. 14C and 14D, the flared tips 314 comprise distal profiles that provide gradual transitions for deforming the electrodes 310.

Figure 15A:
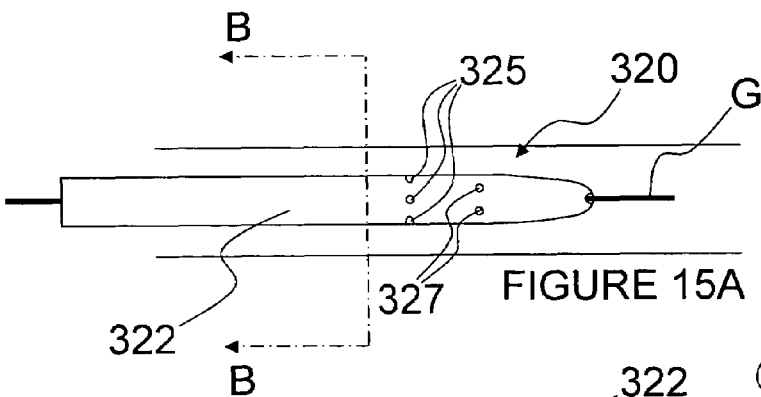
FIGS. 15A-15C are schematic side-views, partially in section, as well as a cross-sectional view along section line B-B of FIG. 15A, of further alternative methods and apparatus for pulsed electric field neuromodulation via electrodes positioned extravascularly via an intra-to-extravascular approach.
Figure 15C:
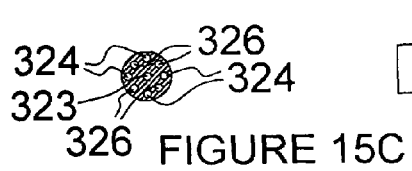
Figure 15B:
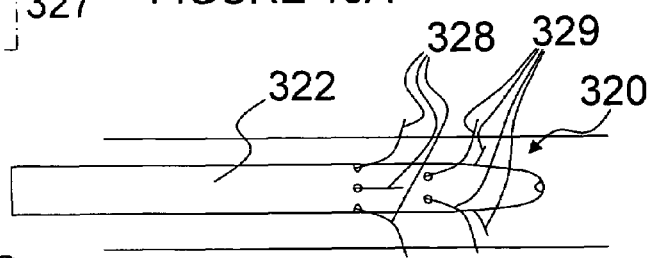

FIGS. 15A-C show examples of another ITEV PEF system 320 that comprises a catheter 322 having (a) a plurality of proximal electrode lumens 324 terminating at proximal side ports 325, (b) a plurality of distal electrode lumens 326 terminating at distal side ports 327, and (c) a guidewire lumen 323. The catheter 322 preferably comprises an equal number of proximal and distal electrode lumens. The system 320 also includes proximal needle electrodes 328 that may be advanced through the proximal electrode lumens 324 and needle electrodes 329 that may be advanced through the distal electrode lumens 326.

As illustrated in FIG. 15A, the catheter 322 may be advanced over the guidewire 321 via the lumen 323 to a treatment site within the patient's vasculature (e.g., to a treatment site within the patient's renal artery RA). During intravascular delivery, the electrodes 328 and 329 are positioned such that their non-insulated and sharpened distal regions are positioned within the lumens 324 and 326, respectively. Once positioned at a treatment site, a medical practitioner may advance the electrodes via their proximal regions that are located external to the patient. As seen in FIG. 15B, such advancement causes the distal regions of the electrodes 326 and 329 to exit side ports 325 and 327, respectively, and pierce the wall of the patient's vasculature such that the electrodes are positioned extravascularly via an ITEV approach.

The proximal electrodes 328 can be connected to PEF generator 50 as active electrodes and the distal electrodes 329 can serve as return electrodes. In this manner, the proximal and distal electrodes form bipolar electrode pairs that align PEF therapy with a longitudinal axis or direction of the patient's vasculature. As will be apparent, the distal electrodes 329 alternatively may comprise the active electrodes and the proximal electrodes 328 may comprise the return electrodes. Furthermore, the proximal and/or the distal electrodes may comprise both active and return electrodes. Any combination of active and distal electrodes may be utilized, as desired.

When the electrodes 328 and 329 are positioned extravascularly, PEF therapy may proceed to achieve desired neuromodulation. After completion of the PEF therapy, the electrodes may be retracted within lumens 324 and 326. The catheter 322, as well as the guidewire 321 then may be removed from the patient to complete the procedure. Additionally or alternatively, the catheter may be repositioned to provide PEF therapy at another treatment site.

Figure 16A:
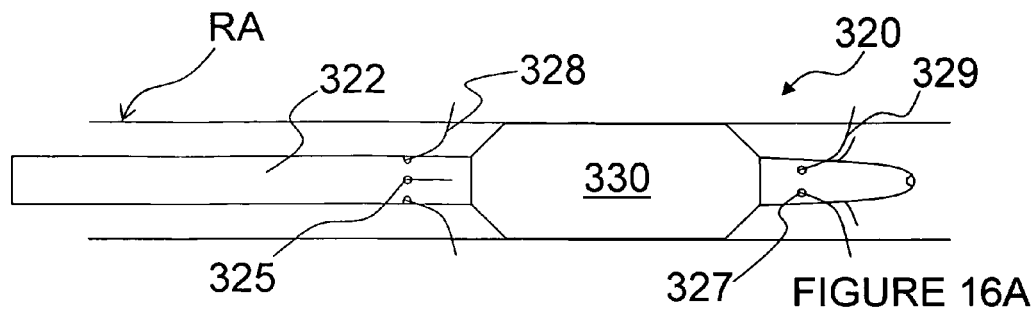
FIGS. 16A and 16B are schematic side-views of alternative embodiments of the methods and apparatus of FIG. 15.
Figure 16B:
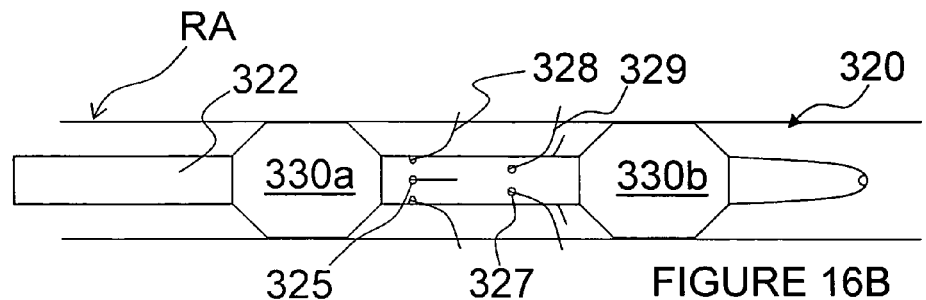

FIGS. 16A and 16B show alternative embodiments of the ITEV PEF system 320. In FIG. 16A, the catheter 322 of the system 320 further comprises an expandable centering element 330, which may comprise an inflatable balloon or an expandable basket or cage. In use, a centering element 330 may be expanded prior to deployment of the needle electrodes 328 and 329 to center the catheter 322 within the patient's vessel (e.g., within renal artery RA). Centering the catheter 322 is expected to facilitate delivery of all needle electrodes to desired depths within/external to the patient's vessel (e.g., to deliver all of the needle electrodes to the same depth).

In FIG. 16A, the illustrated centering element 330 is positioned between the proximal side ports 325 and the distal side ports 327, i.e., between the delivery positions of the proximal and distal electrodes. However, it should be understood that centering element 330 additionally or alternatively may be positioned at a different location or at multiple locations along the length of catheter 322 (e.g., at a location proximal of side ports 325 and/or at a location distal of side ports 327). In FIG. 16B, the system 320 illustratively comprises a first centering element 330a positioned proximal of the proximal side ports 325 and a second centering element 330b positioned distal of the distal side ports 327.

Figure 17A:
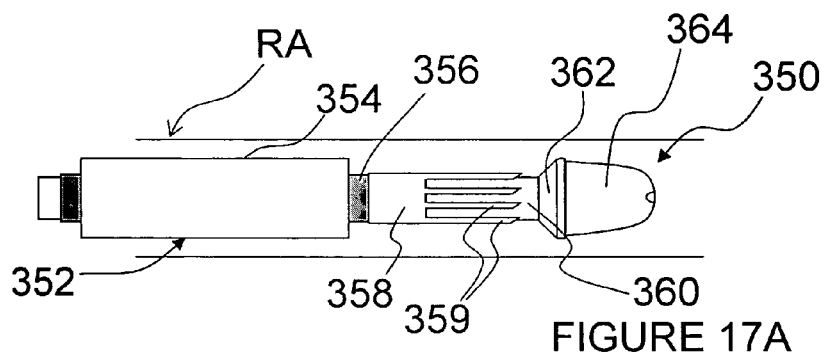
FIGS. 17A-17E are schematic side-views, partially in section, of still further methods and apparatus for pulsed electric field neuromodulation via electrodes positioned extravascularly via an intra-to-extravascular approach.
Figure 17B:
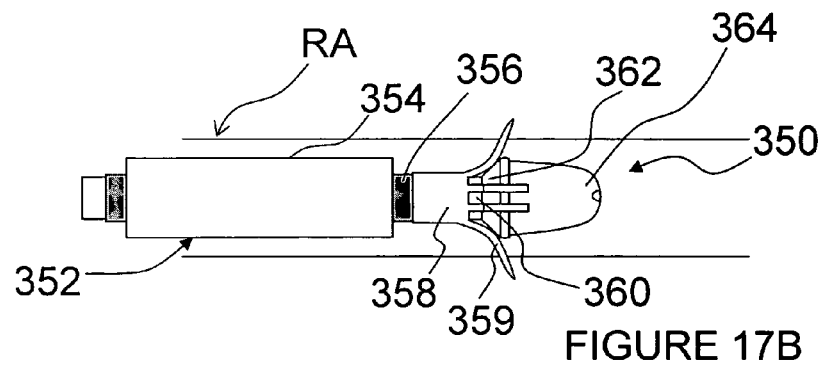

Referring now to FIGS. 17A-E, ITEV PEF systems 350 utilizing one or more hypotubes are described. In the embodiment of FIGS. 17A and 17B, the ITEV PEF system 350 comprises a catheter 352 having an outer sheath 354, an outer shaft 356, a hypotube 358 with multiple distal extensions 359, and an inner shaft 360 with a guide block 362. The inner shaft 360 terminates at an atraumatic tip 364, and a guidewire lumen preferably extends through the inner shaft and the atraumatic tip. The hypotube 358 is connected proximally to the outer shaft 356, and the outer shaft 356 is coaxially positioned over the inner shaft 360.

The hypotube 358 can have extensions 359 that may be fabricated by cutting away portions of the hypotube. The hypotube 358 may be fabricated from a conductive material, such as a metal alloy or platinum, or the hypotube may comprise a relative non-conductive material. The extensions 359 may be selectively insulated and/or non-insulated, and they may be electrically coupled to the PEF generator 50 to provide one or more extension electrodes. The extension electrodes may, for example, be etched onto the hypotube and its extensions, e.g., via a metal deposition process. Electrical contacts for energy delivery may be exposed at the tips of insulated extensions 359; alternatively, the non-insulated contacts may extend across all or part of the lengths of the extensions. Furthermore, the entire hypotube 358 may comprise an electrode when the hypotube is fabricated from a conductive material.

The extension electrode(s) 359 may be of a common polarity or may be of different polarities. When of different polarities, PEF therapy may be delivered across the electrodes in a bipolar fashion. When of common polarity, the electrodes may be utilized in a monopolar fashion, e.g., with an external ground pad. Alternatively, the catheter 352 optionally may comprise one or more additional electrodes of opposite polarity along its length that may be utilized in a bipolar fashion with the extension electrode(s) 359 of the hypotube 358. In one embodiment, the outer shaft 356 comprises at least a second hypotube along its length having extension electrode(s) that serve as the additional electrode(s) of opposite polarity and may be utilized to form spaced bipolar electrode pair(s) for delivery of the PEF therapy.

As seen in FIG. 17A, the catheter 352 may be advanced to a treatment site within a patient's vasculature, such as a treatment site within renal artery RA, using well-known percutaneous techniques (e.g., through a guide catheter). Once properly positioned, the outer sheath 354 may be retracted to expose the hypotube 358, and then the outer shaft 356 may be advanced relative to inner shaft 360 to drive the extensions 359 against the guide block 362. As seen in FIG. 17B, the guide block 362 provides a tapered transition that progressively deforms extensions 359 in an elastic or plastic manner as the outer shaft 354 is advanced relative to the inner shaft 360. This deformation directs the extensions 359 radially outward to detone the extension electrodes. Continued advancement of the outer shaft causes the extension electrodes to penetrate the vessel wall and to be positioned extravascularly via an ITEV approach. With the extension electrodes 359 positioned extravascularly, PEF therapy may proceed.

Upon completion of the PEF therapy, the extensions 359 once again may be collapsed against the outer shaft 356 for retrieval of the system 350 from the patient. If the deformation of the extensions 359 comprises elastic deformation, the outer shaft 356 may be retracted relative to the wall of renal artery RA to remove the extensions from the wall. The extensions 359 then will return to their at-rest configuration of FIG. 17A. If the deformation is plastic, then the extensions 359 may, for example, be collapsed by advancing the outer sheath 354 or a guide catheter over the outer shaft 356 such that the sheath 354 abuts the bases of the extensions 359. The outer shaft 356 then may be retracted while the sheath 354 is held stationary or advanced relative to the outer shaft to collapse the extensions 359 within the sheath 354 for retrieval of the system 350 from the patient.

Figure 17C:
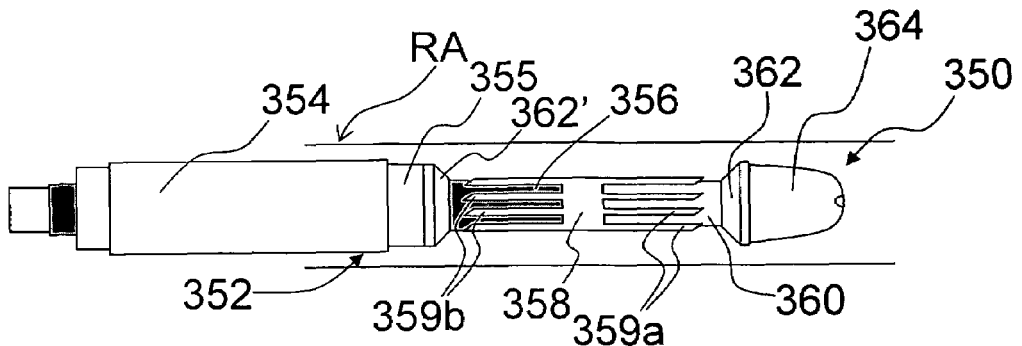
Figure 17D:
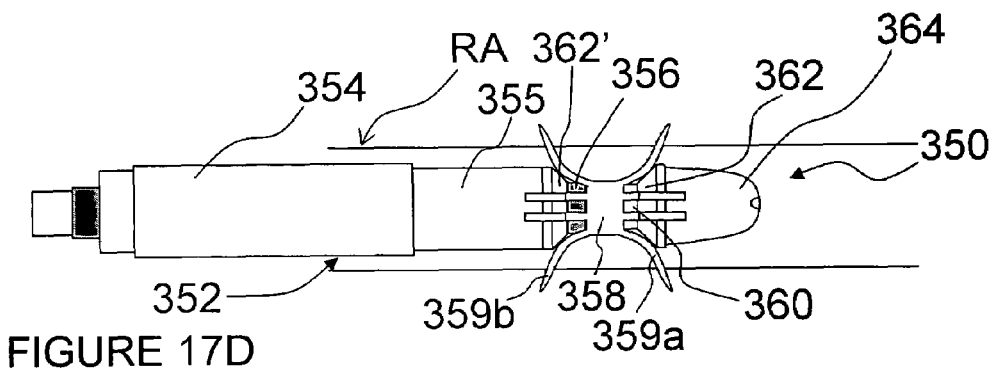

As seen in FIGS. 17C and 17D, the ITEV PEF system 350 optionally may comprise one or more longitudinally spaced pairs of ITEV electrodes. In FIGS. 17C and 17D, the hypotube 358 comprises distal extensions 359*a* and proximal extensions 359*b*. The distal extensions 359*a* may be deployed extravascularly in the manner described previously. For ITEV deployment of the proximal extensions 359*a*, the system 350 further comprises a proximal pusher tube 355 having a distally-oriented guide block 362' for deforming the proximal extensions 359*b*. The pusher tube 355 is coaxially disposed over the outer shaft 356, but within the outer sheath 354. As seen in FIG. 17D, the pusher tube 355 may be advanced relative to the outer shaft 356 in order to deform the proximal extensions 359*b* and position the extension electrodes extravascularly via an ITEV approach. The proximal and distal extension electrodes of the hypotube 358 form one or more longitudinally spaced bipolar electrode pairs.

Figure 17E:
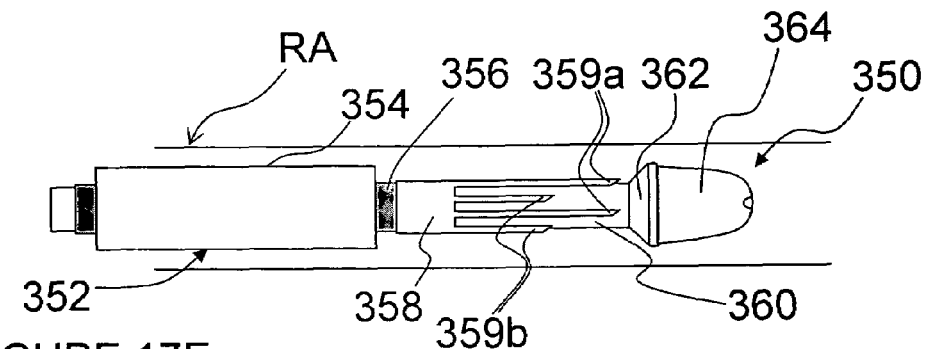

In FIG. 17E, ITEV PEF system 350 again comprises the distal extensions 359*a* and the proximal extensions 359*b*. However, in the embodiment of FIG. 17E, the proximal and distal extensions are all distally-oriented, with the distal extensions 359*a* being of a greater length than the proximal extensions 359*b*. During extravascular placement of the extensions, the additional length of the distal extensions 359*a* causes the distal extensions to pierce the wall of the patient's vessel more distally than do the proximal extensions 359*b*. In this manner, the proximal and distal extensions 359*a-b* are longitudinally spaced apart from one another when deployed extravascularly. After completion of extravascular PEF therapy, the distal orientation of the proximal and distal extensions 359*a-b* facilitates collapse and retrieval of the extensions. The outer shaft 356 may be retracted while the sheath 354 is held stationary or advanced relative to the outer shaft to collapse the extensions 359*a-b* within the sheath 354 for retrieval of the system 350 from the patient.

Although several examples of the ITEV systems 350 shown in FIGS. 17A-E illustrate deployment of the ITEV extension electrodes 359 via guide block(s) 362, it should be understood that the electrodes may be deployed via a variety of alternative techniques. For example, a push/pull mechanism, such as pull wire, may be utilized to deform the hypotube extensions. Alternatively, a pressure or vacuum channel may be used. An array of hypotubes and/or hypotube extension electrodes optionally may be deployed via a single deployment mechanism.

With reference to FIGS. 18A-D, alternative embodiments of the ITEV PEF system 350 are described. In FIGS. 18A-D, the guide block(s) 362 have been replaced with alternative deployment mechanisms comprising at least one expandable member, such as an inflatable balloon 366. Furthermore, the hypotube 358 has been replaced with a stent-like element 370 having the extensions 359. As will be apparent, the balloon(s) 366 alternatively may be used in combination with the hypotube 358, and/or the stent-like element 370 alternatively may be used in combination with the guide block(s) 362.

As with the hypotube 358, the stent-like element 370 may be completely conductive and may serve as a unitary electrode. Alternatively, the stent-like element 370 may be fabricated from a relatively insulating material with electrode contacts that are etched or deposited onto the element and/or its extensions. A variety of electrode configurations may be provided. Furthermore, the multiple elements 370 (or a combination of hypotubes 358 and elements 370) may be provided. In addition or as an alternative to the deployment mechanisms illustrated in FIG. 18, the extensions 359 may be deployed via other deployment mechanisms, such as push/pull mechanisms (e.g., a pull wire) or a pressure/vacuum channel.

As seen in the embodiment of FIGS. 18A and 18B, the system 350 may be positioned at a treatment site, and the balloon 366 coupled to the inner shaft 360 may be inflated into contact with the vessel wall. As seen in FIG. 18A, the inflated balloon 366 centers the system 350 within the vessel and provides a tapered guide path that provides a smooth transition for deformation of the extensions 359 of the stent-like element 370 during ITEV placement of the extension electrodes. As seen in FIG. 18B, the outer shaft 356 may be advanced relative to the inner shaft 360 such that the extensions 359 begin to deform about the balloon and are directed radially outward. This deformation optionally may be assisted via additional deployment mechanisms, such as pull-wires, to begin deformation of the extensions 359. Continued advancement of the outer shaft 356 relative to the inner shaft causes the extensions 359 to pierce the vessel wall so that the ends of the extension electrodes 359 are positioned extravascularly via an ITEV approach.

As seen in FIG. 18C, the stent-like element 370 may comprise longitudinally spaced extensions 359a and 359b to provide longitudinally spaced bipolar electrode pairs. In FIG. 18C, the inner shaft 360 comprises distal and proximal expandable elements, illustratively a distal balloon 366a and a proximal balloon 366b. The stent-like element 370 is positioned between the proximal and distal balloon, with the extensions 359a and 359b overlapping the distal and proximal balloons 366a-b, respectively. This overlap obviates a need for the outer shaft 356 shown in FIGS. 18A and 18B. ITEV placement of the extension electrodes 359a-b is achieved by inflating balloons 366.

As seen in FIG. 18D, the stent-like element 370 with proximal and/or distal extensions 359 may be positioned over an expandable element, such as inflatable balloon 366. The expandable element 370 may be coupled to the shaft 360 proximally and/or distally (e.g., at a distal collar 368a and at a proximal collar 368b). At least one of the collars 368a or 368b is slidingly coupled to the shaft 360 to facilitate expansion of the expandable element 370 during expansion of the balloon 366. As with the embodiment of FIG. 18C, the positioning of the expandable element 370 relative to the balloon 366 obviates a need for an outer shaft. Rather, ITEV placement of the extension electrodes is achieved by inflating the balloon 366.

Referring now to FIGS. 19A and 19B, an alternative ITEV PEF 400 system is described comprising an expandable stent. The ITEV PEF system 400 comprises a stent 402 having extensions 404 configured to pierce the wall of a patient's vasculature upon expansion of the stent. The extensions 404 may be proximal and distal extensions that form longitudinally spaced bipolar electrode pairs. Additionally, the extensions 404 can be electrically coupled to the PEF generator 50 and utilized as extravascular electrodes for delivery of PEF therapy.

As seen in FIG. 19A, a stent 402 may be delivered to an intravascular treatment site, such as a site within renal artery RA, in a reduced profile configuration. The stent 402 may, for example, be positioned on a delivery and deployment catheter, such as a balloon catheter 410, during advancement and deployment at the treatment site. The catheter 410 may (temporarily) electrically couple the stent to the PEF generator. As seen in FIG. 19B, when the stent 402 is properly positioned at the treatment site, it may be deployed to contact the vessel wall (e.g., via the deployment catheter) such that extensions 404 penetrate the wall of the vessel. This accordingly positions the extension electrodes extravascularly via an ITEV approach. PEF therapy then may proceed, and upon completion the catheter 410 may be collapsed and removed from the patient.

The system 400 facilitates repeat PEF therapy at a later time. For example, by temporarily electrically re-coupling the catheter 410 or some other electrical coupling element to the stent 402, the system 400 can repeat PEF therapy as desired. When utilized to achieve renal denervation, such repeat therapy may, for example, be repeated upon evidence of re-innervation of the renal(s).

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired. It is intended in the appended claims to cover all such changes and modifications that fall within the true spirit and scope of the invention.

We claim:

1. An apparatus for electric field neuromodulation via an intra-to-extravascular approach, the apparatus comprising:
an electric field generator;
a catheter comprising an elongated shaft; and
at least one electrode electrically coupled to the electric field generator and carried by the elongated shaft, the electrode configured for intravascular delivery and extravascular placement via an intra-to-extravascular approach,
wherein the electrode is configured for extravascular delivery of an electric field to induce neuromodulation, and
wherein a distal segment of the elongated shaft is configured to be positioned within a patient, and wherein a proximal segment of the elongated shaft is configured to be external to the patient during neuromodulation.

2. The apparatus of claim I further comprising a piercing element configured for intravascular delivery, the piercing element configured to pierce a wall of vasculature of a patient from within the vasculature.

3. The apparatus of claim 2, wherein the electrode comprises the piercing element.

4. The apparatus of claim 2, wherein the piercing element comprises a needle or cannula.

5. The apparatus of claim 4, wherein the electrode is configured for extravascular placement through a lumen of the needle.

6. The apparatus of claim 1, wherein the electrode is coupled to an expandable element of the catheter.

7. An apparatus for electric field neuromodulation via an intra-to-extravascular approach, the apparatus comprising:
an electric field generator; and
at least one electrode electrically coupled to the electric field generator, the electrode configured for intravascular delivery and extravascular placement via an intra-to-extravascular approach,
wherein the electrode is configured for extravascular delivery of an electric field to induce neuromodulation, and
wherein the electrode comprises at least one bipolar electrode pair having a first electrode and a second electrode, the bipolar electrode pair coupled to the electric field generator.

8. The apparatus of claim 7, wherein the apparatus is configured for extravascular delivery of the electric field across the bipolar electrode pair.

9. The apparatus of claim 7, wherein the first electrode is configured for extravascular placement via an intra-to-extravascular approach, and the second electrode is configured for intravascular placement.

10. The apparatus of claim 9, wherein the first electrode comprises an active electrode and the second electrode comprises a return electrode.

11. The apparatus of claim 7, wherein both the first electrode and the second electrode are configured for extravascular placement via an intra-to-extravascular approach.

12. The apparatus of claim 7, wherein the first electrode and the second electrode are longitudinally spaced apart from one another in a deployed configuration.

13. The apparatus of claim 7, wherein the first electrode and the second electrode are angularly-aligned with one another relative to a circumference of a patient's vasculature.

14. An apparatus for electric field neuromodulation via an intra-to-extravascular approach, the apparatus comprising:
an electric field generator;
at least one electrode electrically coupled to the electric field generator, the electrode configured for intravascular delivery and extravascular placement via an intra-to-extravascular approach,
an external ground pad, wherein the electrode is configured for monopolar extravascular delivery of the electric field to induce neuromodulation.

15. An apparatus for electric field neuromodulation via an intra-to-extravascular approach, the apparatus comprising:
an electric field generator; and
at least one electrode electrically coupled to the electric field generator, the electrode configured for intravascular delivery and extravascular placement via an intra-to-extravascular approach,
wherein the electrode is configured for extravascular delivery of an electric field to induce neuromodulation, and
wherein the apparatus is configured for extravascular infusion of agents.

16. The apparatus of claim 15, wherein the apparatus is configured for extravascular infusion of agents that enhance neuromodulation or provide protective effects.

17. A method for electric field neuromodulation via an intra-to-extravascular approach, the method comprising:
intravascularly advancing at least one electrode to a treatment site within vasculature of a patient;
passing a portion of the electrode through at least a portion of a wall of the vasculature to position the electrode at an extravascular location via an intra-to-extravascular approach; and
extravascularly delivering an electric field via the electrode to induce neuromodulation.

18. The method of claim 17, wherein intravascularly advancing at least one electrode to a treatment site within vasculature of a patient further comprises intravascularly moving the electrode to a treatment site within a renal artery of the patient.

19. The method of claim 17, wherein intravascularly advancing at least one electrode to a treatment site within vasculature of a patient further comprises intravascularly moving an intravascular catheter having the electrode to the treatment site within the vasculature of the patient.

20. The method of claim 19, wherein passing a portion of the electrode through at least a portion of a wall of the vasculature to position the electrode at an extravascular location via an intra-to-extravascular approach further comprises expanding an expandable element of the catheter.

21. The method of claim 17, wherein intravascularly advancing at least one electrode to a treatment site within vasculature of a patient further comprises moving the electrode through an intravascular catheter positioned at the treatment site.

22. The method of claim 17, wherein extravascularly delivering an electric field to induce neuromodulation further comprises extravascularly applying the electric field to modulate a neural fiber that contributes to renal function.

23. The method of claim 22, wherein modulating a neural fiber that contributes to renal function further comprises inducing an effect in the neural fiber chosen from the group consisting of irreversible electroporation, electrofusion, necrosis, apoptosis, ablation, gene expression alteration, cytokine upregulation alteration, and combinations thereof.

24. The method of claim 17 wherein passing a portion of the electrode through at least a portion of a wall of the vasculature to position the electrode at an extravascular location via an intra-to-extravascular approach further comprises piercing the wall of the vasculature, and advancing the electrode through the wall piercing.

25. The method of claim 24, wherein piercing the wall of the vasculature further comprises forcing the electrode through the wall of the vasculature.

26. The method of claim 17, wherein advancing at least one electrode to a treatment site further comprises advancing at least one bipolar electrode pair to the treatment site.

27. The method of claim 26, wherein passing a portion of the electrode through at least a portion of a wall of the vasculature to position the electrode at an extravascular location via an intra-to-extravascular approach further comprises moving the bipolar electrode pair extravascularly, and wherein extravascularly delivering an electric field further comprises extravascularly delivering the electric field across the bipolar electrode pair.

28. The method of claim 26, wherein passing a portion of the electrode through at least a portion of a wall of the vasculature to position the electrode at an extravascular location via an intra-to-extravascular approach further comprises positioning a first electrode of the bipolar electrode pair at the extravascular location and positioning a second electrode of the bipolar electrode pair at an intravascular location.

29. The method of claim 17 further comprising infusing an agent to enhance the neuromodulation.

30. The method of claim 17 further comprising infusing an agent to protect non-target tissue.

31. The method of claim 17 wherein extravascularly delivering an electric field via the electrode to induce neuromodulation further comprises extravascularly delivering a pulsed electric field via the electrode to induce neuromodulation.

32. The method of claim 17 wherein extravascularly delivering an electric field via the electrode to induce neuromodulation further comprises extravascularly delivering RE energy via the electrode to induce neuromodulation.

33. The method of claim 17 wherein extravascularly delivering an electric field via the electrode to induce neuromodulation further comprises extravascularly delivering thermal energy via the electrode to induce neuromodulation.

34. The method of claim 33 wherein extravascularly delivering RF energy via the electrode to induce neuromodulation further comprises extravascularly delivering ablative energy via the electrode to induce neuromodulation.

* * * * *

UNITED STATES PATENT AND TRADEMARK OFFICE
CERTIFICATE OF CORRECTION

PATENT NO. : 7,620,451 B2
APPLICATION NO. : 11/363867
DATED : November 17, 2009
INVENTOR(S) : Demarais et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 545 days.

Signed and Sealed this

Twenty-sixth Day of October, 2010

David J. Kappos
*Director of the United States Patent and Trademark Office*